United States Patent
Hayashi et al.

(10) Patent No.: US 11,217,754 B2
(45) Date of Patent: Jan. 4, 2022

(54) ORGANIC ELECTROLUMINESCENCE DEVICE

(71) Applicants: HODOGAYA CHEMICAL CO., LTD., Tokyo (JP); SFC CO., LTD., Chungcheongbuk-do (KR)

(72) Inventors: Shuichi Hayashi, Tokyo (JP); Naoaki Kabasawa, Tokyo (JP); Shunji Mochiduki, Tokyo (JP); Se-Jin Lee, Chungcheongbuk-do (KR); Oun-gyu Lee, Chungcheongbuk-do (KR); Bong-Ki Shin, Chungcheongbuk-do (KR)

(73) Assignees: HODOGAYA CHEMICAL CO., LTD., Tokyo (JP); SFC CO., LTD., Chungcheongbuk-Do (KR)

( * ) Notice: Subject to any disclaimer, the term of this patent is extended or adjusted under 35 U.S.C. 154(b) by 0 days.

(21) Appl. No.: 15/329,083

(22) PCT Filed: Jul. 27, 2015

(86) PCT No.: PCT/JP2015/071285
§ 371 (c)(1),
(2) Date: Jan. 25, 2017

(87) PCT Pub. No.: WO2016/017594
PCT Pub. Date: Feb. 4, 2016

(65) Prior Publication Data
US 2018/0212153 A1 Jul. 26, 2018

(30) Foreign Application Priority Data

Jul. 29, 2014 (JP) .............................. JP2014-153658
Oct. 3, 2014 (JP) .............................. JP2014-204426

(51) Int. Cl.
*H01L 51/00* (2006.01)
*C07C 211/54* (2006.01)
(Continued)

(52) U.S. Cl.
CPC ........ *H01L 51/0059* (2013.01); *C07C 211/54* (2013.01); *C07C 211/58* (2013.01);
(Continued)

(58) Field of Classification Search
None
See application file for complete search history.

(56) References Cited

U.S. PATENT DOCUMENTS 5,639,914 A 6/1997 Tomiyama et al.
5,707,747 A 1/1998 Tomiyama et al.
(Continued)

FOREIGN PATENT DOCUMENTS

JP 7-126615 5/1995
JP 8-48656 2/1996
(Continued)

OTHER PUBLICATIONS

Machine English translation of Ahn et al. (JP 2014-513064 A). Jun. 30, 2018.*
(Continued)

*Primary Examiner* — Jay Yang
*Assistant Examiner* — J. L. Yang
(74) *Attorney, Agent, or Firm* — Greenblum & Bernstein, P.L.C.

(57) ABSTRACT

According to the present invention, there is provided an organic electroluminescent device which has an anode, a hole transport layer, a luminous layer, an electron transport layer, and a cathode arranged in order of description. The device is characterized in that: the hole transport layer includes a specific arylamine compound, and that the lumi-
(Continued)

| 9 | CATHODE |
| 8 | ELECTRON INJECTION LAYER |
| 7 | ELECTRON TRANSPORT LAYER |
| 6 | LUMINOUS LAYER |
| 5b | SECOND HOLE TRANSPORT LAYER |
| 5a | FIRST HOLE TRANSPORT LAYER |
| 5 | HOLE TRANSPORT LAYER |
| 3 | HOLE INJECTION LAYER |
| 2 | TRANSPARENT ANODE |
| 1 | TRANSPARENT SUBSTRATE | nous layer includes a specific indenoindole derivative or a specific carbazole derivative. The organic EL device of the present invention has improved efficiency of hole transport from the hole transport layer to the luminous layer and also improved efficiency of electron transport from the electron transport layer to the luminous layer, in comparison to conventional organic EL devices.

9 Claims, 50 Drawing Sheets

(51) Int. Cl.

| | |
|---|---|
| C07C 211/58 | (2006.01) |
| C07D 403/04 | (2006.01) |
| C07C 211/61 | (2006.01) |
| C07D 491/048 | (2006.01) |
| C07D 495/04 | (2006.01) |
| C07D 495/14 | (2006.01) |
| C07D 403/10 | (2006.01) |
| C09K 11/06 | (2006.01) |
| C07D 493/04 | (2006.01) |
| C07C 217/90 | (2006.01) |
| C07D 235/08 | (2006.01) |
| C07D 239/26 | (2006.01) |
| C07D 307/91 | (2006.01) |
| C07D 333/76 | (2006.01) |
| C07D 401/10 | (2006.01) |
| C07D 401/14 | (2006.01) |
| C07D 403/14 | (2006.01) |
| C07D 409/12 | (2006.01) |
| C07D 471/04 | (2006.01) |
| H01L 51/50 | (2006.01) |

(52) U.S. Cl.
CPC .......... *C07C 211/61* (2013.01); *C07C 217/90* (2013.01); *C07D 235/08* (2013.01); *C07D 239/26* (2013.01); *C07D 307/91* (2013.01); *C07D 333/76* (2013.01); *C07D 401/10* (2013.01); *C07D 401/14* (2013.01); *C07D 403/04* (2013.01); *C07D 403/10* (2013.01); *C07D 403/14* (2013.01); *C07D 409/12* (2013.01); *C07D 471/04* (2013.01); *C07D 491/048* (2013.01); *C07D 493/04* (2013.01); *C07D 495/04* (2013.01); *C07D 495/14* (2013.01); *C09K 11/06* (2013.01); *H01L 51/006* (2013.01); *H01L 51/0052* (2013.01); *H01L 51/0058* (2013.01); *H01L 51/0061* (2013.01); *H01L 51/0067* (2013.01); *H01L 51/0071* (2013.01); *H01L 51/0072* (2013.01); *H01L 51/0073* (2013.01); *H01L 51/0074* (2013.01); *C07C 2603/18* (2017.05); *H01L 51/0085* (2013.01); *H01L 51/5016* (2013.01); *H01L 51/5024* (2013.01); *H01L 51/5064* (2013.01); *H01L 51/5072* (2013.01)

(56) References Cited

U.S. PATENT DOCUMENTS

| | | | |
|---|---|---|---|
| 5,792,557 | A | 8/1998 | Nakaya et al. |
| 6,878,469 | B2 | 4/2005 | Yoon et al. |
| 7,357,992 | B2 | 4/2008 | Kato et al. |
| 7,402,701 | B2 | 7/2008 | Kato et al. |
| 7,759,030 | B2 | 7/2010 | Abe et al. |
| 7,799,492 | B2 | 9/2010 | Abe et al. |
| 8,021,764 | B2 | 9/2011 | Hwang et al. |
| 8,021,765 | B2 | 9/2011 | Hwang et al. |
| 8,188,315 | B2 | 5/2012 | Hwang et al. |
| 8,394,510 | B2 | 3/2013 | Mizuki et al. |
| 8,748,014 | B2 | 6/2014 | Yokoyama et al. |
| 8,845,926 | B2 | 9/2014 | Shitagaki et al. |
| 8,895,159 | B2 | 11/2014 | Mizuki et al. |
| 8,974,922 | B2 | 3/2015 | Hwang et al. |
| 9,123,897 | B2 | 9/2015 | Yokoyama et al. |
| 9,287,512 | B2 | 3/2016 | Ahn et al. |
| 9,478,754 | B2 | 10/2016 | Hwang et al. |
| 2007/0145888 | A1 | 6/2007 | Yabunouchi et al. |
| 2007/0252521 | A1 | 11/2007 | Kondakov et al. |
| 2012/0091887 | A1 | 4/2012 | Osaka et al. |
| 2012/0203010 | A1* | 8/2012 | Matsumoto .......... C07D 209/88 548/440 |
| 2014/0021451 | A1 | 1/2014 | Yokoyama et al. |
| 2014/0107338 | A1 | 4/2014 | Ahn et al. |
| 2014/0167026 | A1 | 6/2014 | Kato et al. |
| 2014/0353617 | A1* | 12/2014 | Kim ................... H01L 51/0054 257/40 |
| 2014/0374721 | A1 | 12/2014 | Yokoyama et al. |
| 2015/0171346 | A1 | 6/2015 | Ahn et al. |

FOREIGN PATENT DOCUMENTS

| | | |
|---|---|---|
| JP | 3194657 | 6/2001 |
| JP | 2004-311411 | 11/2004 |
| JP | 2005-108804 | 4/2005 |
| JP | 2006-151979 | 6/2006 |
| JP | 2007269738 A | 10/2007 |
| JP | 2007269738 A * | 10/2007 |
| JP | 2008-007424 | 1/2008 |
| JP | 2008-166538 | 7/2008 |
| JP | 2009-535815 | 10/2009 |
| JP | 2009-299049 | 12/2009 |
| JP | 4943840 | 5/2012 |
| JP | 2013-40105 | 2/2013 |
| JP | 2013-60411 | 4/2013 |
| JP | 2014-513064 | 5/2014 |
| KR | 2011-0018195 | 2/2011 |
| KR | 10-1216004 | 12/2012 |
| KR | 10-2013-0060157 | 6/2013 |
| TW | 201308707 A | 2/2013 |
| WO | 03/060956 | 7/2003 |
| WO | 2007/058127 | 5/2007 |
| WO | 2008/062636 | 5/2008 |
| WO | WO-2011/049123 A1 * | 4/2011 |
| WO | 2011/059000 | 5/2011 |
| WO | WO-2013011891 A1 * | 1/2013 |
| WO | 2013/054764 | 4/2013 |
| WO | 2014/061960 | 4/2014 |
| WO | WO-2014/163228 A1 * | 10/2014 |

OTHER PUBLICATIONS

Machine English translation of Wang et al. (JP 2008-166538 A). Jun. 30, 2018.*
Machine English translation of Nakano et al. (JP 2007-269738 A). Oct. 11, 2018.*
Machine English translation of Hyun et al. (WO-2014/163228 A1). Oct. 22, 2020.*
Endo et al., "Efficient up-conversion of triplet excitons into a singlet state and its application for organic light emitting diodes"; Applied Physics Letters, 98, 083302; Feb. 24, 2011; pp. 1-3.
International Search Report issued in Patent Application No. PCT/JP2015/071285, dated Oct. 13, 2015.
Extended European Search Report in respect to European Application No. 15827331.8, dated Feb. 12, 2018.
Chinese Office Action issued with respect to Japanese Application No. 201580052525.2, dated Nov. 26, 2018.
Taiwan Office Action, Taiwan Patent Office, Application No. 104124461, dated Jun. 12, 2019.

* cited by examiner

| | |
|---|---|
| 9 | CATHODE |
| 8 | ELECTRON INJECTION LAYER |
| 7 | ELECTRON TRANSPORT LAYER |
| 6 | LUMINOUS LAYER |
| 5b | SECOND HOLE TRANSPORT LAYER |
| 5a | FIRST HOLE TRANSPORT LAYER |
| 5 | HOLE TRANSPORT LAYER |
| 3 | HOLE INJECTION LAYER |
| 2 | TRANSPARENT ANODE |
| 1 | TRANSPARENT SUBSTRATE |

(1-6)　(1a-a)

(1-7)　(1a-a)

(1-8)　—

(1-9)　(1a-a)

(1-10)　(1a-a)

(1-11)　—

(1-25) (1a-a)

(1-26) (1a-a)

(1-27) (1c-a)

(1-28) (1a-a)

(1-29) (1c-b)

(1-30) (1c-a)

(1-31)   (1c-a)

(1-32)   (1c-a)

(1-33)   (1a-a)

(1-34)   (1a-a)

(1-35)   (1c-a)

(1-36)   (1c-a)

(1-37)  (1c-a)

(1-38)  (1b-a)

(1-39)  (1b-a)

(1-40)  (1a-b)

(1-41)  (1b-a)

(1-42)  (1b-a)

(1-43)　　(1a-b)

(1-44)　　(1a-b)

(1-45)　　(1a-a)

(1-46)　　(1c-b)

(1-47)　　(1a-b)

(1-48)　　(1c-b)

(1-54)  (1c-b)

(1-55)  (1c-b)

(1-56)  (1c-b)

(1-57)  (1c-b)

(1-58)  (1c-b)

(1-59)  (1c-b)

(1-60)  (1c-b)

(1-61)  (1c-b)

(1-62)  (1c-b)

(1-63)  (1c-b)

(1-64)  (1c-b)

(1-65)  (1c-b)

(1-66)  —

(1-67)  —

(1-68)  —

(1-69)

(1-70)

(1-71)

(1-72)

(1-73)

(1-74)

(1-75)

(1-76)

(1-77)

(1-78)

(1-79)

(1-80)

(2-1)  (2a)

(2-2)  (2a)

(2-3)  (2a)

(2-4)  (2a)

(2-5)  (2b)

(2-6)  (2b)

(2-13) —

(2-14) (2d)

(2-15) (2e)

(3-1)    (3a-1)

(3-2)    (3a-1)

(3-3)    (3a-1)

(3-4)    (3a-1)

(3-5)    (3a-1)

(3-6)    (3a-1)

(3-14)　　(3a-2)

(3-15)　　(3a-1)

(3-16)　　—

(3-17)　　—

(3-18)　　—

(3-19)　　—

(3-20)

(3-21)

(3-22)

(3-23)

(4-1)　(4a)(4c)

(4-2)　(4a)(4c)

(4-3)　(4b)(4d)

(4-4)　(4a)(4c)

(4-5)　(4a)(4d)

(4-6)　(4a)(4c)

(4-7)　(4a)(4d)

(4-8)  (4b) (4c)

(4-9)  (4a) (4c)

(4-10)  (4a) (4c)

(4-11)  (4a) (4c)

(4-12)  (4a) (4c)

(4-13)  (4a) (4c)

(4-14)  (4a) (4c)

(4-15)  (4a) (4c)

(4-16)  (4a) (4c)

(4-17)  (4a) (4c)

(4-18)  (4a) (4c)

(4-19)  (4a) (4c)

(4-20)  (4a) (4c)

(5a-1) (5a')

(5a-2) (5a')

(5a-3) (5a')

(5a-4) (5a')

(5a-5) (5a')

(5a-6) (5a')

(5a-7)  (5a´)

(5a-8)  (5a´)

(5a-9)  (5a´)

(5a-10)  (5a´)

(5a-11)  (5a´)

(5a-18)

(5a-19)

(5a-20)

(5b-1)

(5b-2)

(5b-3)

(5b-4)

(5b-5)

(5b-6)

(5b-7)

(5b-8)

(5b-9)

(5b-10)

(5b-11)

(5b-12)

(5b-13)

(5b-14)

(5b-15)

(5b-16)

(5c-1)

(5c-2)

(5c-3)

(5c-4)

(5c-5)

(5c-6)

(5c-7)

(5c-8)

(5c-9)

(5c-10)

(5c-11)

(5c-12)

(5c-13)

(5c-14)

(5c-15)

(5c-16)

(5c-17)

(5c-18)

(5c-19)

(5c-20)

(5c-21)

(5c-22)

(5c-23)

(5c-24)

(5c-25)

(5c-26)

(5c-27)

(5c-28)

(5c-29)

(5c-30)

(6-19)

(6-20)

(6-21)

(6-22)

(6-23)

(6'-1)

(6'-2)

(7-1)

(7-2)

(7-3)

(7-4)

(7-5)

(7-6)

(7-7)

(7-8)

(7-9)

(7-10)

(7-11)

(7-12)

(7-13)

(7-14)

(7-15)

(7-16)

(7-17)

ORGANIC ELECTROLUMINESCENCE DEVICE

TECHNICAL FIELD

The present invention relates to an organic electroluminescence device which is a self light-emitting device (can be referred to hereinbelow as "organic EL device") advantageously suitable for various display devices, and more specifically to an organic EL device using a specific arylamine compound and a heterocyclic compound having a specific condensed ring structure (and a specific benzotriazole derivative or a specific anthracene derivative).

BACKGROUND ART

An organic EL device is a self light-emitting device, and is thus brighter, better in visibility, and capable of clearer display, than a liquid crystal device. Hence, active researches have been conducted on organic EL devices.

In 1987, C. W. Tang et al. of Eastman Kodak Company developed a laminated structure device sharing various roles among different materials, thereby imparting practical applicability to organic EL devices using organic materials. The developed organic EL device is configured by laminating a layer of a fluorescent body capable of transporting electrons, and a layer of an organic substance capable of transporting holes. As a result of injecting positive charges and negative charges into the layer of the fluorescent body to perform light emission, it is possible to obtain a high luminance of 1000 cd/m$^2$ or higher at a voltage of 10 V or less (see Patent Document 1 and Patent Document 2).

Many improvements have been heretofore made to put the organic EL devices to practical use. For example, it is generally well known that high efficiency and durability can be achieved with a field emission device in which roles to be played by respective layers of the laminated structure are further segmented for each layer and an anode, a hole injection layer, a hole transport layer, a luminous layer, an electron transport layer, an electron injection layer, and a cathode are provided in the order of description on a substrate.

For further increase in the luminous efficiency, it has been attempted to utilize triplet excitons, and the utilization of phosphorescent luminous compounds has been investigated.

Furthermore, devices utilizing light emission by thermally activated delayed fluorescence (TADF) have been developed. In 2011, Adachi et al. from Kyushu University have realized an external quantum efficiency of 5.3% with a device using a thermally activated delayed fluorescence material.

The luminous layer can also be prepared by doping a charge transporting compound, generally called a host material, with a fluorescent compound, a phosphorescent luminous compound, or a material radiating delayed fluorescence. The selection of the organic material in the organic EL device greatly affects the characteristics of the device, such as efficiency and durability.

With the organic EL device, the charges injected from both electrodes recombine in the luminous layer, thereby producing light emission, and how efficiently the charges of the holes and the electrons are passed on to the luminous layer is of importance and a device that exhibits excellent carrier balance is required. Further, by enhancing hole injection property or increasing electron blocking property, that is, property to block electrons injected from the cathode, it is possible to increase the probability of holes and electrons recombining, and by further confining the excitons generated in the luminous layer, it is possible to obtain a high luminous efficiency. Therefore, the role of the hole transport material is important, and a demand has been created for a hole transport material having high hole injection property, high hole mobility, high electron blocking property, and high durability to electrons.

From the viewpoint of device life, heat resistance or amorphousness of the materials are also important. A material with a low heat resistance is thermally decomposed even at a low temperature by heat produced during device driving, and the material deteriorates. In a material with low amorphousness, crystallization of a thin film occurs even in a short time, and the device deteriorates. Thus, high heat resistance and satisfactory amorphousness are required of the materials to be used.

N,N'-diphenyl-N,N'-di(α-naphthyl)benzidine (NPD) and various aromatic amine derivatives are known as hole transport materials which have been heretofore used in organic EL devices (see Patent Document 1 and Patent Document 2). NPD has satisfactory hole transport capacity, but the glass transition point (Tg), which is an indicator of heat resistance, is as low as 96° C. and device characteristics degraded due to crystallization under high-temperature conditions.

Further, among the aromatic amine derivatives disclosed in Patent Documents 1 and 2, there are also compounds with an excellent hole mobility of 10$^{-3}$ cm$^2$/Vs or higher, but, for instance, since electron blocking property is insufficient, some of electrons pass through the luminous layer, and no increase in luminous efficiency can be expected. Thus, materials with better electron blocking property, higher stability, and high heat resistance in a thin film are needed to increase further the efficiency.

An aromatic amine derivative with high durability has also been reported (see Patent Document 3), but this derivative was used as a charge transport material for use in an electrophotographic photosensitive body and there is no example of application to an organic EL device.

Arylamine compounds having a substituted carbazole structure have been suggested as compounds with improved properties such as heat resistance and hole injection property (see Patent Document 4 and Patent Document 5), but although heat resistance, luminous efficiency, and the like of devices using these compounds for a hole injection layer or hole transport layer have been improved, the results are still insufficient and further decrease in a driving voltage and increase in luminous efficiency are needed.

Devices in which holes and electrons can recombine with a high efficiency and which have a high luminous efficiency, a low driving voltage, and a long life need to be provided by combining materials with excellent hole and electron injection-transport performance and stability and durability of a thin film so as to improve device characteristics of organic EL devices and increase the yield in device production.

Further, devices which are balanced in carriers and have a high efficiency, a low driving voltage, and a long life need to be provided by combining materials with excellent hole and electron injection-transport performance and stability and durability of a thin film so as to improve device characteristics of organic EL devices.

PRIOR ART DOCUMENTS

Patent Documents

Patent Document 1: JP-A-8-048656
Patent Document 2: Japanese Patent No. 3194657

Patent Document 3: Japanese Patent No. 4943840
Patent Document 4: JP-A-2006-151979
Patent Document 5: WO2008/62636
Patent Document 6: JP-A-2014-513064
Patent Document 7: WO2013/054764
Patent Document 8: WO2011/059000
Patent Document 9: WO2003/060956
Patent Document 10: KR-A-2013-060157
Patent Document 11: JP-A-7-126615
Patent Document 12: JP-A-2005-108804

Non Patent Documents

Non Patent Document 1: Appl. Phys. Let., 98, 083302 (2011)

SUMMARY OF THE INVENTION

Problems to be Solved by the Invention

It is an object of the present invention to provide an organic EL device which has a high efficiency, a low driving voltage, and a long life by combining materials for an organic EL device with excellent hole and electron injection-transport performance, electron blocking capacity, and stability and durability in a thin-film state so as to demonstrate effectively the properties possessed by each material.

Means for Solving the Problems

To attain the above object, the inventors of the present invention noted that arylamine-based materials have excellent hole injection and transport capacity and stability and durability of a thin film, that nitrogen-containing heterocyclic compounds having a condensed ring structure (in particular, indenoindole derivatives and carbazole derivatives) have excellent luminous efficiency, and that benzotriazole derivatives and anthracene derivatives have excellent electron injection and transport capacity and stability and durability of a thin film. Accordingly, the inventors selected a specific arylamine compound and a specific indenoindole derivative or a specific carbazole derivative to enable efficient injection and transport of holes to the luminous layer, achieved a favorable carrier balance suitable for properties of luminous layer materials, produced various organic EL devices including combinations of hole transport materials and materials for the luminous layer, and performed comprehensive property evaluation of the devices. Further, various organic EL devices including combinations of hole transport materials, materials for the luminous layer, and electron transport materials were also produced such as to increase also the electron injection and transport efficiency to the luminous layer and match carrier balance with properties of the material of the luminous layer, and extensive property evaluation of the devices was performed. Further, the hole transport layer was configured as a two-layer structure including a first hole transport layer and a second hole transport layer, a specific arylamine derivative was selected as a material for the first hole transport layer such as to enable efficient injection and transport of holes to the luminous layer, another arylamine derivative which excels in electron blocking property was selected as a material for the second hole transport layer, various organic EL devices with refined combinations that ensure carrier balance were produced, and extensive property evaluation of the devices was performed. As a result, the inventors have accomplished the present invention.

According to the present invention, there is provided an organic EL device having an anode, a hole transport layer, a luminous layer, an electron transport layer, and a cathode in order of description, wherein
the hole transport layer includes an arylamine compound represented by the following general formula (1); and
the luminous layer includes an indenoindole derivative represented by the following general formula (2) or a carbazole derivative represented by the following general formula (3):

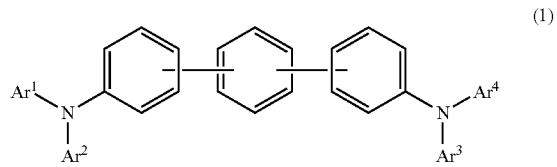

wherein,
$Ar^1$ to $Ar^4$ each represent an aromatic hydrocarbon group or an aromatic heterocyclic group;

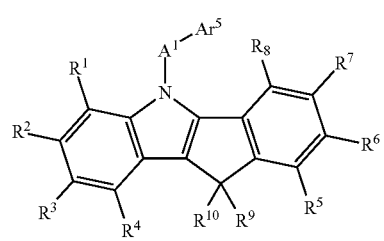

wherein,
$A^1$ represents a divalent group of an aromatic hydrocarbon, a divalent group of an aromatic heteroclic ring, or a single bond;
$Ar^5$ represents an aromatic hydrocarbon group or an aromatic heterocyclic group;
$R^1$ to $R^8$ each represent a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, an aryloxy group, or a disubstituted amino group having an aromatic hydrocarbon group or an aromatic heterocyclic group as a substituent;
respective groups among $R^1$ to $R^4$ may be bonded to each other via a single bond, a substituted or unsubstituted methylene group, an oxygen atom, or a sulfur atom to form a ring;
respective groups among $R^5$ to $R^8$ may be bonded to each other via a single bond, a substituted or unsubstituted methylene group, an oxygen atom, or a sulfur atom to form a ring;
some of $R^1$ to $R^4$ may be detached and the remaining groups of $R^1$ to $R^4$ may be bonded to vacancies generated by the detachment via a substituted or unsubstituted methylene group, an oxygen atom, a sulfur atom, or a monoarylamino group to form a ring;
some of $R^5$ to $R^9$ may be detached and the remaining groups of $R^5$ to $R^8$ may be bonded to vacancies generated by the detachment via a substituted or unsubstituted methylene group, an oxygen atom, a sulfur atom, or a monoarylamino group to form a ring; and $R^9$ and $R^{10}$ are each an alkyl group having 1 to 6 carbon atoms, an aromatic hydrocarbon group, or an aromatic heterocyclic group and may be bonded to each other via a single bond, a substituted or unsubstituted methylene group, an oxygen atom, or a sulfur atom to form a ring;

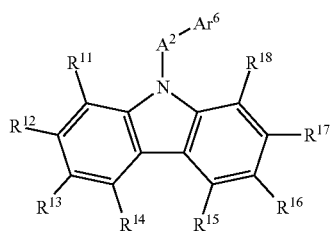

(3)

wherein, $A^2$ represents a divalent group of an aromatic hydrocarbon, a divalent group of an aromatic heteroclic ring, or a single bond;

$Ar^6$ represents an aromatic hydrocarbon group or an aromatic heterocyclic group;

$R^{11}$ to $R^{18}$ each represent a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, an aryloxy group, or a disubstituted amino group having an aromatic hydrocarbon group or an aromatic heterocyclic group as a substituent;

respective groups among $R^{11}$ to $R^{14}$ may be bonded to each other via a single bond, a substituted or unsubstituted methylene group, an oxygen atom, or a sulfur atom to form a ring;

respective groups among $R^{15}$ to $R^{18}$ may be bonded to each other via a single bond, a substituted or unsubstituted methylene group, an oxygen atom, or a sulfur atom to form a ring;

some of $R^{11}$ to $R^{14}$ may be detached and the remaining groups of $R^{11}$ to $R^{14}$ may be bonded to vacancies generated by the detachment via a substituted or unsubstituted methylene group, an oxygen atom, a sulfur atom, or a monoarylamino group to form a ring; and some of $R^{15}$ to $R^{18}$ may be detached and the remaining groups of $R^{15}$ to $R^{18}$ may be bonded to vacancies generated by the detachment via a substituted or unsubstituted methylene group, an oxygen atom, a sulfur atom, or a monoarylamino group to form a ring.

In the organic EL device of the present invention, it is preferred that:

(1) the electron transport layer include a benzotriazole derivative represented by the following general formula (4):

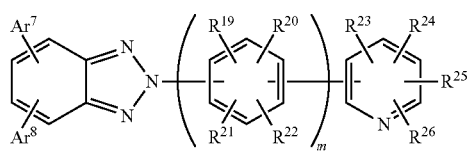

(4)

wherein, $Ar^7$ represents an aromatic hydrocarbon group or an aromatic heterocyclic group;

$Ar^8$ represents a hydrogen atom, a deuterium atom, an aromatic hydrocarbon group or an aromatic heterocyclic group;

$R^{19}$ to $R^{26}$ each represent a hydrogen atom, a deuterium atom, a fluorine atom, a chlorine atom, a cyano group, an alkyl group having 1 to 6 carbon atoms, an aromatic hydrocarbon group, or an aromatic heterocyclic group;

m represents an integer of 0 to 2;

when m is 2, a plurality of existing $R^{19}$, $R^{20}$, $R^{21}$, and $R^{22}$ may be the same or different;

(2) the electron transport layer include an anthracene derivative represented by the following general formula (5):

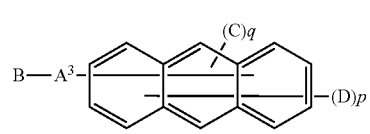

(5)

wherein, in p and q, p is an integer of 7 or 8 and q is an integer of 1 or 2 such that a sum of p and q being 9 is maintained;

$A^3$ represents a divalent group of an aromatic hydrocarbon, a divalent group of an aromatic heteroclic ring, or a single bond;

B represents an aromatic heterocyclic group;

C represents an aromatic hydrocarbon group or an aromatic heterocyclic group; when q is 2, a plurality of existing C may be the same or different; and D represents a hydrogen atom, a deuterium atom, a fluorine atom, a chlorine atom, a cyano group, or an alkyl group having 1 to 6 carbon atoms, and a plurality of existing D may be the same or different;

(3) the anthracene derivative be represented by the following general formula (5a), (5b), or (5c):

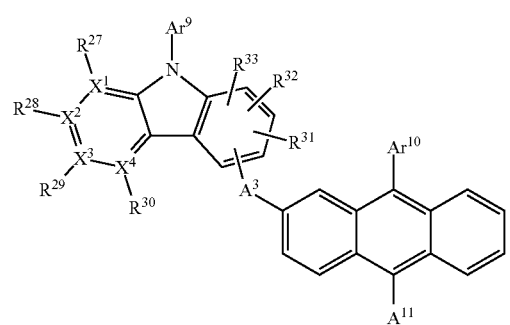

(5a)

wherein, $A^3$ has the same meaning as that defined in the general formula (5);

$Ar^9$ to $Ar^{11}$ each represent an aromatic hydrocarbon group or an aromatic heterocyclic group;

$R^{27}$ to $R^{33}$ are each a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, or an aryloxy group and may be bonded to each other via a single bond, a substituted or unsubstituted methylene group, an oxygen atom, or a sulfur atom to form a ring; and $X^1$ to $X^4$ represent a carbon atom or a nitrogen atom, only any one of $X^1$ to $X^4$ is a nitrogen atom, and none of $R^{27}$ to $R^{30}$, including a hydrogen atom, is bonded to the nitrogen atom;

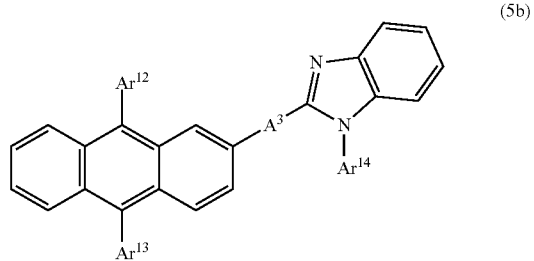

(5b)

wherein, $A^3$ has the same meaning as that defined in the general formula (5);

$Ar^{12}$ to $Ar^{14}$ each represent an aromatic hydrocarbon group or an aromatic heterocyclic group;

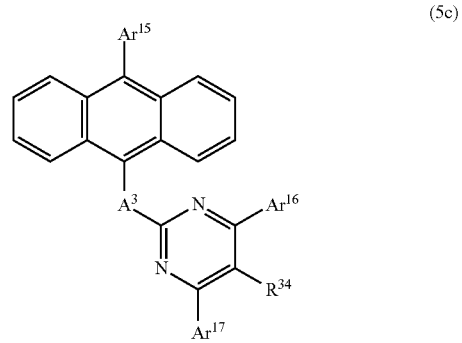

(5c)

wherein, $A^3$ has the same meaning as that defined in the aforementioned general formula (5);

$Ar^{15}$ to $Ar^{17}$ each represent an aromatic hydrocarbon group or an aromatic heterocyclic group; and $R^{34}$ represents a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, or an aryloxy group;

(4) the hole transport layer have a two-layer structure including a first hole transport layer and a second hole transport layer, and the second hole transport layer be positioned on the luminous layer side and include an arylamine compound represented by the general formula (1);

(5) the luminous layer include a phosphorescence emitting material;

(6) the phosphorescence emitting material be a metal complex including iridium or platinum; and (7) the phosphorescence emitting material be a red luminous dopant.

Effects of the Invention

In the organic EL device of the present invention, a specific arylamine compound that excels in hole injection and transport performance and stability and durability of a thin film and can effectively demonstrate the hole injection and transport is selected as a material of the hole transport layer. For this reason, in the present invention, an organic EL device is realized in which holes can be effectively injected and transported to the luminous layer and which has a high efficiency, a low driving voltage, and a long life. Further, as a result of selecting a specific electron transport material such that carrier balance is achieved that matches the properties of the material of the luminous layer having a specific structure, in addition to selecting the specific arylamine compound as the hole transport material, an organic EL device is realized which has a high efficiency and a low driving voltage and also a particularly long life. Furthermore, when the hole transport layer is configured to have a two-layer structure including a first hole transport layer and a second hole transport layer, an organic EL device with an increased luminous efficiency, a decreased driving voltage, and a longer life is realized by combining two arylamine derivatives having specific structures, while taking into account the carrier balance and material properties. Thus, in the organic EL device of the present invention, the hole transport efficiency from the hole transport layer into the luminous layer is increased and the electron transport efficiency from the electron transport layer into the luminous layer is also increased as compared with those of the conventional organic EL devices.

MODE FOR CARRYING OUT THE INVENTION

The organic EL device of the present invention has a basic structure in which an anode, a hole transport layer, a luminous layer, an electron transport layer, and a cathode are formed, in the order of description, on a transparent substrate such as a glass substrate or a transparent plastic substrate (for example, a polyethylene terephthalate substrate). The layered structure can be in various forms, provided that it has such a basic structure. For example, each layer may have a single-layer structure or a laminated structure. In particular, the hole transport layer can have a two-layer structure including a first hole transport layer positioned on the anode side and a second hole transport layer adjacent to the luminous layer. A hole injection layer can be provided between the transparent electrode and the hole transport layer, and an electron infection layer can be provided between the electron transport layer and the cathode. Furthermore, one material or a combination of two or more materials may be used to form each layer.

Figure 1:
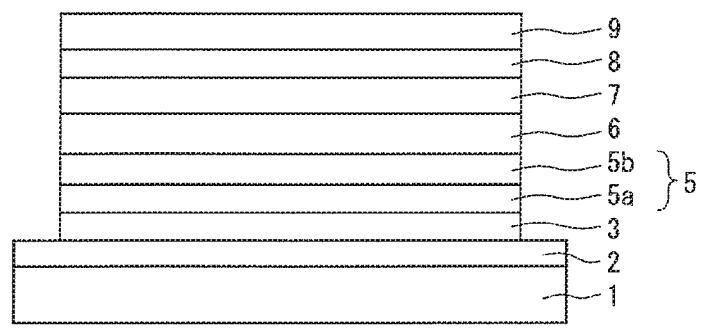
[FIG. 1] is a view showing the configuration of the organic EL devices of Examples 43-68 and Comparative Examples 1-5.
Figure 2:
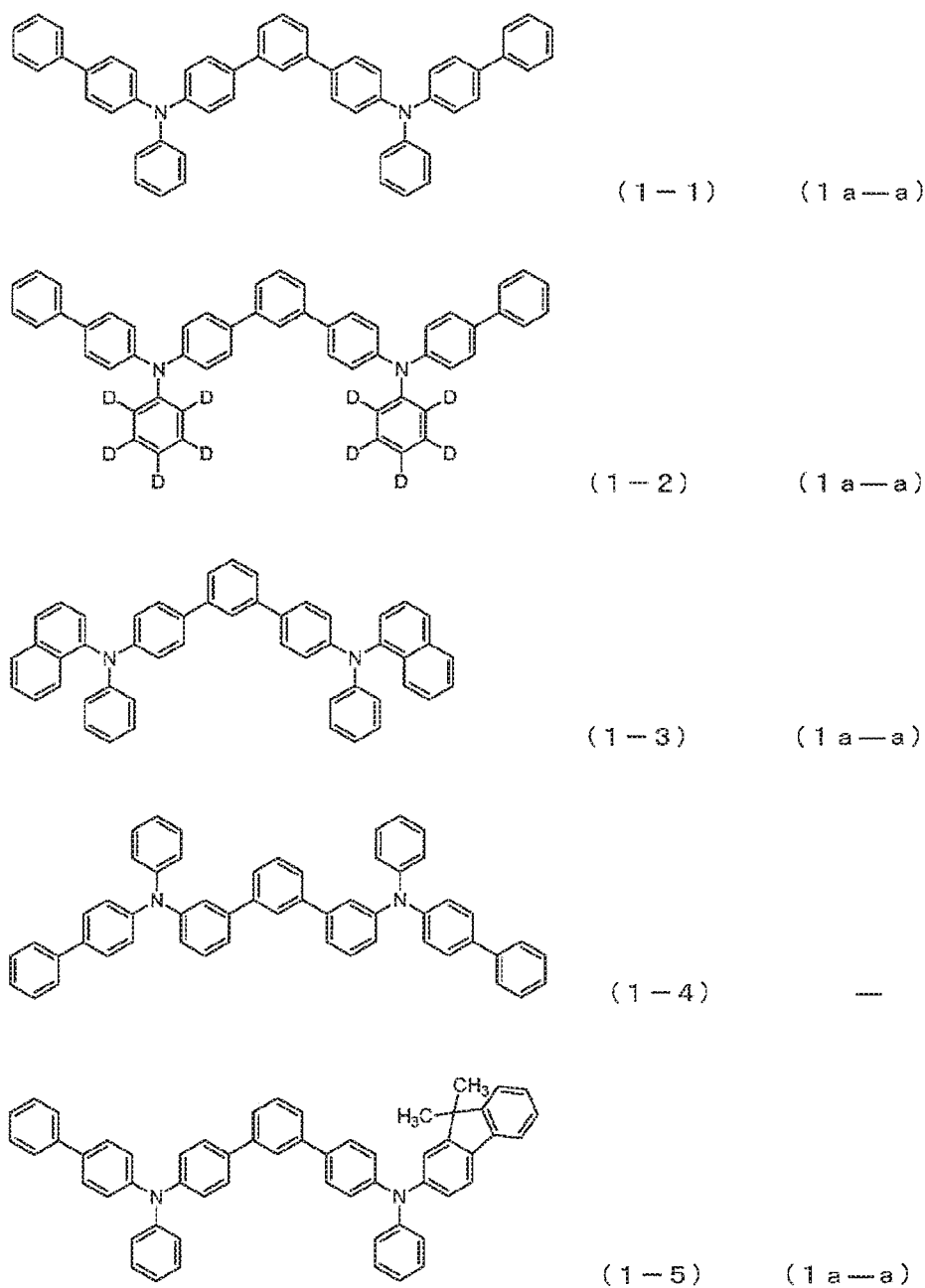
[FIG. 2] is a view showing the structural formulas of Compounds (1-1) to (1-5) in the arylamine compound of the general formula (1).
Figure 3:
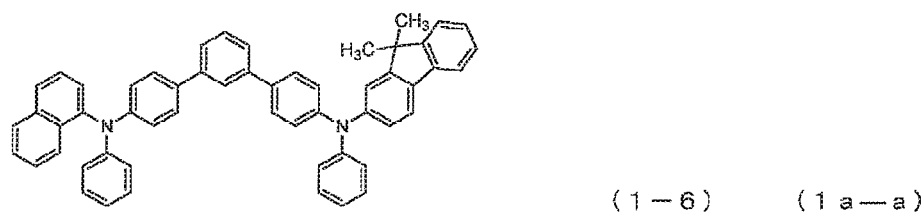
[FIG. 3] is a view showing the structural formulas of Compounds (1-6) to (1-11) in the arylamine compound of the general formula (1).
Figure 3:
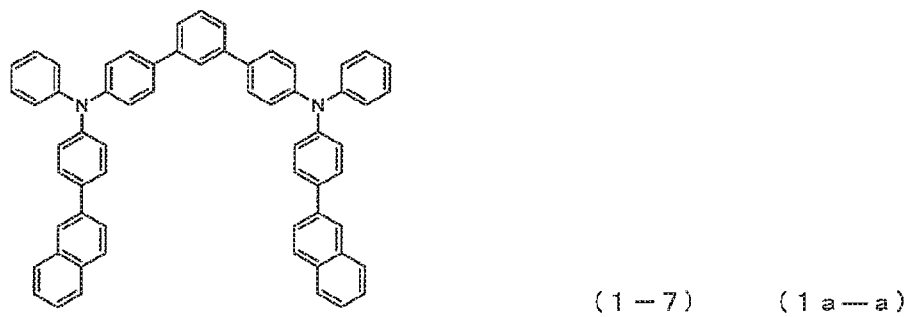
Figure 3:
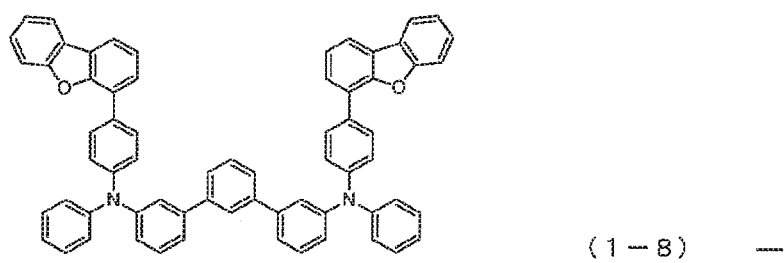
Figure 3:
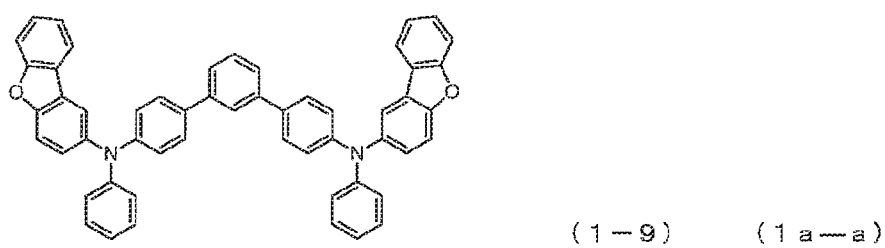
Figure 3:
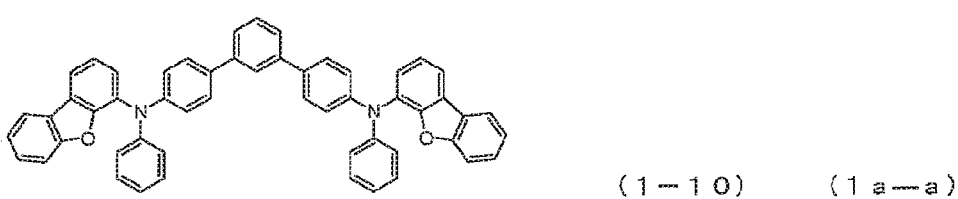
Figure 3:
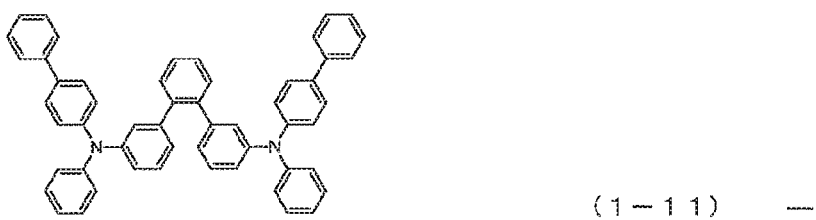
Figure 4:
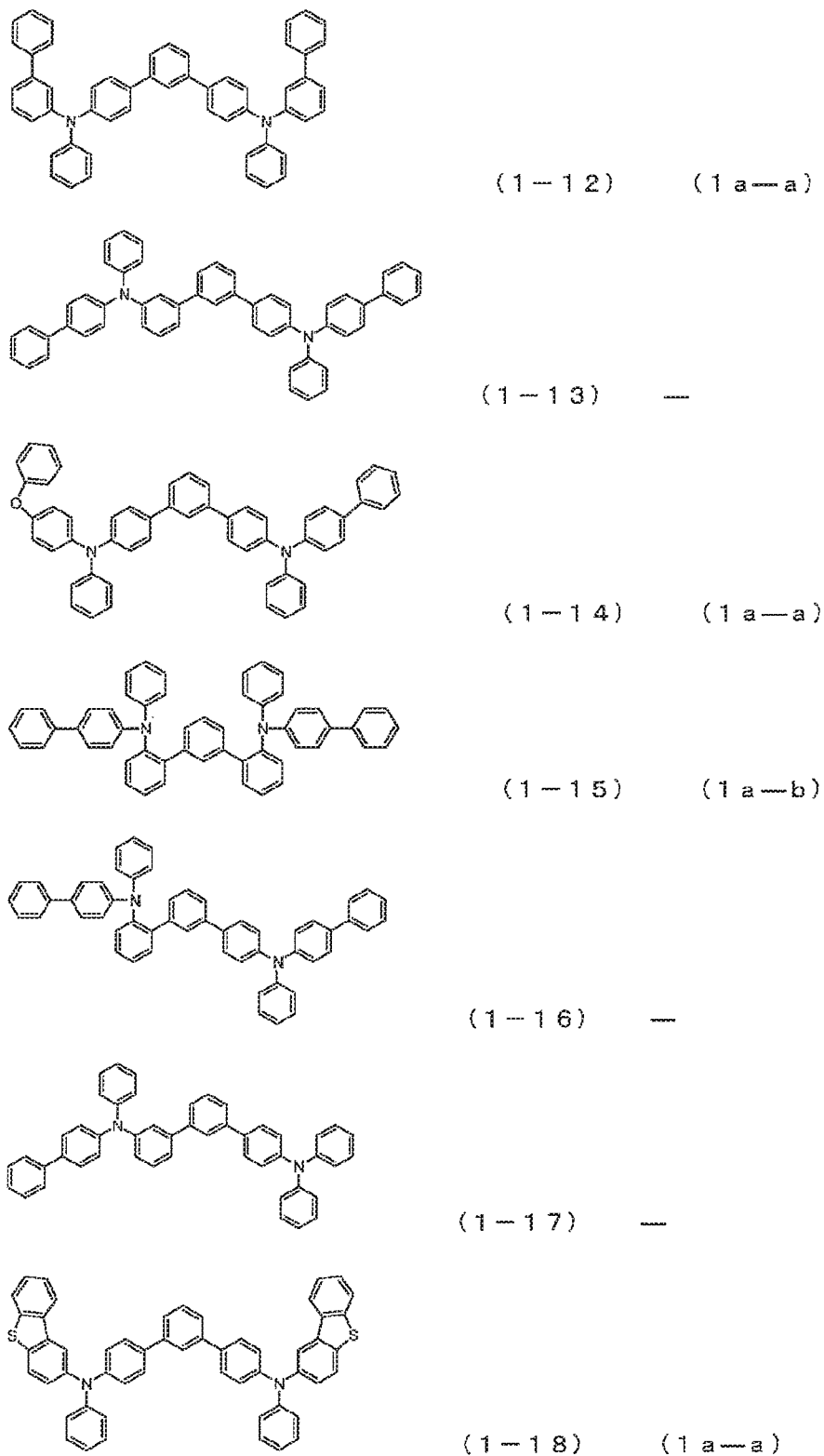
[FIG. 4] is a view showing the structural formulas of Compounds (1-12) to (1-18) in the arylamine compound of the general formula (1).
Figure 5:
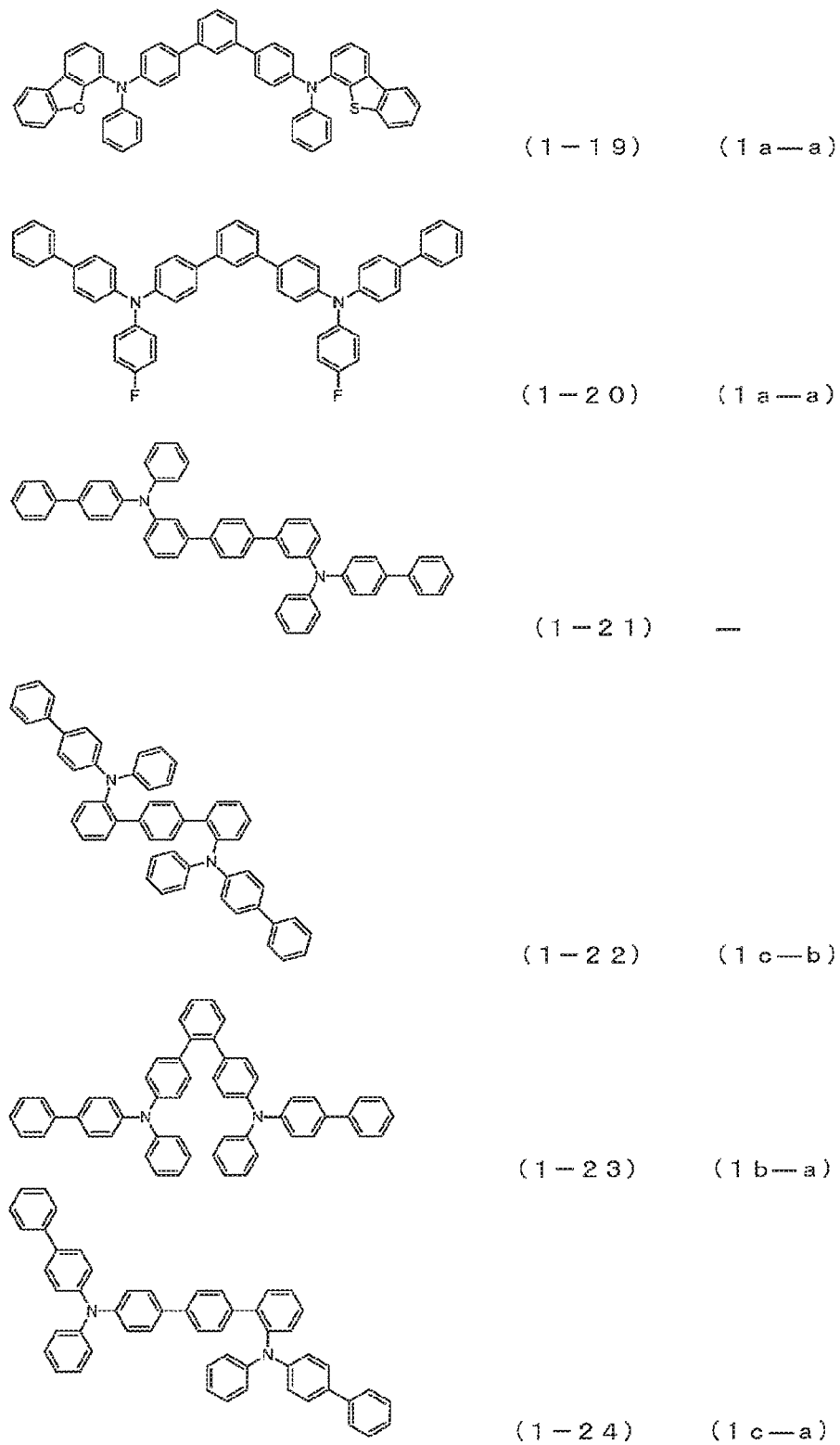
[FIG. 5] is a view showing the structural formulas of Compounds (1-19) to (1-24) in the arylamine compound of the general formula (1).
Figure 6:
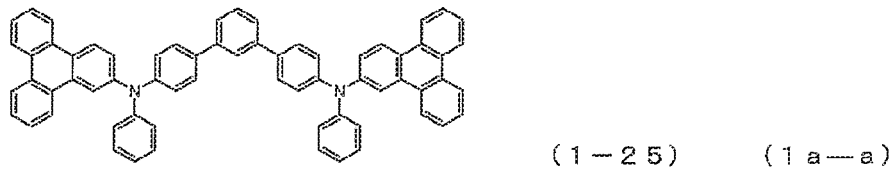
[FIG. 6] is a view showing the structural formulas of Compounds (1-25) to (1-30) in the arylamine compound of the general formula (1).
Figure 6:
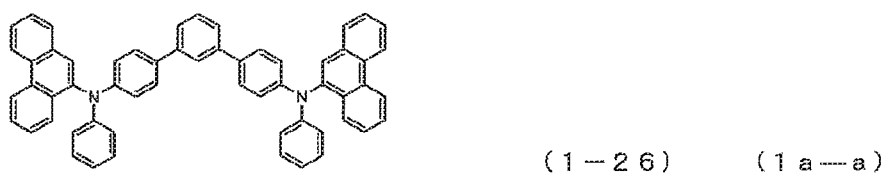
Figure 6:
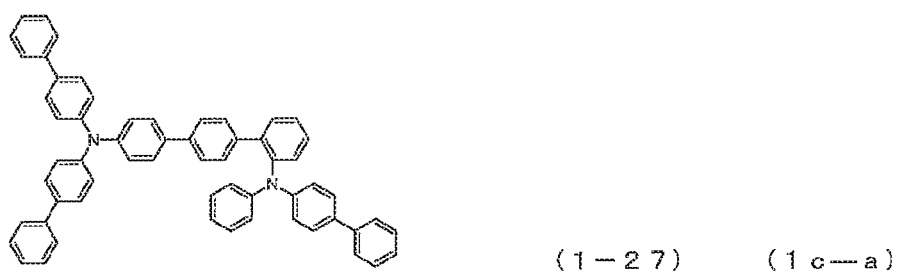
Figure 6:
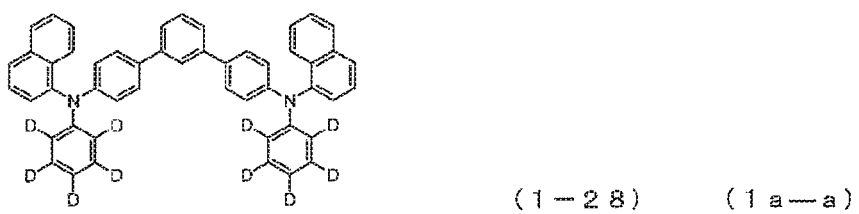
Figure 6:
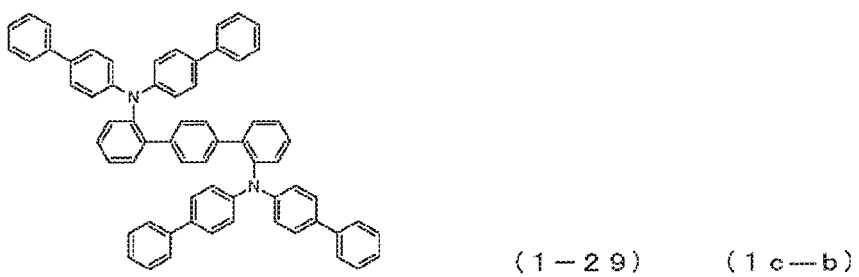
Figure 6:
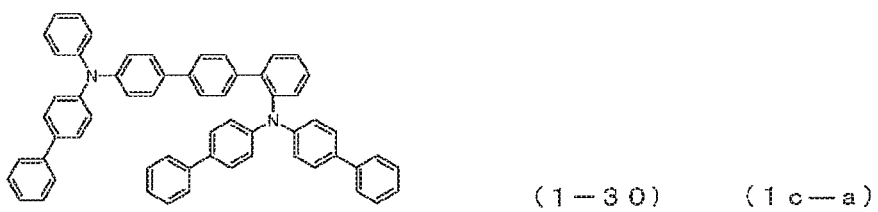
Figure 7:
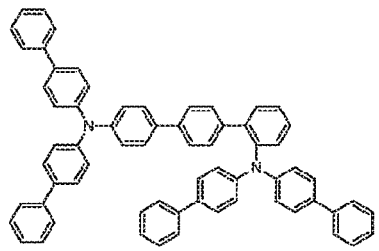
[FIG. 7] is a view showing the structural formulas of Compounds (1-31) to (1-36) in the arylamine compound of the general formula (1).
Figure 7:
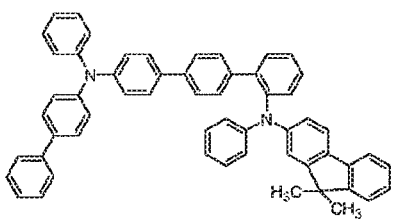
Figure 7:
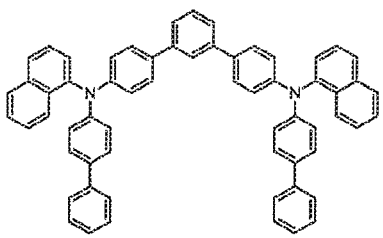
Figure 7:
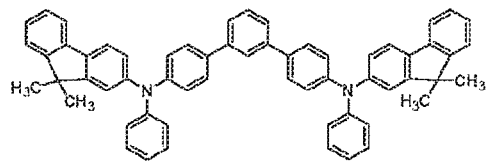
Figure 7:
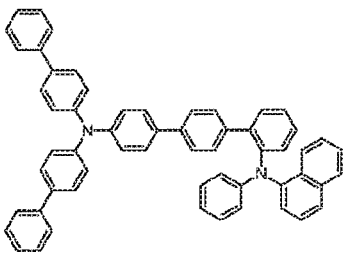
Figure 7:
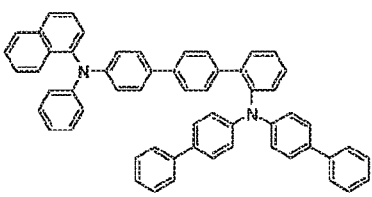
Figure 8:
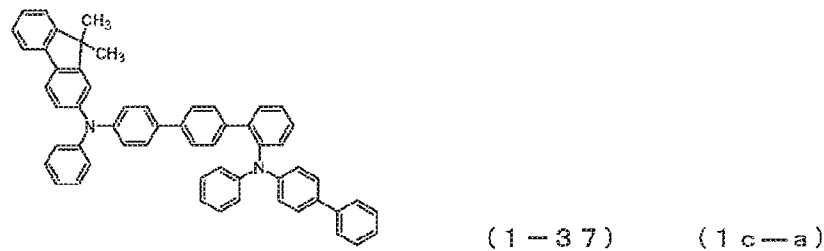
[FIG. 8] is a view showing the structural formulas of Compounds (1-37) to (1-42) in the arylamine compound of the general formula (1).
Figure 8:
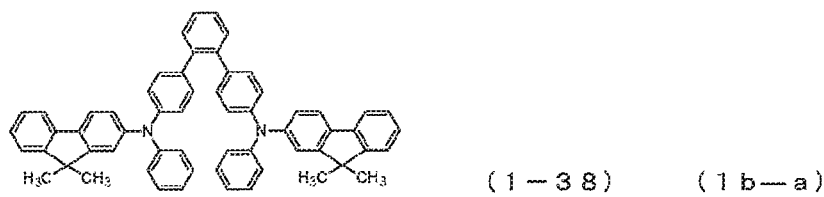
Figure 8:
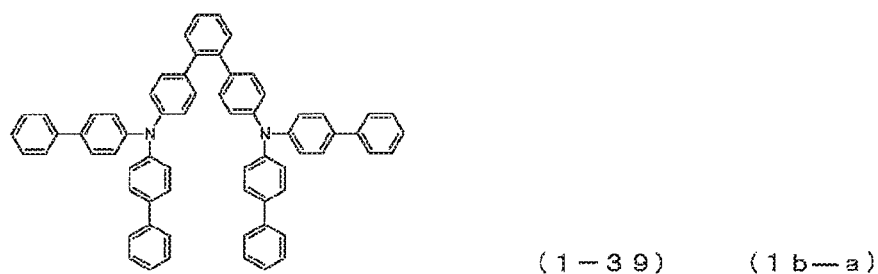
Figure 8:
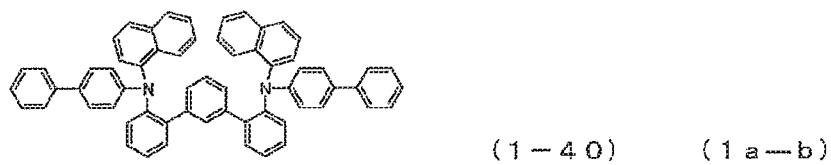
Figure 8:
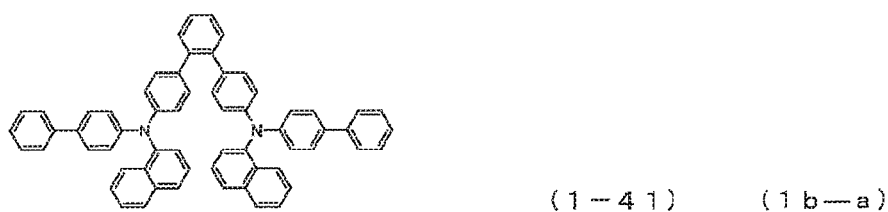
Figure 8:
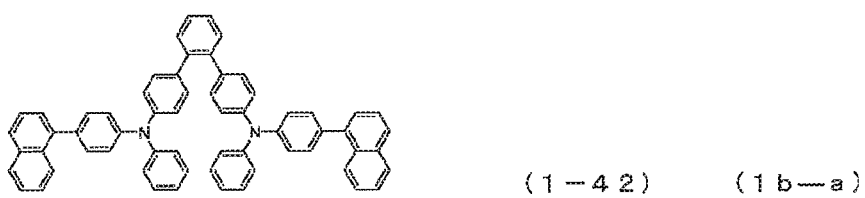
Figure 9:
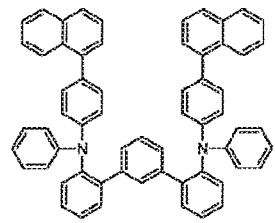
[FIG. 9] is a view showing the structural formulas of Compounds (1-43) to (1-48) in the arylamine compound of the general formula (1).
Figure 9:
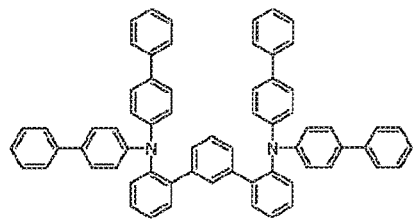
Figure 9:
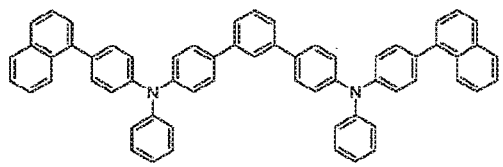
Figure 9:
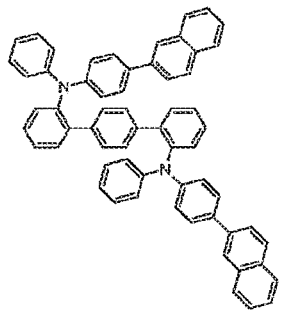
Figure 9:
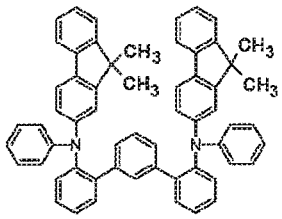
Figure 9:
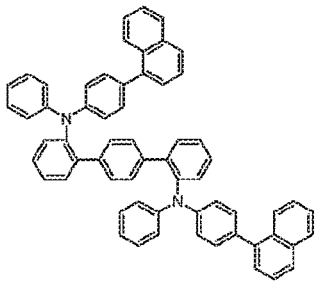
Figure 10:
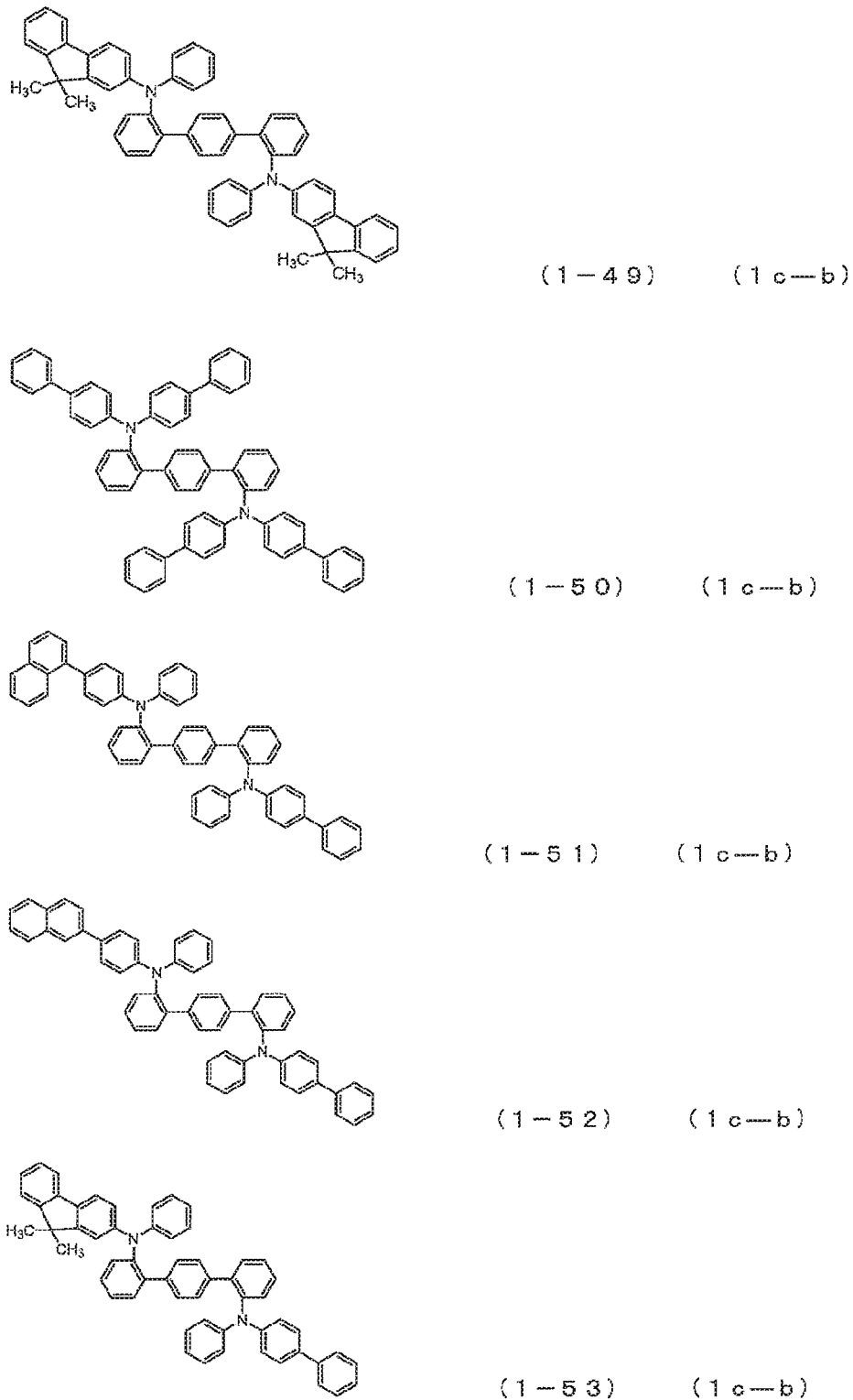
[FIG. 10] is a view showing the structural formulas of Compounds (1-49) to (1-53) in the arylamine compound of the general formula (1).
Figure 11:
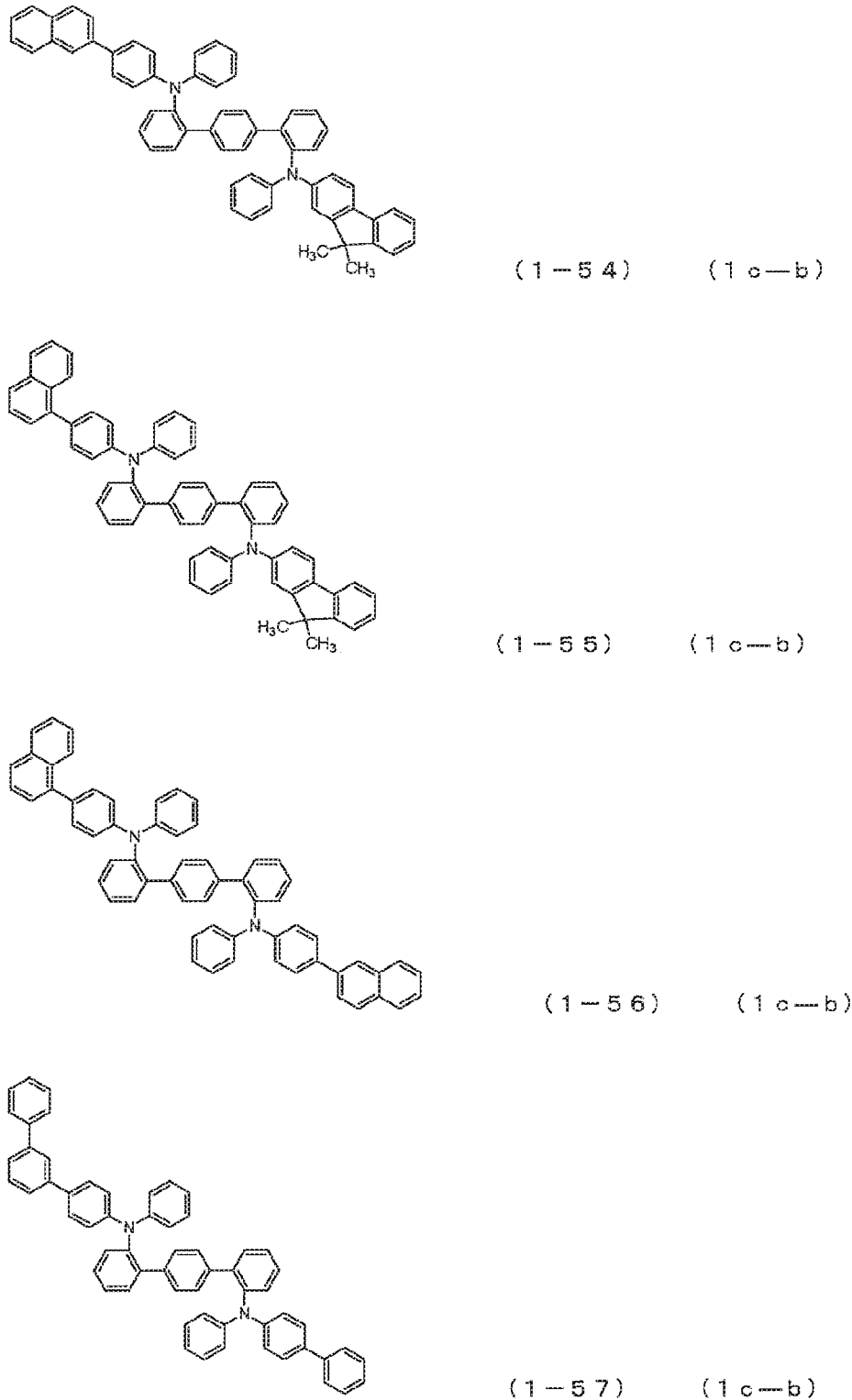
[FIG. 11] is a view showing the structural formulas of Compounds (1-54) to (1-57) in the arylamine compound of the general formula (1).
Figure 12:
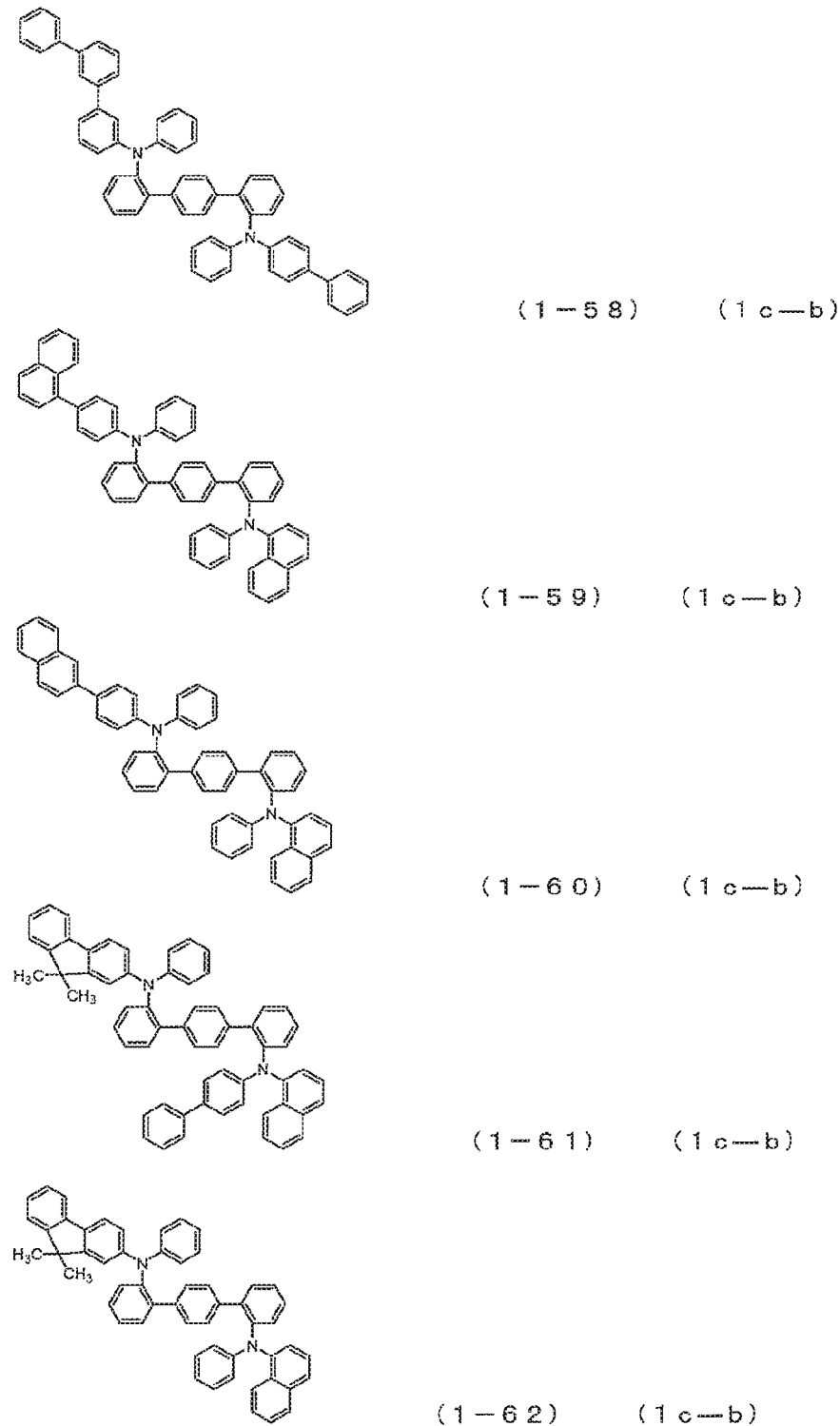
[FIG. 12] is a view showing the structural formulas of Compounds (1-58) to (1-62) in the arylamine compound of the general formula (1).
Figure 13:
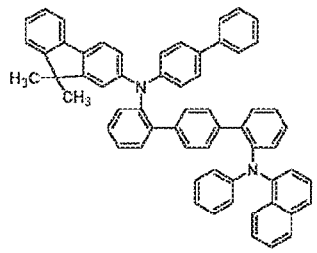
[FIG. 13] is a view showing the structural formulas of Compounds (1-63) to (1-68) in the arylamine compound of the general formula (1).
Figure 13:
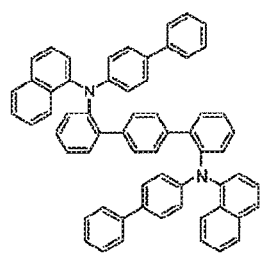
Figure 13:
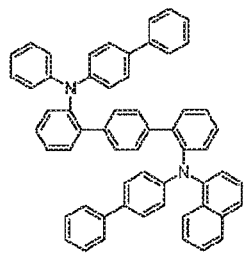
Figure 13:
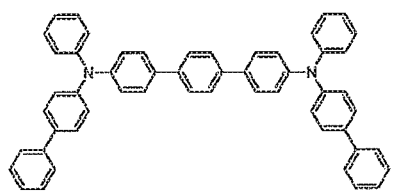
Figure 13:
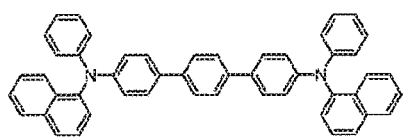
Figure 13:
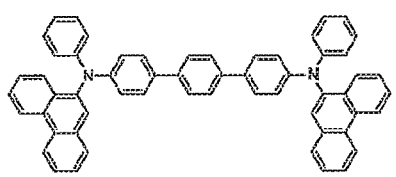
Figure 14:
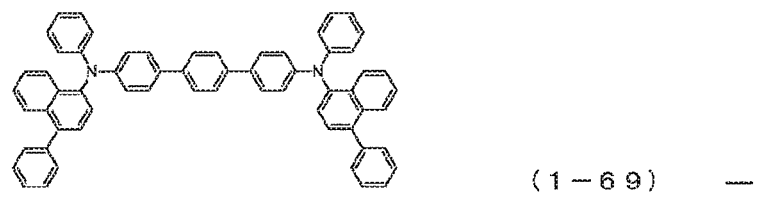
[FIG. 14] is a view showing the structural formulas of Compounds (1-69) to (1-75) in the arylamine compound of the general formula (1).
Figure 14:
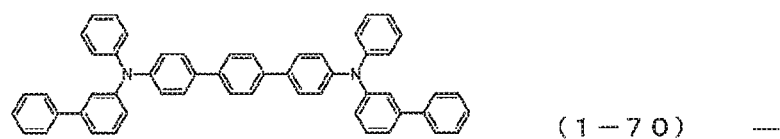
Figure 14:
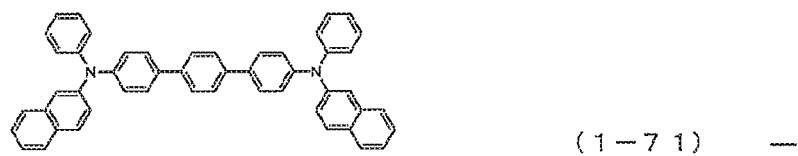
Figure 14:
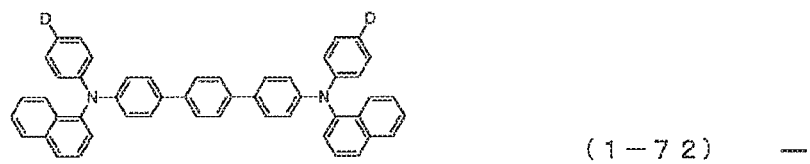
Figure 14:
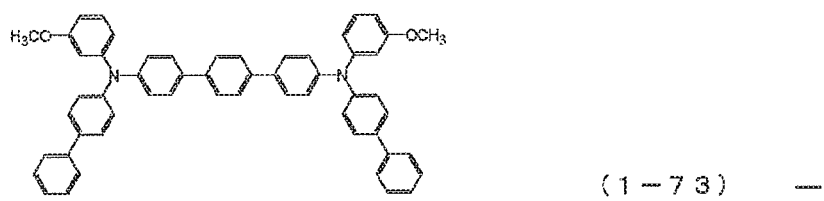
Figure 14:
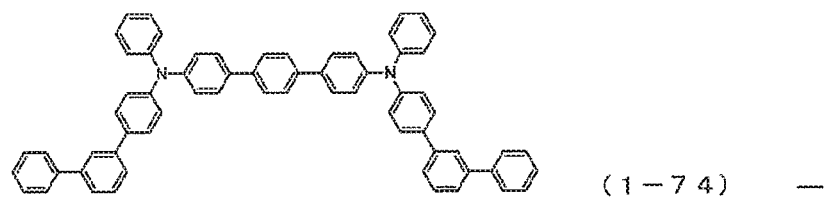
Figure 14:
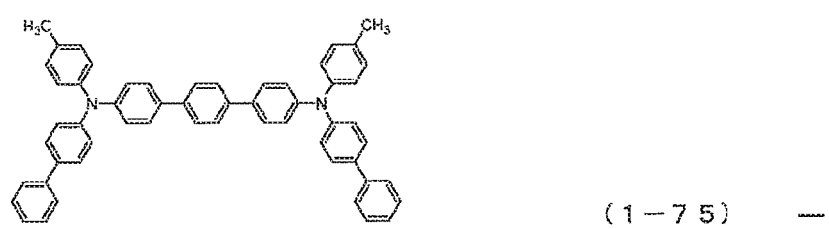
Figure 15:
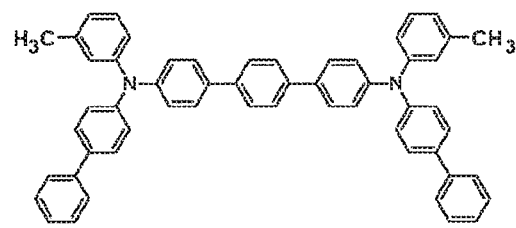
[FIG. 15] is a view showing the structural formulas of Compounds (1-76) to (1-80) in the arylamine compound of the general formula (1).
Figure 15:
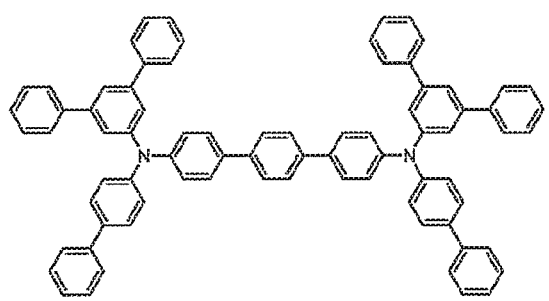
Figure 15:
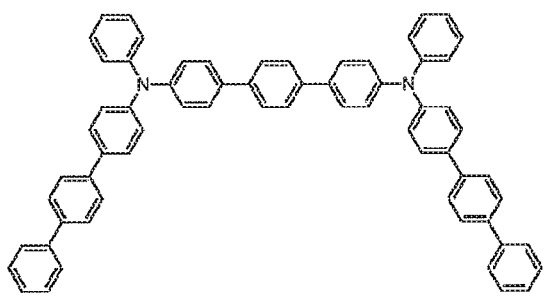
Figure 15:
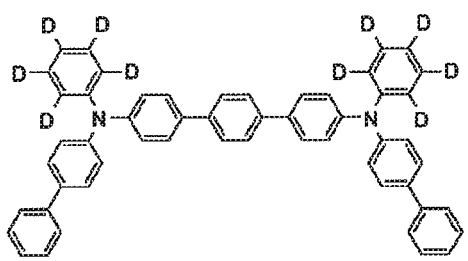
Figure 15:
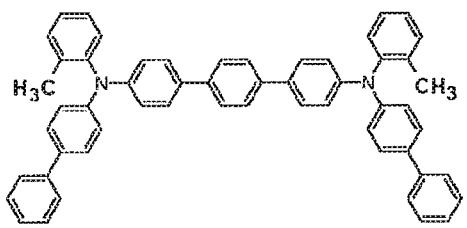
Figure 16:
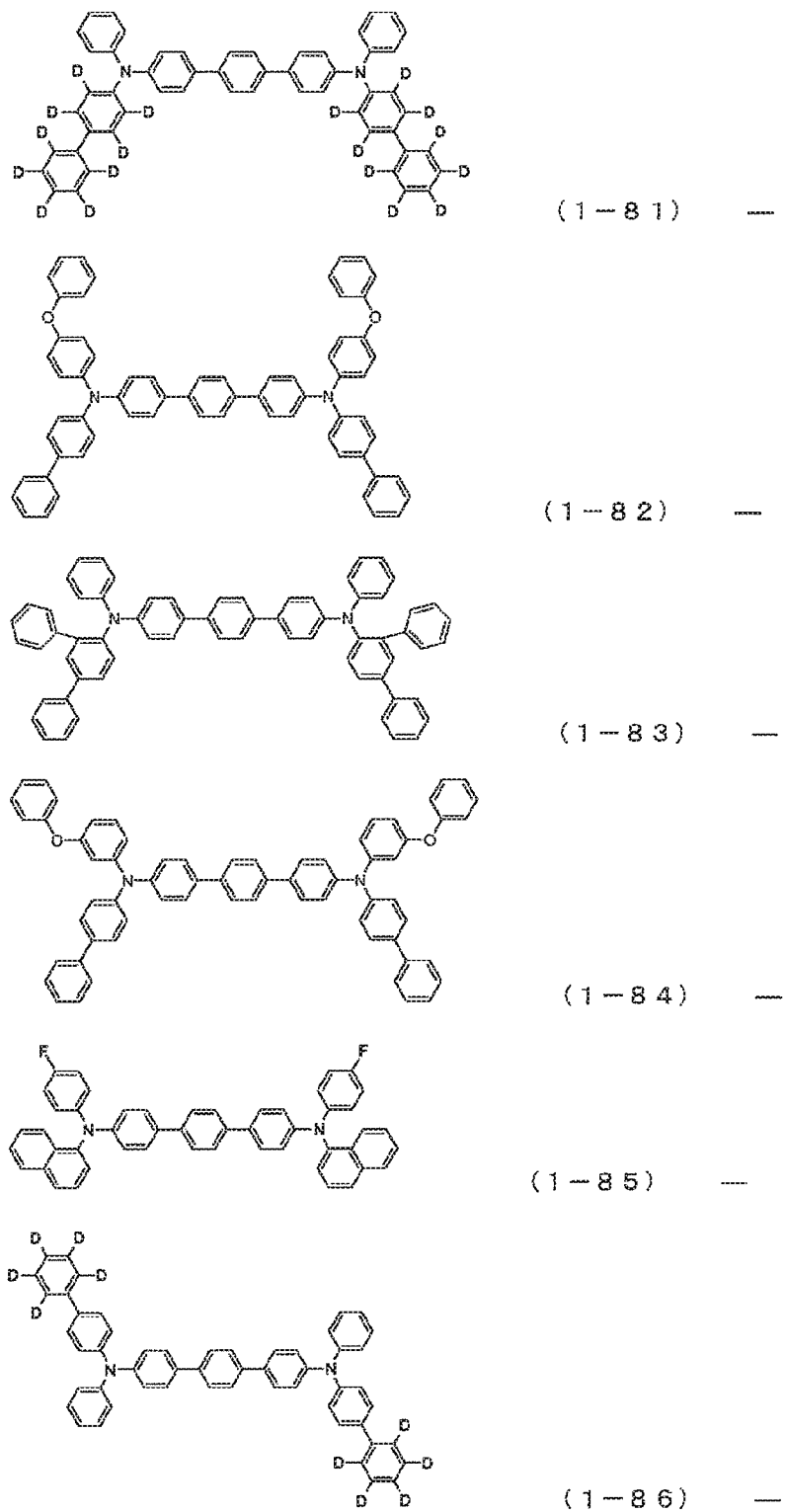
[FIG. 16] is a view showing the structural formulas of Compounds (1-81) to (1-86) in the arylamine compound of the general formula (1).
Figure 17:
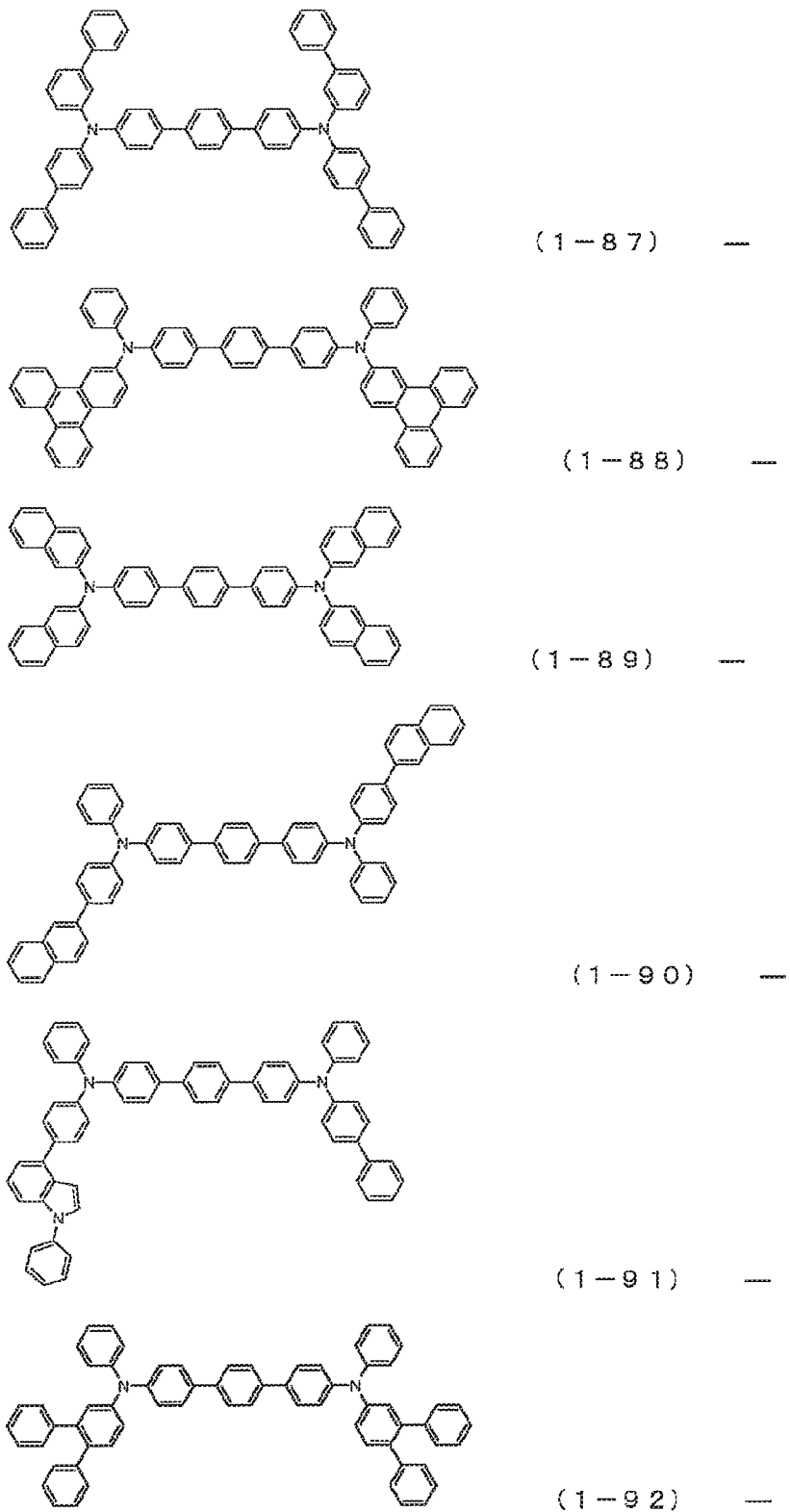
[FIG. 17] is a view showing the structural formulas of Compounds (1-87) to (1-92) in the arylamine compound of the general formula (1).

For example, FIG. 1 illustrates a layered structure used in the below-described Examples. In this example, an anode 2, a hole injection layer 3, a first hole transport layer 5$a$, a second hole transport layer 5$b$, a luminous layer 6, an electron transport layer 7, an electron injection layer 8, and a cathode 9 are formed, in the order of description, on a transparent substrate 1.

Each layer constituting the organic EL device of the present invention will be explained hereinbelow.

<Anode>

The anode 2 is formed on the transparent substrate 1 by vapor deposition of an electrode material with a large work function, such as ITO or gold.

<Hole Transport Layer>

The hole transport layer 5 is provided between the above-mentioned anode 2 and the luminous layer 6. In the present invention, the hole transport layer 5 includes an arylamine compound represented by the following general formula (1) (referred to hereinbelow as "arylamine compound of the general formula (1)").

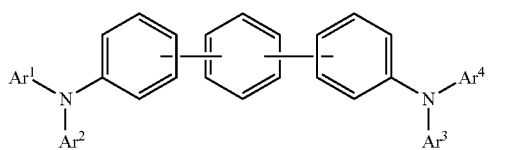

(1)

wherein, $Ar^1$ to $Ar^4$ each represent an aromatic hydrocarbon group or an aromatic heterocyclic group.

The aromatic hydrocarbon groups or aromatic heterocyclic group represented by $Ar^1$ to $Ar^4$ in the general formula (1) can be exemplified by the following groups.

Aromatic Hydrocarbon Groups:

a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, and a triphenylenyl group, etc. Aromatic heterocyclic groups:

a pyridyl group, a pyrimidinyl group, a triazinyl group, a furyl group, a pyrrolyl group, a thienyl group, a quinolyl group, an isoquinolyl group, a quinazolinyl group, a benzofuranyl group, a benzothienyl group, an indolyl group, a carbazolyl group, a benzimidazolyl group, a benzoxazolyl group, a benzothiazolyl group, a pyridopyrimidinyl group, a naphthyridinyl group, a quinoxalinyl group, a benzimidazolyl group, a pyrazolyl group, a naphthopyrimidinyl group, a dibenzofuranyl group, a dibenzothienyl group, a naphthyridinyl group, a phenanthrolinyl group, an acridinyl group, a carbolinyl group, a quinazolinyl group, and a benzoquinazolinyl group, etc.

The aromatic hydrocarbon groups and aromatic heterocyclic group represented by $Ar^1$ to $Ar^4$ may be unsubstituted or may have a substituent. The following groups, in addition to a deuterium atom, a cyano group, and a nitro group, can exemplify the substituents:

a halogen atom, for example, a fluorine atom, a chlorine atom, a bromine atom, and an iodine atom;

an alkyl group having 1 to 6 carbon atoms, for example, a methyl group, an ethyl group, an n-propyl group, an isopropyl group, an n-butyl group, an isobutyl group, a tert-butyl group, an n-pentyl group, an isopentyl group, a neopentyl group, and an n-hexyl group;

an alkyloxy group having 1 to 6 carbon atoms, for example, a methyloxy group, an ethyloxy group, and a propyloxy group;

an alkenyl group, for example, a vinyl group and an allyl group;

an aryloxy group, for example, a phenyloxy group and a tolyloxy group;

an arylalkyloxy group, for example, a benzyloxy group and a phenethyloxy group;

an aromatic hydrocarbon group, for example, a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, and a triphenylenyl group;

an aromatic heterocyclic group, for example, a pyridyl group, a pyrimidinyl group, a triazinyl group, a thienyl group, a furyl group, a pyrrolyl group, a quinolyl group an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, dibenzothienyl group, and a carbolinyl group;

an arylvinyl group, for example, a styryl group and a naphthylvinyl group; and an acyl group, for example, an acetyl group and a benzoyl group.

These substituents may further have the substituents exemplified hereinabove. Further, these substituents may be present individually without forming a ring, or may be bonded to each other via a single bond, a substituted or unsubstituted methylene group, an oxygen atom, or a sulfur atom to form a ring.

Among the abovementioned substituents, alkyl groups having 1 to 6 carbon atoms and alkyloxy groups having 1 to 6 carbon atoms may be straight-chain or branched.

Preferred Embodiment

Among the arylamine compounds of the general formula (1), from the standpoint of stability of a thin film, the arylamine compound represented by the following general formulas (1a-a), (1a-b), (1b-a), (1c-a), or (1c-b) is preferred.

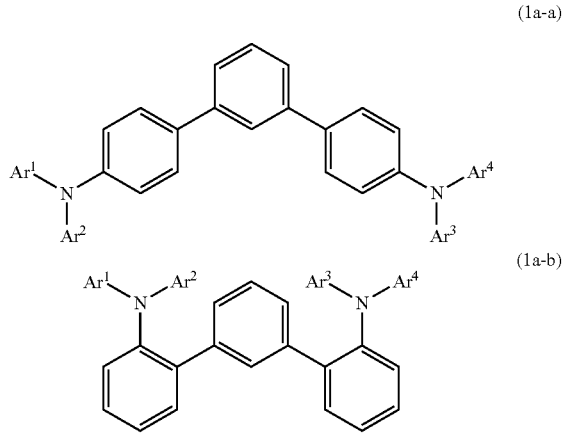

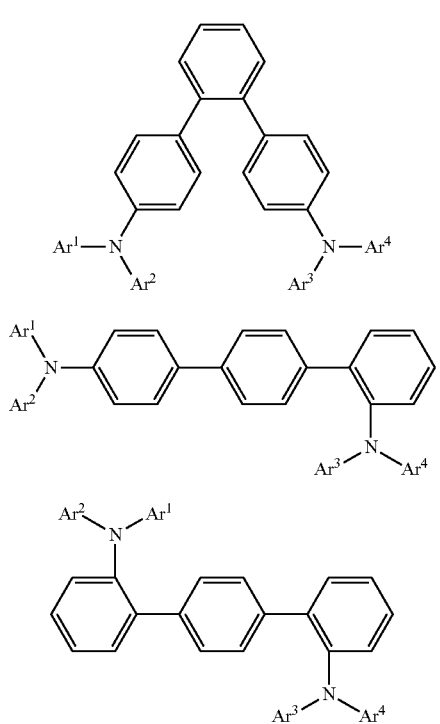

wherein,

Ar$^1$ to Ar$^4$ have the same meaning as that defined in the aforementioned general formula (1).

As the Ar$^1$ to Ar$^4$, aromatic hydrocarbon groups are preferred, and among them, a phenyl group, a biphenyl group, a naphthyl group, and a fluorenyl group are preferred.

When the aromatic hydrocarbon groups or aromatic heterocyclic groups represented by Ar$^1$ to Ar$^4$ have a substituent, a deuterium atom, an alkyl group having 1 to 6 carbon atoms, an alkenyl group having 2 to 6 carbon atoms, or an aromatic hydrocarbon group are preferred as the substituent, and a deuterium atom, a phenyl group, a biphenylyl group, a naphthyl group and a vinyl group are more preferred. An embodiment is also preferred in which these groups are bonded to each other to form a condensed aromatic ring.

The aromatic arylamine compounds of the general formula (1) can be synthesized by a publicly known method such as Suzuki coupling.

The preferred specific examples of the arylamine compound of the general formula (1) can include compounds (1-1) to (1-92) having the structural formulas shown in FIG. 2 to FIG. 17. In the figures, it is also indicated whether each compound corresponds to any of the general formulas (1a-a), (1a-b), (1b-a), (1c-a), and (1c-b). Whether there no correspondence, the compound is marked "-".

The arylamine compound of the general formula (1) can be purified by column chromatography purification, adsorption purification with silica gel, activated carbon, activated clay, and the like, recrystallization or crystallization with a solvent, a sublimation purification method, or the like. In the present invention, the arylamine compound of the general formula (1) is finally purified by the sublimation purification method and supplied for use.

Identification of the compounds can be performed by NMR analysis. The glass transition point (Tg) and work function can be measured as physical property values. The glass transition point (Tg) is an indicator of stability in a thin-film state. The work function is an indicator of hole transport property.

The glass transition point (Tg) can be determined with a high-sensitivity differential scanning calorimeter (DSC3100SA, manufactured by Bruker AXS K. K.) by using a powder.

The work function can be determined with an ionization potential measuring device (PYS-202, manufactured by Sumitomo Heavy Industries, Ltd.) by producing a 100 nm thin film on an ITO substrate.

In the present invention, the above-described arylamine compound of the general formula (1), can be used individually, or two or more such compounds can be used in a mixture. Furthermore, the hole transport layer can be also formed by using this compound together with a publicly known hole transport agent taken within a range in which the excellent properties of the arylamine compound of the general formula (1) are not lost.

Examples of the publicly known hole transport agents are presented below.

Benzidine Derivatives, for Example,
N,N'-diphenyl-N,N'-di(m-tolyl)benzidine (TPD);
N,N'-diphenyl-N,N'-di(α-naphthyl)benzidine (NPD);
N,N,N',N'-tetrabiphenylylbenzidine;
1,1-bis[4-(di-4-tolylamino)phenyl]cyclohexane (TAPC);
arylamine derivatives represented by the below-described general formula (6) or general formula (7); and
various triphenylamine trimers.

Further, in the present invention, the hole transport layer including the above-mentioned arylamine compound preferably has a two-layer structure including the first hole transport layer 5a positioned on the anode side and the second hole transport layer 5b positioned on the luminous layer 6 side, as shown, for example, in FIG. 1. The hole transport layers of such two-layer structure will be described hereinbelow.

In the present invention, a material P-doped with, for instance, trisbromophenylamine hexachloroantimony or a radialene derivative (see WO2014/009310), or, for instance, a polymer compound having the structure of a benzidine derivative such as TPD in a molecule can be used for the hole transport layer.

The above-described hole transport layer is preferably formed by vapor deposition or co-deposition from a gas including the arylamine compound of the general formula (1), but the hole transport layer can be also formed by a publicly known method such as a spin coat method or an ink jet method.

The thickness of the hole transport layer is usually about 25 nm to 60 nm, but since light emission can be performed under a low driving voltage, the increase in the driving voltage can be suppressed even when the thickness is increased, for example, to 100 nm or more. Thus, there is a high degree of freedom in selecting the thickness of the hole transport layer. For example, a practical driving voltage can be maintained at a thickness of 20 nm to 300 nm, in particular 20 nm to 200 nm.

<Luminous Layer>

In the present invention, the luminous layer includes an indenoindole derivative represented by the following general formula (2) (can be referred to hereinbelow as "indenoindole derivative of the general formula (2)") or a carbazole derivative represented by the following general formula (3) (can be referred to hereinbelow as "carbazole derivative of the general formula (3)").

The indenoindole derivative of the general formula (2):

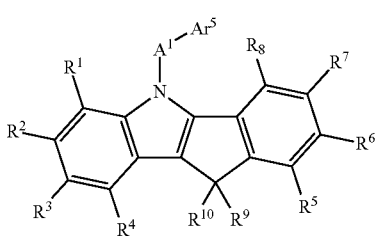

(2)

wherein, $A^1$ represents a divalent group of an aromatic hydrocarbon, a divalent group of an aromatic heteroclic ring, or a single bond;

$Ar^5$ represents an aromatic hydrocarbon group or an aromatic heterocyclic group;

$R^1$ to $R^8$ each represent a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, an aryloxy group, or a disubstituted amino group having an aromatic hydrocarbon group or an aromatic heterocyclic group as a substituent;

respective groups among $R^1$ to $R^4$ may be bonded to each other via a single bond, a substituted or unsubstituted methylene group, an oxygen atom, or a sulfur atom to form a ring;

respective groups among $R^5$ to $R^8$ may be bonded to each other via a single bond, a substituted or unsubstituted methylene group, an oxygen atom, or a sulfur atom to form a ring;

some of $R^1$ to $R^4$ may be detached and the remaining groups of $R^1$ to $R^4$ may be bonded to vacancies generated by the detachment via a substituted or unsubstituted methylene group, an oxygen atom, a sulfur atom, or a monoarylamino group to form a ring;

some of $R^5$ to $R^8$ may be detached and the remaining groups of $R^5$ to $R^8$ may be bonded to vacancies generated by the detachment via a substituted or unsubstituted methylene group, an oxygen atom, a sulfur atom, or a monoarylamino group to form a ring; and $R^9$ and $R^{10}$ are each an alkyl group having 1 to 6 carbon atoms, an aromatic hydrocarbon group, or an aromatic heterocyclic group and may be bonded to each other via a single bond, a substituted or unsubstituted methylene group, an oxygen atom, or a sulfur atom to form a ring.

($A^1$ in the General Formula (2))

Specific examples of the aromatic hydrocarbon or aromatic heterocyclic ring in the divalent group of an aromatic hydrocarbon or the divalent group of an aromatic heteroclic ring represented by $A^1$ in the general formula (2) are presented below.

Aromatic Hydrocarbons:

Benzene, biphenyl, terphenyl, tetrakisphenyl, styrene, naphthalene, anthracene, acenaphthalene, fluorene, phenanthrene, indan, pyrene, triphenylene, fluoranthene, etc.

Aromatic Heteroclic Rings:

Pyridine, pyrimidine, triazine, pyrrole, furan, thiophene, quinoline, isoquinoline, benzofuran, benzothiophene, indoline, carbazole, carboline, benzoxazole, benzothiazole, quinoxaline, benzimidazole, pyrazole, dibenzofuran, dibenzothiophene, naphthyridine, phenanthroline, acridan, quinazoline, benzoquinazoline, etc.

The divalent group of an aromatic hydrocarbon and the divalent group of an aromatic heteroclic ring results from the removal of two hydrogen atoms from the aromatic hydrocarbon and aromatic heteroclic ring.

These divalent groups may be unsubstituted or may have a substituent. The substituents can be exemplified by the same ones as those illustrated as the substituents optionally possessed by the aromatic hydrocarbon group and the aromatic heterocyclic group represented by $Ar^1$ to $Ar^4$ in the general formula (1). Modes which the substituents can adopt are also the same.

($Ar^5$ in the General Formula (2))

The aromatic hydrocarbon group or the aromatic heterocyclic group represented by $Ar^5$ in the general formula (2) can be exemplified by the same ones as those illustrated as the aromatic hydrocarbon group or the aromatic heterocyclic group represented by $Ar^1$ to $Ar^4$ in the general formula (1). These groups may be unsubstituted or may have a substituent. The substituents can be exemplified by the same ones as those illustrated as the substituents optionally possessed by the aromatic hydrocarbon group and the aromatic heterocyclic group represented by $Ar^1$ to $Ar^4$ in the general formula (1). Modes which the substituents can adopt are also the same.

($R^1$ to $R^8$ in the General Formula (2))

The alkyl group having 1 to 6 carbon atoms, the cycloalkyl group having 5 to 10 carbon atoms, or the alkenyl group having 2 to 6 carbon atoms, which is represented by $R^1$ to $R^8$ in the general formula (2), can be specifically exemplified by a methyl group, an ethyl group, an n-propyl group, an isopropyl group, an n-butyl group, an isobutyl group, a tert-butyl group, an n-pentyl group, an isopentyl group, a neopentyl group, an n-hexyl group, a cyclopentyl group, a cyclohexyl group, a 1-adamantyl group, a 2-adamantyl group, a vinyl group, an allyl group, an isopropenyl group, and a 2-butenyl group, etc.

The alkyl groups having 1 to 6 carbon atoms and the alkenyl groups having 2 to 6 carbon atoms may be straight-chain or branched.

The alkyl group having 1 to 6 carbon atoms, the cycloalkyl group having 5 to 10 carbon atoms, and the alkenyl group having 2 to 6 carbon atoms, which are represented by $R^1$ to $R^8$ may be unsubstituted or may have a substituent. The following groups, in addition to a deuterium atom, a cyano group, and a nitro group, can exemplify the substituents:

a halogen atom, for example, a fluorine atom, a chlorine atom, a bromine atom, and an iodine atom;

an alkyloxy group having 1 to 6 carbon atoms, for example, a methyloxy group, an ethyloxy group, and a propyloxy group;

an alkenyl group, for example, a vinyl group and an allyl group;

an aryloxy group, for example, a phenyloxy group and a tolyloxy group;

an arylalkyloxy group, for example, a benzyloxy group and a phenethyloxy group;

an aromatic hydrocarbon group, for example, a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, and a triphenylenyl group;

an aromatic heterocyclic group, for example, a pyridyl group, a pyrimidinyl group, a triazinyl group, a thienyl group, a furyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, and a carbolinyl group;

a disubstituted amino group substituted with an aromatic hydrocarbon group, for example, a diphenylamino group and a dinaphthylamino group;

a disubstituted amino group substituted with an aromatic heterocyclic group, for example, a dipyridylamino group and a ditheinylamino group; and a disubstituted amino group substituted with an aromatic hydrocarbon group and an aromatic heterocyclic group.

These substituents may further have the substituents exemplified hereinabove. Further, these substituents may be present individually without forming a ring, or may be bonded to each other via a single bond, a substituted or unsubstituted methylene group, an oxygen atom, or a sulfur atom to form a ring.

Among the abovementioned substituents, the alkyl group having 1 to 6 carbon atoms may be straight-chain or branched.

The alkyloxy group having 1 to 6 carbon atoms or the cycloalkyloxy group having 5 to 10 carbon atoms, which is represented by $R^1$ to $R^8$ in the general formula (2), can be specifically exemplified by a methyloxy group, an ethyloxy group, an n-propyloxy group, an isopropyloxy group, an n-butyloxy group, a tert-butyloxy group, an n-pentyloxy group, an n-hexyloxy group, a cyclopentyloxy group, a cyclohexyloxy group, a cycloheptyloxy group, a cyclooctyloxy group, a 1-adamantyloxy group, and a 2-adamantyloxy group, etc. The alkyloxy group having 1 to 6 carbon atoms may be straight-chain or branched. These groups may be unsubstituted or may have a substituent. The substituents can be exemplified by the same ones as those illustrated as the substituents optionally possessed by the alkyl group having 1 to 6 carbon atoms, the cycloalkyl group having 5 to 10 carbon atoms, and the alkenyl group having 2 to 6 carbon atoms which are represented by $R^1$ to $R^8$ in the general formula (2). Modes which the substituents can adopt are also the same.

The aromatic hydrocarbon group or the aromatic heterocyclic group represented by $R^1$ to $R^8$ in the general formula (2) can be exemplified by the same ones as those illustrated as the aromatic hydrocarbon group or the aromatic heterocyclic group represented by $Ar^1$ to $Ar^4$ in the general formula (1). These groups may be unsubstituted or may have a substituent. The substituents can be exemplified by the same ones as those illustrated as the substituents optionally possessed by the aromatic hydrocarbon group and the aromatic heterocyclic group represented by $Ar^1$ to $Ar^4$ in the general formula (1). Modes which the substituents can adopt are also the same.

The aryloxy group represented by $R^1$ to $R^8$ in the general formula (2) can be specifically exemplified by a phenyloxy group, a biphenylyloxy group, a terphenylyloxy group, a naphthyloxy group, an anthracenyloxy group, a phenanthrenyloxy group, a fluorenyloxy group, an indenyloxy group, a pyrenyloxy group, and a perylenyloxy group. These aryloxy groups may be unsubstituted or may have a substituent. The substituents can be exemplified by the same ones as those illustrated as the substituents optionally possessed by the aromatic hydrocarbon group and the aromatic heterocyclic group represented by $Ar^1$ to $Ar^4$ in the general formula (1). Modes which the substituents can adopt are also the same.

The aromatic hydrocarbon group or the aromatic heterocyclic group in the "disubstituted amino group having an aromatic hydrocarbon group or an aromatic heterocyclic group as a substituent", which is represented by $R^1$ to $R^3$ in the general formula (2), can be exemplified by the same ones as those illustrated as the aromatic hydrocarbon group or the aromatic heterocyclic group represented by $Ar^1$ to $Ar^4$ in the general formula (1). The disubstituted amino group may be unsubstituted or may have a substituent. The substituents can be exemplified by the same ones as those illustrated as the substituents optionally possessed by the aromatic hydrocarbon group and the aromatic heterocyclic group represented by $Ar^1$ to $Ar^4$ in the general formula (1). Modes which the substituents can adopt are also the same.

$R^1$ to $R^4$ may be present individually without forming a ring, or may be bonded to each other via a single bond, a substituted or unsubstituted methylene group, an oxygen atom, or a sulfur atom to form a ring. Likewise, $R^5$ to $R^8$ may be present individually without forming a ring, or may be bonded to each other via a single bond, a substituted or unsubstituted methylene group, an oxygen atom, or a sulfur atom to form a ring.

Figure 18:
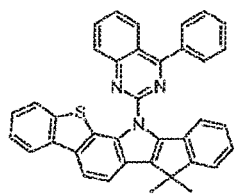
[FIG. 18] is a view showing the structural formulas of Compounds (2-1) to (2-6) in the indenoindole derivative of the general formula (2).
Figure 18:
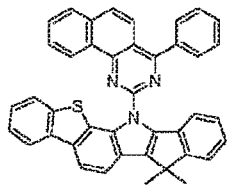
Figure 18:
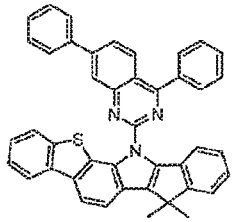
Figure 18:
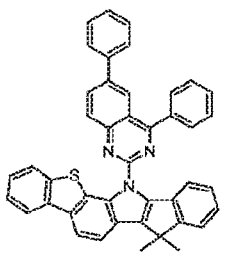
Figure 18:
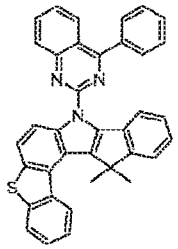
Figure 18:
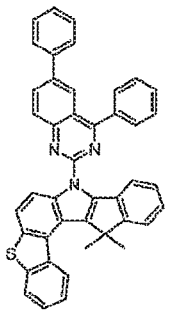

Further, some of $R^1$ to $R^4$ may be detached and the remaining groups of $R^1$ to $R^4$ may be bonded to vacancies generated by the detachment via a substituted or unsubstituted methylene group, an oxygen atom, a sulfur atom, or a monoarylamino group to form a ring, as in the compounds (2-1) to (2-6) in FIG. 18. Likewise, some of $R^5$ to $R^8$ may be detached and the remaining groups of $R^5$ to $R^8$ may be bonded to vacancies generated by the detachment via a substituted or unsubstituted methylene group, an oxygen atom, a sulfur atom, or a monoarylamino group to form a ring.

The aryl group in the monoarylamino group in this case can be exemplified by the same ones as those illustrated as the aromatic hydrocarbon group and the aromatic heterocyclic group represented by $Ar^1$ to $Ar^4$ in the general formula (1). The aryl group may be unsubstituted or substituted. Examples of the substituents can be exemplified by the same ones as those illustrated as the substituents optionally possessed by the aromatic hydrocarbon group and the aromatic heterocyclic group represented by $Ar^1$ to $Ar^4$ in the general formula (1). Modes which the substituents can adopt are also the same.

($R^9$ and $R^{10}$ in the General Formula (2))

The alkyl group having 1 to 6 carbon atoms, which is represented by $R^9$ and $R^{10}$ in the general formula (2), can be exemplified by the same ones as those illustrated as the alkyl group having 1 to 6 carbon atoms which is represented by $R^1$ to $R^8$ in the general formula (2).

This alkyl group may be unsubstituted or substituted. Examples of the substituents can be exemplified by the same ones as those illustrated as the substituents optionally possessed by the alkyl group having 1 to 6 carbon atoms, the cycloalkyl group having 5 to 10 carbon atoms, and the alkenyl group having 2 to 6 carbon atoms, which are represented by $R^1$ to $R^8$ in the general formula (2). Modes which the substituents can adopt are also the same.

The aromatic hydrocarbon group or the aromatic heterocyclic group represented by $R^9$ and $R^{10}$ can be exemplified by the same ones as those illustrated as the aromatic hydrocarbon group or the aromatic heterocyclic group represented by $Ar^1$ to $Ar^4$ in the general formula (1).

This group may be unsubstituted or substituted. Examples of the substituents can be exemplified by the same ones as those illustrated as the substituents optionally possessed by the aromatic hydrocarbon group and the aromatic heterocyclic group represented by $Ar^1$ to $Ar^4$ in the general formula (1). Modes which the substituents can adopt are also the same.

$R^9$ and $R^{10}$ may be present individually without forming a ring, or may be bonded to each other via a single bond, a substituted or unsubstituted methylene group, an oxygen atom, or a sulfur atom to form a ring.

Preferred Embodiment of the General Formula (2)

As $A^1$, a divalent group of an aromatic hydrocarbon or a single bond is preferred, a divalent group resulting from the removal of two hydrogen atoms from benzene, biphenyl, or naphthalene or a single bond is more preferred, and a divalent group resulting from the removal of two hydrogen atoms from benzene or a single bond is particularly preferred.

As $Ar^5$, a phenyl group, a biphenylyl group, a naphthyl group, or an aromatic heterocyclic group is preferred, and an aromatic heterocyclic group is more preferred. The preferred examples of the aromatic heterocyclic group include a triazinyl group, a quinazolinyl group, a naphthopyrimidinyl group, a benzimidazolyl group, a pyridopyrimidinyl group, a naphthyridinyl group, a pyridyl group, a quinolyl group, an isoquinolyl group, a quinazolinyl group, or a benzoquinazolinyl group.

Concerning the preferred $R^1$ to $R^4$, an embodiment is preferred in which, for example, as indicated by the below-described general formulas (2a) to (2c), any one of $R^1$ to $R^4$ is an aromatic hydrocarbon group or an aromatic heterocyclic group, another one of $R^1$ to $R^4$ is detached, thereby forming a vacancy, and the aromatic hydrocarbon group or the aromatic heterocyclic group is bonded to the vacancy via a substituted or unsubstituted methylene group, an oxygen atom, a sulfur atom, or a monoarylamino group to form a ring. The preferred examples of the aromatic hydrocarbon group and aromatic heterocyclic group in this case include a phenyl group, an indenyl group, an indolyl group, a benzofuranyl group, and a benzothienyl group. The preferred examples of the ring formed by the aromatic hydrocarbon group or the aromatic heterocyclic group and the benzene ring to which $R^1$ to $R^4$ are bonded include a fluorene ring, a carbazole ring, a dibenzofuran ring, a dibenzothiophene ring, an indenoindole ring, an indenobenzofuran ring, an indenobenzothiophene ring, a benzofuroindole ring, a benzothienoindole ring, and an indoloindole ring.

Further, concerning the preferred $R^1$ to $R^4$, an embodiment is preferred in which, for example, as indicated by the below-described general formulas (2d) to (2e), two adjacent groups, among $R^1$ to $R^4$, are an alkenyl group having 2 to 6 carbon atoms, an aromatic hydrocarbon group, or an aromatic heterocyclic group, the two adjacent groups ($R^1$ to $R^4$) are bonded to each other via a single bond, to form a heterocyclic ring that has a condensed ring or a condensed structure with a benzene ring to which $R^1$ to $R^4$ are bonded. In this case, a vinyl group or a phenyl group is preferred as the alkenyl group having 2 to 6 carbon atoms or the aromatic hydrocarbon group. The preferred examples of the condensed ring which is formed include a naphthalene ring, a phenanthrene ring, and a triphenylene ring.

The compounds of the general formulas (2a) to (2e) are all novel compound, and by using these compounds as materials for a luminous layer, it is possible to realize a high luminous efficiency.

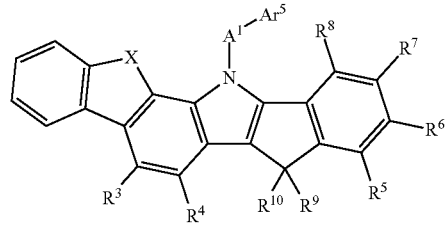

(2a)

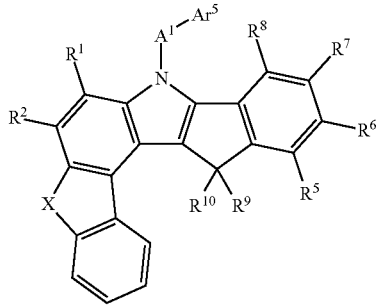

(2b)

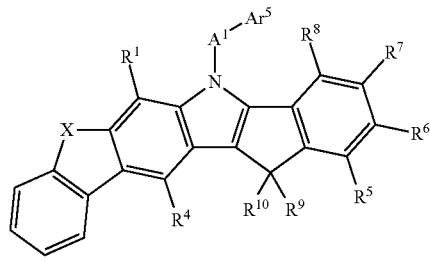

(2c)

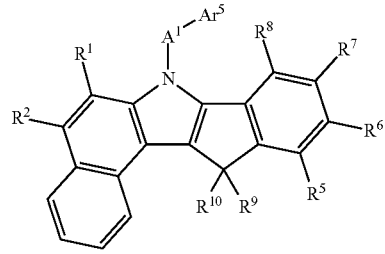

(2d)

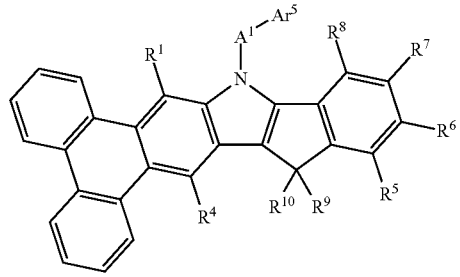

(2e)

wherein,

X represents a substituted or unsubstituted methylene group, an oxygen atom, a sulfur atom, or a monoarylamino group;

$A^1$, $Ar^5$, and $R^1$ to $R^{10}$ have the same meaning as that defined in the aforementioned general formula (2).

Concerning the preferred $R^5$ to $R^8$, an embodiment is preferred in which two adjacent groups or all groups, from among $R^5$ to $R^8$, are vinyl groups, and the two adjacent vinyl groups are bonded to each other via a single bond to form a condensed ring, that is, an embodiment in which $R^5$ to $R^8$ form a naphthalene ring or a phenanthrene ring together with the benzene ring to which $R^5$ to $R^8$ are bonded.

$R^9$ and $R^{10}$ are preferably alkyl groups having 1 to 6 carbon atoms, and a methyl group is particularly preferred.

Figure 19:
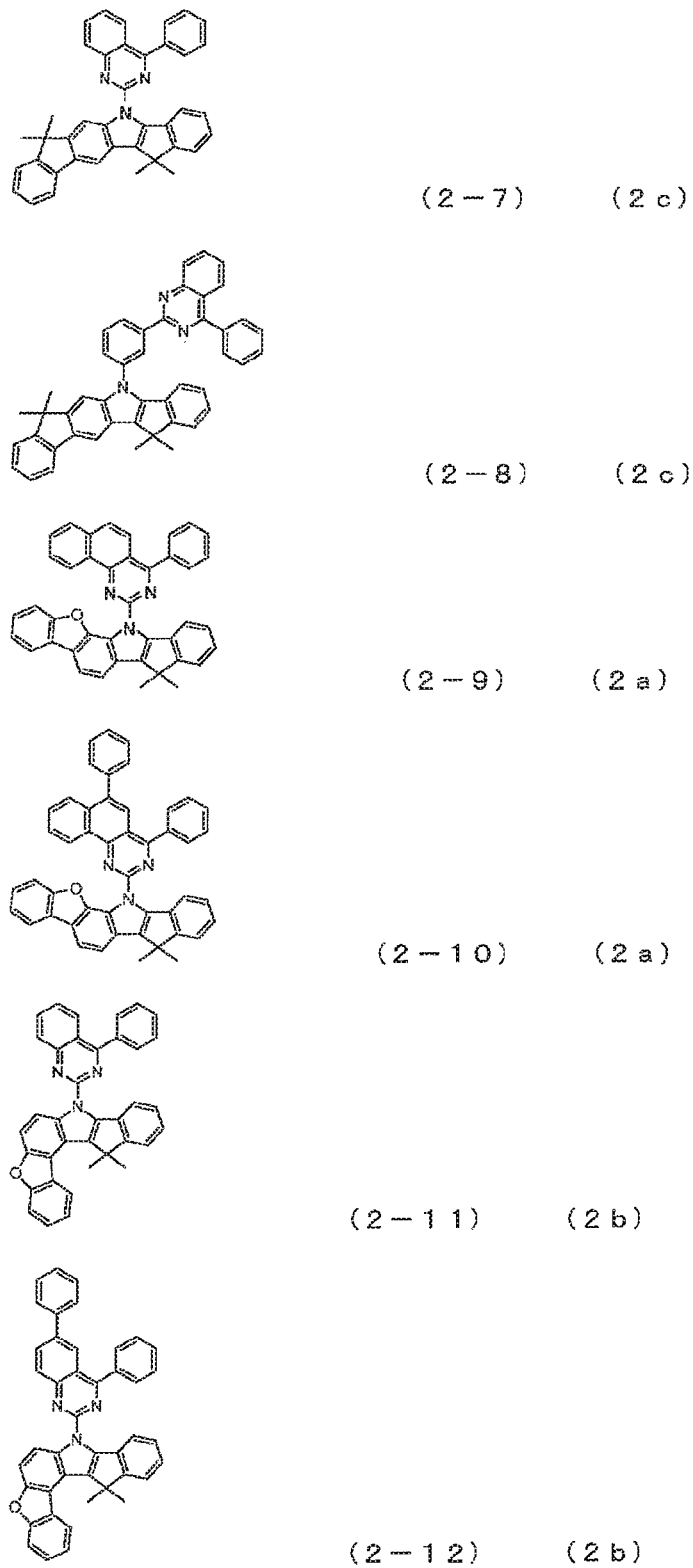
[FIG. 19] is a view showing the structural formulas of Compounds (2-7) to (2-12) in the indenoindole derivative of the general formula (2).
Figure 20:
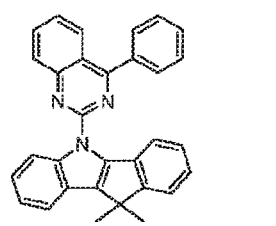
[FIG. 20] is a view showing the structural formulas of Compounds (2-13) to (2-15) in the indenoindole derivative of the general formula (2).
Figure 20:
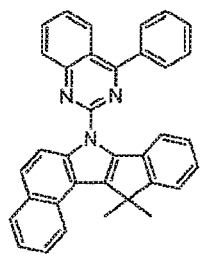
Figure 20:
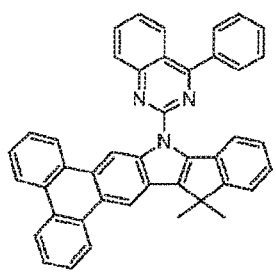

The preferred specific examples of the indenoindole derivative of the general formula (2) can include compounds (2-1) to (2-15) having the structural formulas shown in FIG. 18 to FIG. 20, but the compound of the general formula (2) is not limited thereto. In the figures, it is also indicated whether each compound corresponds to any of the general formulas (2a) to (2e). Whether there is no correspondence, the compound is marked "-".

The abovementioned indenoindole derivatives can be synthesized by a publicly known method or according thereto (see Patent Document 6). For example, as indicated in the below-described example, the synthesis can be performed by Suzuki coupling by using a compound having a structure corresponding to -$A^1$-$Ar^5$ and a halogen atom, and an indenoindole derivative having a hydrogen atom in a portion corresponding to -$A^1$-$Ar^5$ in the presence of a boron reagent such as tri-tert-butylphosphonium tetrafluoroborate, and a catalyst such as tris(dibenzylideneacetone)dipalladium.

The synthesized compound can be purified by column chromatography purification, adsorption purification with silica gel, activated carbon, activated clay, and the like, recrystallization or crystallization with a solvent, a sublimation purification method, or the like. The compound to be used in the organic EL device of the present invention is finally purified by the sublimation purification method and supplied for use.

Carbazole Derivative Represented by the General Formula (3):

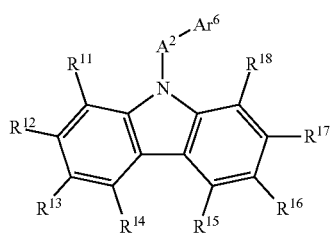

wherein, $A^2$ represents a divalent group of an aromatic hydrocarbon, a divalent group of an aromatic heteroclic ring, or a single bond;

$Ar^6$ represents an aromatic hydrocarbon group or an aromatic heterocyclic group;

$R^{11}$ to $R^{18}$ each represent a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, an aryloxy group, or a disubstituted amino group having an aromatic hydrocarbon group or an aromatic heterocyclic group as a substituent;

respective groups among $R^{11}$ to $R^{14}$ may be bonded to each other via a single bond, a substituted or unsubstituted methylene group, an oxygen atom, or a sulfur atom to form a ring;

respective groups among $R^{15}$ to $R^{18}$ may be bonded to each other via a single bond, a substituted or unsubstituted methylene group, an oxygen atom, or a sulfur atom to form a ring;

some of $R^{11}$ to $R^{14}$ may be detached and the remaining groups of $R^{11}$ to $R^{14}$ may be bonded to vacancies generated by the detachment via a substituted or unsubstituted methylene group, an oxygen atom, a sulfur atom, or a monoarylamino group to form a ring; and some of $R^{15}$ to $R^{18}$ may be detached and the remaining groups of $R^{15}$ to $R^{18}$ may be bonded to vacancies generated by the detachment via a substituted or unsubstituted methylene group, an oxygen atom, a sulfur atom, or a monoarylamino group to form a ring.

($A^2$ in the General Formula (3))

The divalent group of an aromatic hydrocarbon or the divalent group of an aromatic heteroclic ring represented by $A^2$ in the general formula (3) can be exemplified by the same ones as those illustrated as the divalent group of an aromatic hydrocarbon or the divalent group of an aromatic heteroclic ring represented by $A^1$ in the general formula (2). These groups may be unsubstituted or may have a substituent. The substituents can be exemplified by the same ones as those illustrated as the substituents optionally possessed by the divalent group of an aromatic hydrocarbon and the divalent group of an aromatic heteroclic ring represented by $A^1$ in the general formula (2). Modes which the substituents cart adopt are also the same.

($Ar^6$ in the General Formula (3))

The aromatic hydrocarbon group or the aromatic heterocyclic group represented by $Ar^6$ in the general formula (3) can be exemplified by the same ones as those illustrated in relation to the aromatic hydrocarbon group or the aromatic heterocyclic group represented by $Ar^1$ to $Ar^4$ in the general formula (1). These groups may be unsubstituted or may have a substituent. The substituents can be exemplified by the same ones as those illustrated in relation to the substituents optionally possessed by the aromatic hydrocarbon group and the aromatic heterocyclic group represented by $Ar^1$ to $Ar^4$ in the general formula (1). Modes which the substituents can adopt are also the same.

($R^{11}$ to $R^{18}$ in the General Formula (3))

The alkyl group having 1 to 6 carbon atoms, the cycloalkyl group having 5 to 10 carbon atoms, or the alkenyl group having 2 to 6 carbon atoms, which is represented by $R^{11}$ to $R^{18}$ in the general formula (3), can be exemplified by the same ones as those illustrated as the alkyl group having 1 to 6 carbon atoms, the cycloalkyl group having 5 to 10 carbon atoms, or the alkenyl group having 2 to 6 carbon atoms which are represented by $R^1$ to $R^8$ in the general formula (2). These groups may be unsubstituted or may have a substituent. The substituents can be exemplified by the same ones as those illustrated as the substituents optionally possessed by the alkyl group having 1 to 6 carbon atoms, the cycloalkyl group having 5 to 10 carbon atoms, and the alkenyl group having 2 to 6 carbon atoms which are represented by $R^1$ to $R^8$ in the general formula (2). Modes which the substituents can adopt are also the same.

The alkyloxy group having 1 to 6 carbon atoms or the cycloalkyloxy group having 5 to 10 carbon atoms, which is represented by $R^{11}$ to $R^{18}$ in the general formula (3), can be exemplified by the same ones as those illustrated as the alkyloxy group having 1 to 6 carbon atoms or the cycloalkyloxy group having 5 to 10 carbon atoms, which is represented by $R^1$ to $R^8$ in the general formula (2). These groups may be unsubstituted or may have a substituent. The substituents can be exemplified by the same ones as those illustrated as the substituents optionally possessed by the alkyl group having 1 to 6 carbon atoms, the cycloalkyl group having 5 to 10 carbon atoms, and the alkenyl group having 2 to 6 carbon atoms which are represented by $R^1$ to $R^8$ in the general formula (2). Modes which the substituents can adopt are also the same.

The aromatic hydrocarbon group or the aromatic heterocyclic group, which is represented by $R^{11}$ to $R^{18}$ in the general formula (3), can be exemplified by the same ones as those illustrated in relation to the aromatic hydrocarbon group or the aromatic heterocyclic group, which are represented by $R^1$ to $R^8$ in the general formula (2). These groups may be unsubstituted or may have a substituent. The substituents can be exemplified by the same ones as those illustrated as the substituents optionally possessed by the aromatic hydrocarbon group and the aromatic heterocyclic group, which are represented by $R^1$ to $R^8$ in the general formula (2). Modes which the substituents can adopt are also the same.

The aryloxy group, which is represented by $R^{11}$ to $R^{18}$ in the general formula (3), can be exemplified by the same ones as those illustrated as in relation to the aryloxy group which is represented by $R^1$ to $R^8$ in the general formula (2). The aryloxy group may be unsubstituted or may have a substituent. The substituents can be exemplified by the same ones as those illustrated as the substituents optionally possessed by the aryloxy group which is represented by $R^1$ to $R^8$ in the general formula (2). Modes which the substituents can adopt are also the same.

The "disubstituted amino group having an aromatic hydrocarbon group or an aromatic heterocyclic group as a substituent", which is represented by $R^{11}$ to $R^{18}$ in the general formula (3), can be exemplified by the same ones as those illustrated in relation to the "disubstituted amino group having an aromatic hydrocarbon group or an aromatic heterocyclic group as a substituent" which is represented by $R^1$ to $R^8$ in the general formula (2). The disubstituted amino group may be unsubstituted or may have a substituent. The substituents can be exemplified by the same ones as those illustrated as the substituents optionally possessed by the "disubstituted amino group having an aromatic hydrocarbon group or an aromatic heterocyclic group as a substituent" represented by $R^1$ to $R^8$ in the general formula (2). Modes which the substituents can adopt are also the same.

$R^{11}$ to $R^{14}$ may be present individually without forming a ring, or may be bonded to each other via a single bond, a substituted or unsubstituted methylene group, an oxygen atom, or a sulfur atom to form a ring. Likewise, $R^{15}$ to $R^{18}$ may be present individually without forming a ring, or may be bonded to each other via a single bond, a substituted or unsubstituted methylene group, an oxygen atom, or a sulfur atom to form a ring.

Figure 21:
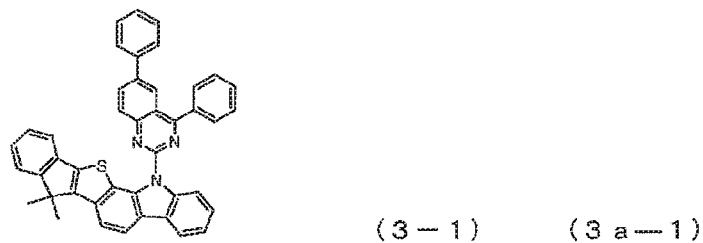
[FIG. 21] is a view showing the structural formulas of Compounds (3-1) to (3-6) in the carbazole derivative of the general formula (3).
Figure 21:
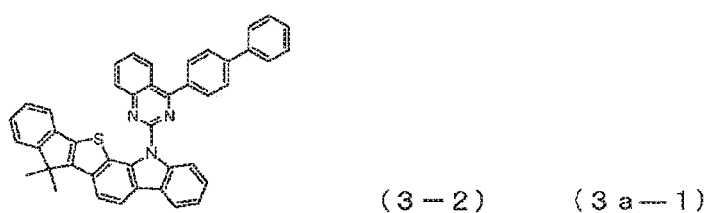
Figure 21:
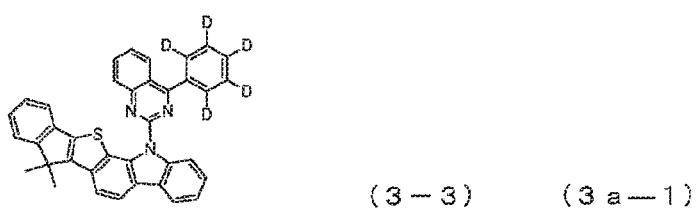
Figure 21:
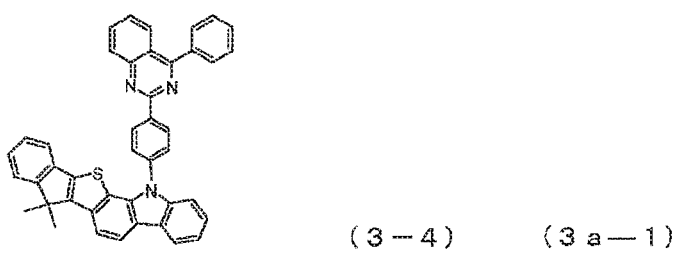
Figure 21:
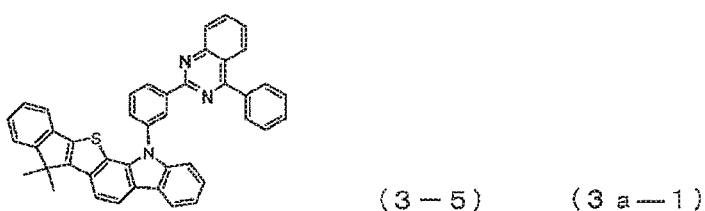
Figure 21:
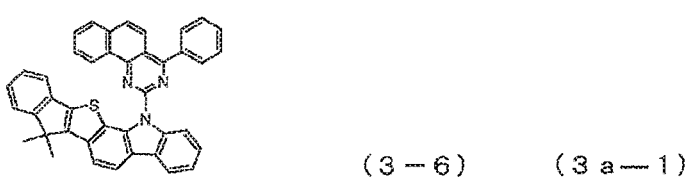
Figure 22:
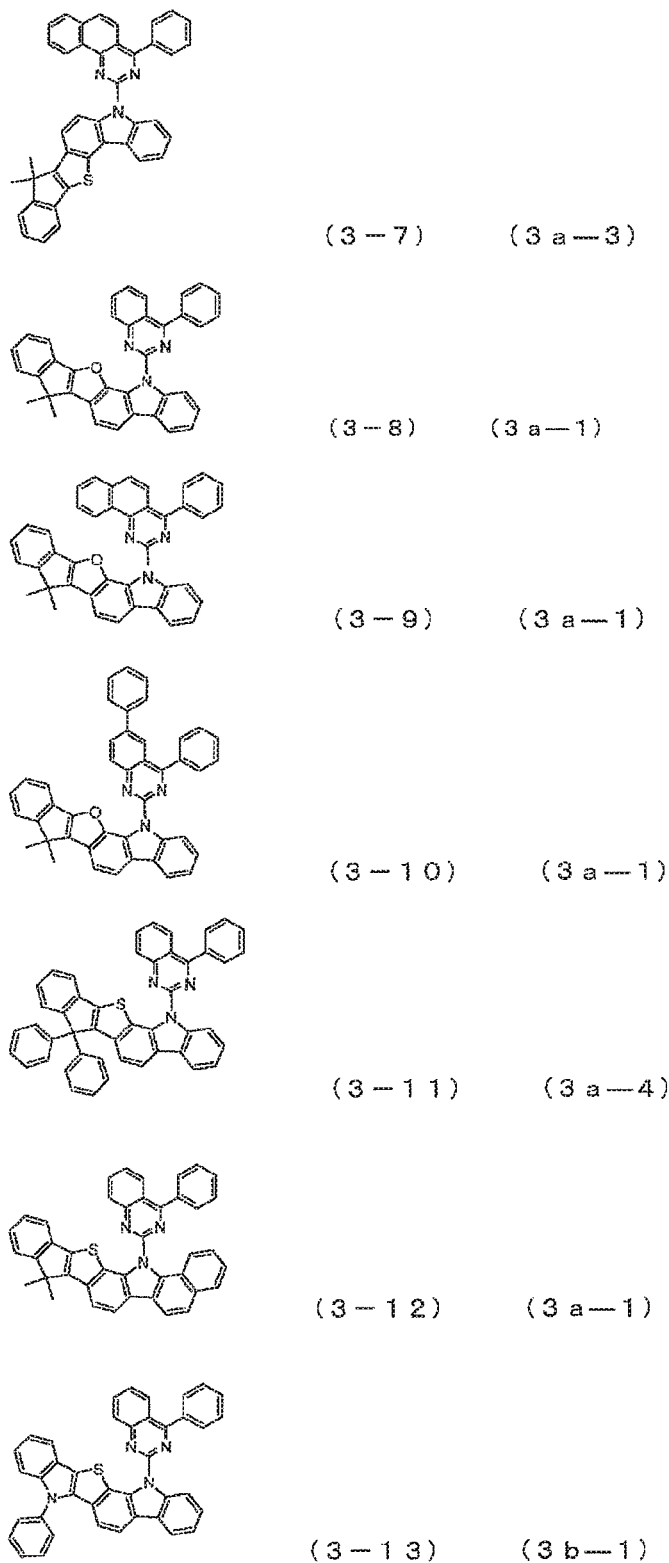
[FIG. 22] is a view showing the structural formulas of Compounds (3-7) to (3-13) in the carbazole derivative of the general formula (3).
Figure 23:
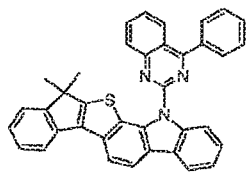
[FIG. 23] is a view showing the structural formulas of Compounds (3-14) to (3-19) in the carbazole derivative of the general formula (3).
Figure 23:
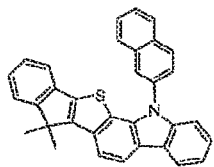
Figure 23:
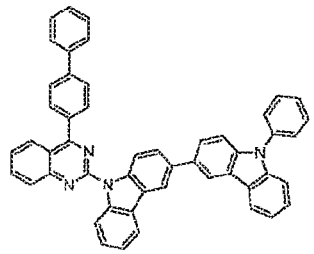
Figure 23:
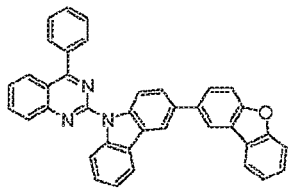
Figure 23:
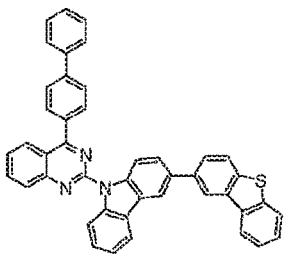
Figure 23:
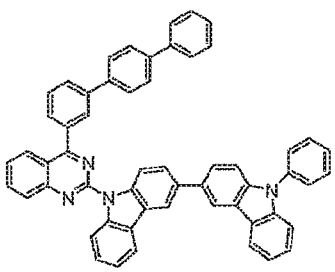
Figure 24:
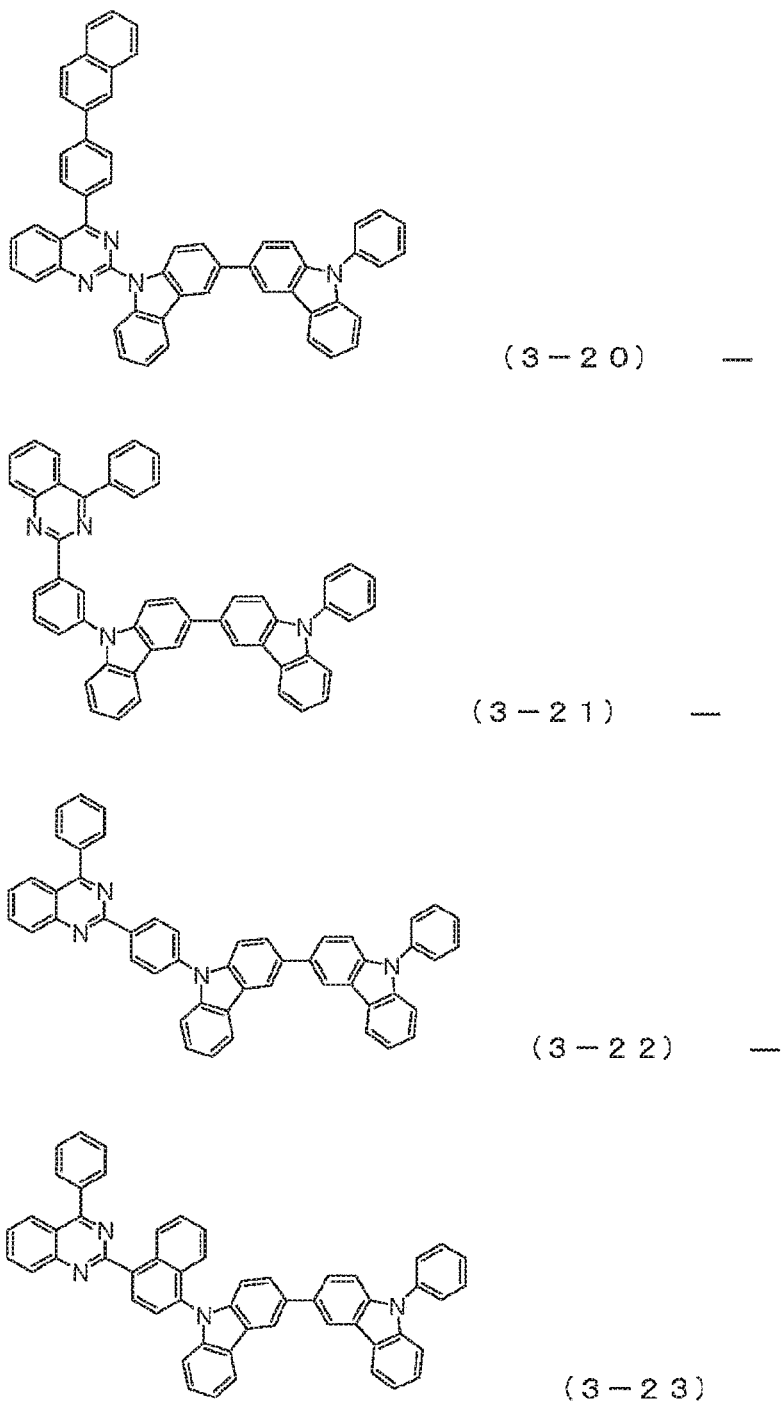
[FIG. 24] is a view showing the structural formulas of Compounds (3-20) to (3-23) in the carbazole derivative of the general formula (3).
Figure 25:
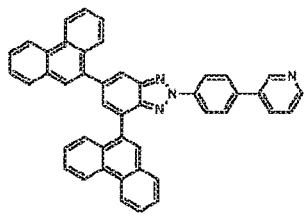
[FIG. 25] is a view showing the structural formulas of Compounds (4-1) to (4-7) in the benzotriazole derivative of the general formula (4).
Figure 25:
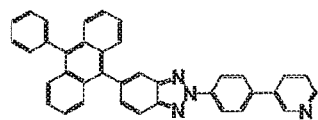
Figure 25:
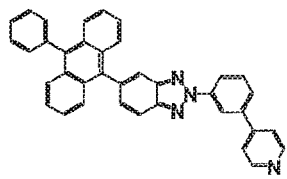
Figure 25:
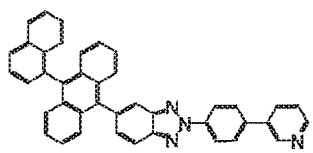
Figure 25:
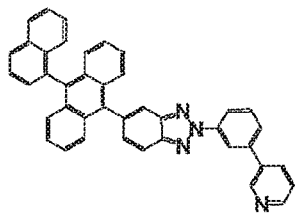
Figure 25:
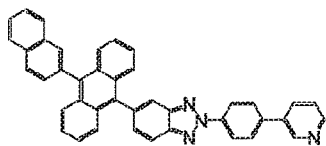
Figure 25:
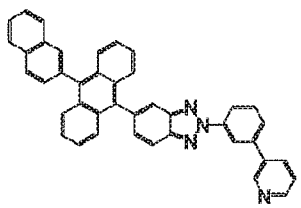
Figure 26:
[FIG. 26] is a view showing the structural formulas of Compounds (4-8) to (4-12) in the benzotriazole derivative of the general formula (4).
Figure 26:
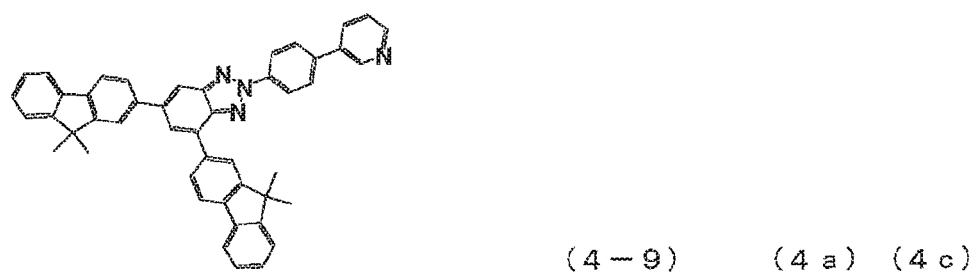
Figure 26:
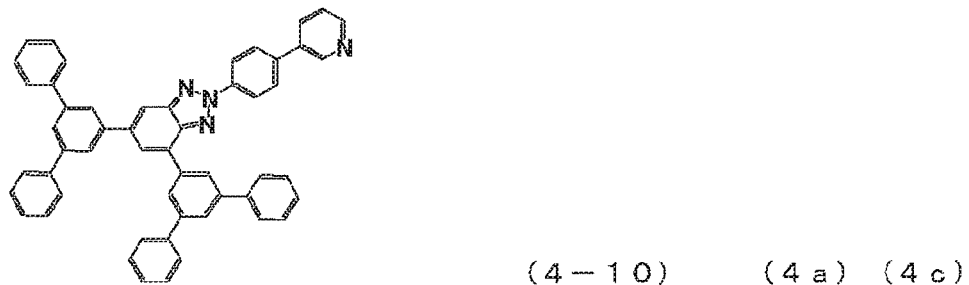
Figure 26:
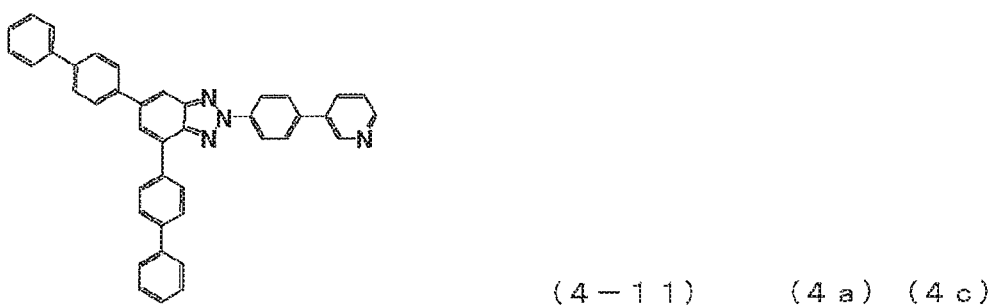
Figure 26:
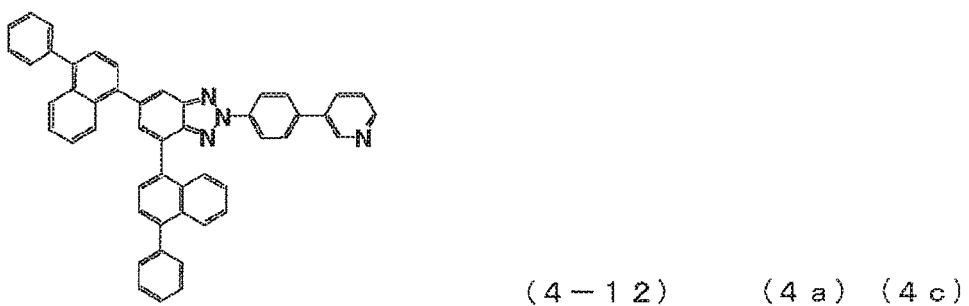
Figure 27:
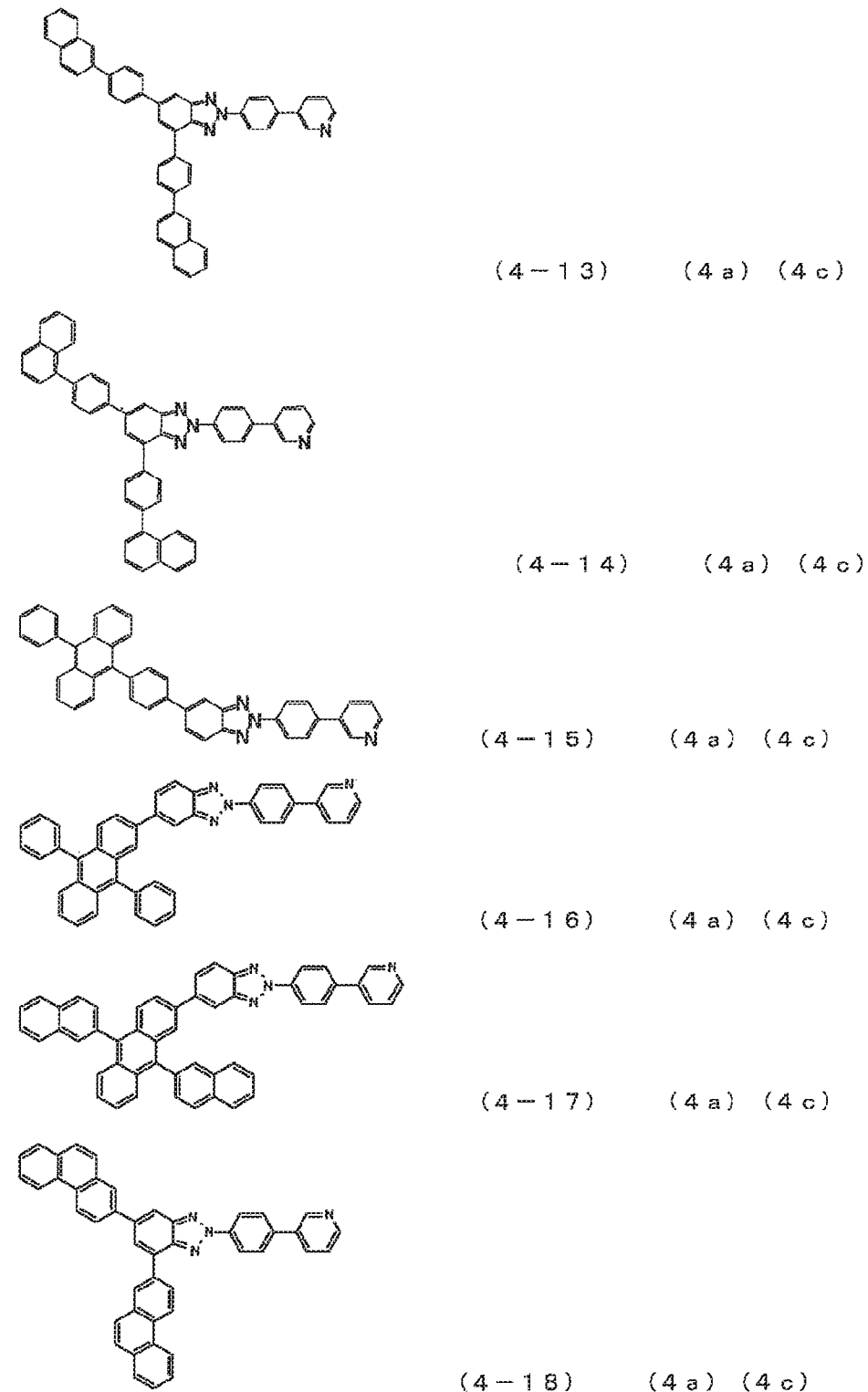
[FIG. 27] is a view showing the structural formulas of Compounds (4-13) to (4-18) in the benzotriazole derivative of the general formula (4).
Figure 28:
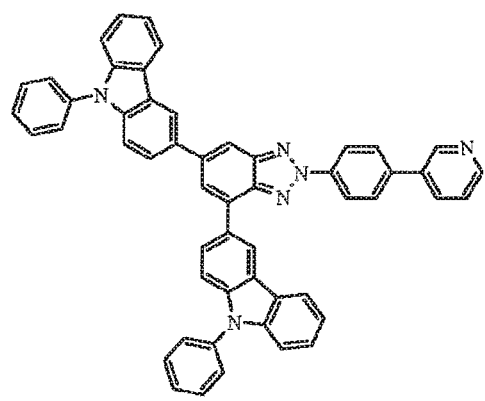
[FIG. 28] is a view showing the structural formulas of Compounds (4-19) to (4-20) in the benzotriazole derivative of the general formula (4).
Figure 28:
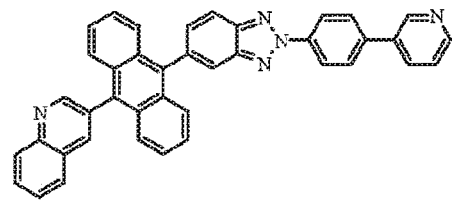
Figure 29:
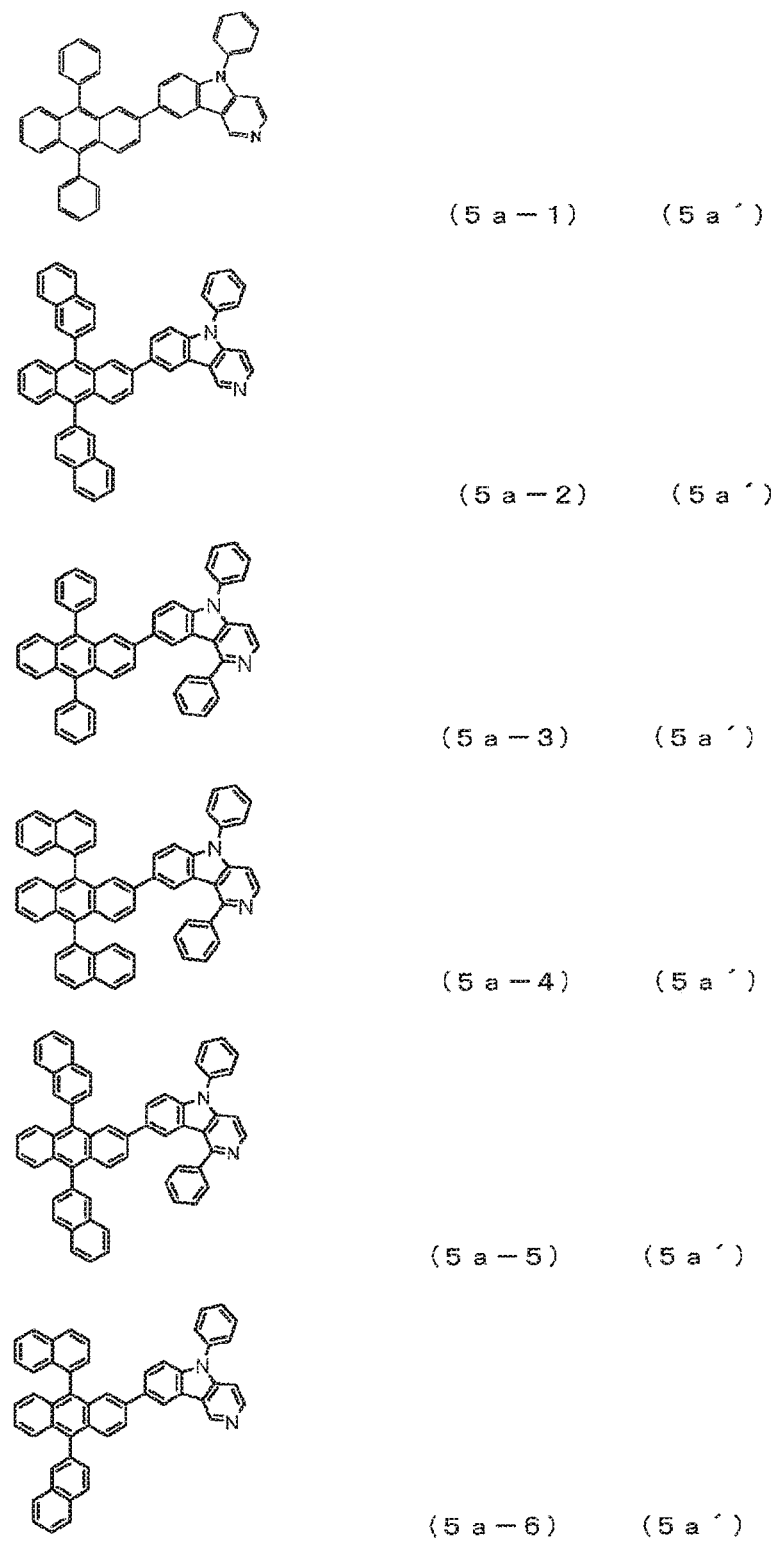
[FIG. 29] is a view showing the structural formulas of Compounds (5a-1) to (5a-6) in the anthracene derivative of the general formula (5a).
Figure 30:
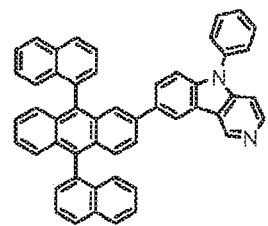
[FIG. 30] is a view showing the structural formulas of Compounds (5a-7) to (5a-11) in the anthracene derivative of the general formula (5a).
Figure 30:
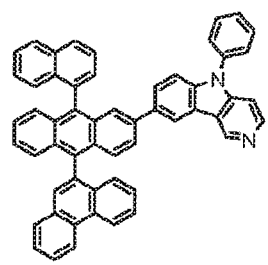
Figure 30:
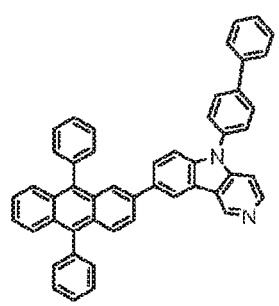
Figure 30:
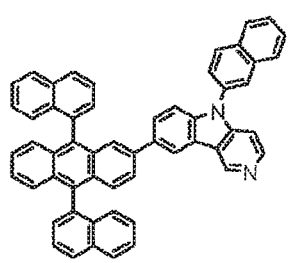
Figure 30:
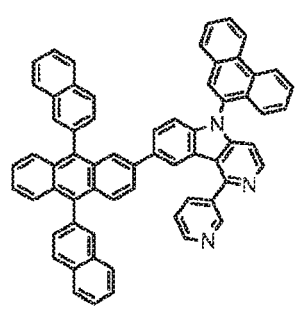
Figure 31:
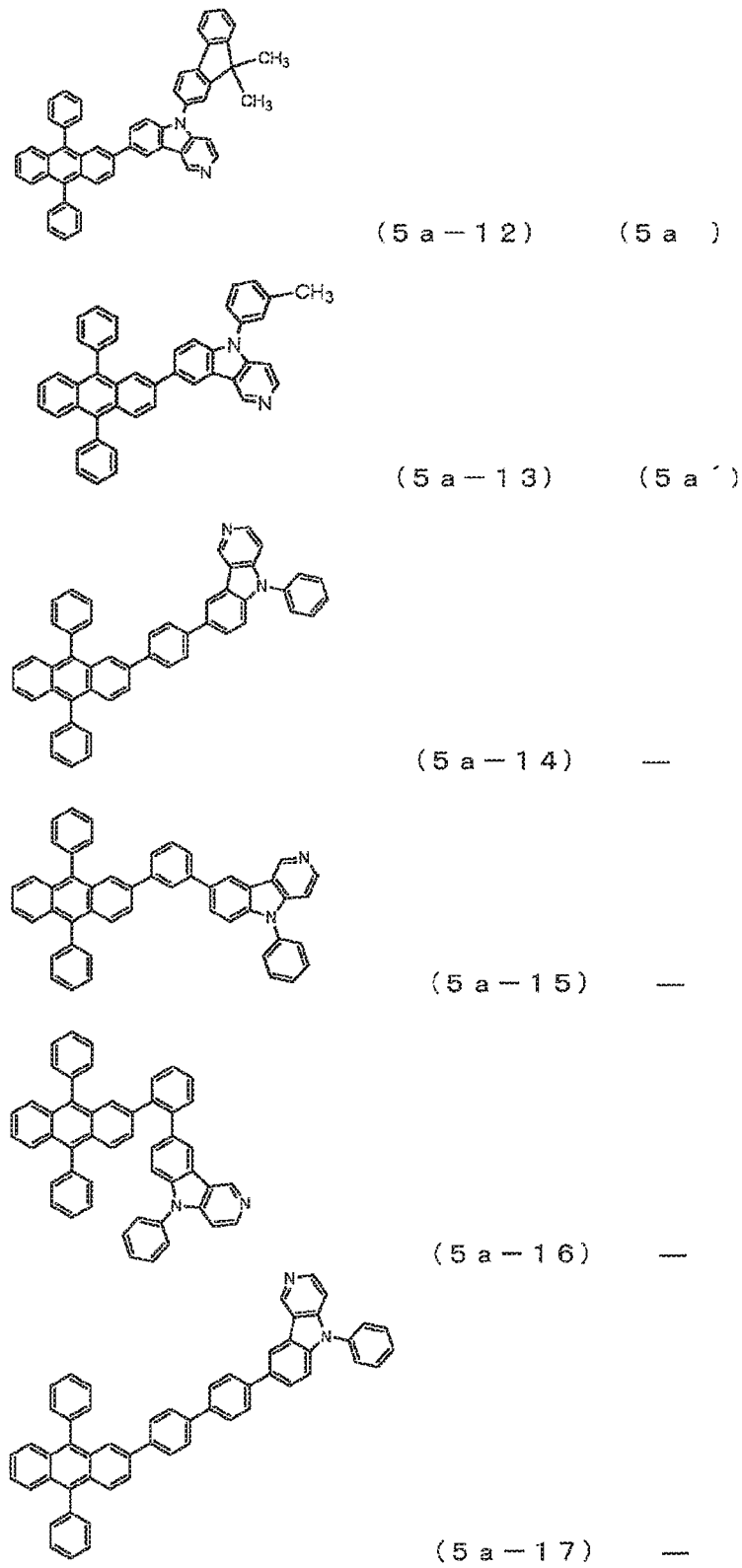
[FIG. 31] is a view showing the structural formulas of Compounds (5a-12) to (5a-17) in the anthracene derivative of the general formula (5a).
Figure 32:
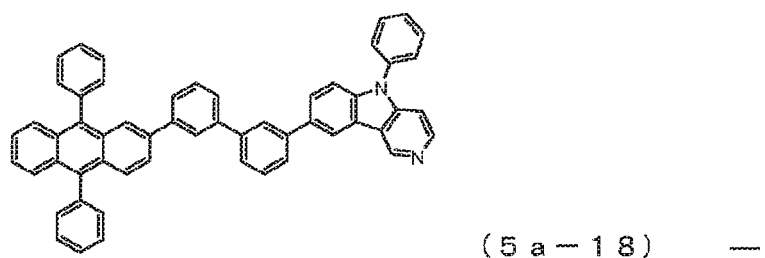
[FIG. 32] is a view showing the structural formulas of Compounds (5a-18) to (5a-20) in the anthracene derivative of the general formula (5a).
Figure 32:
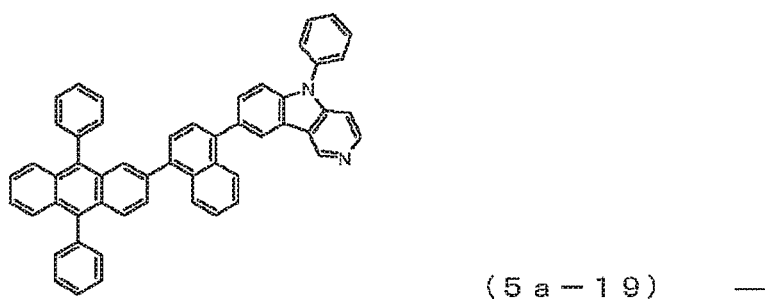
Figure 32:
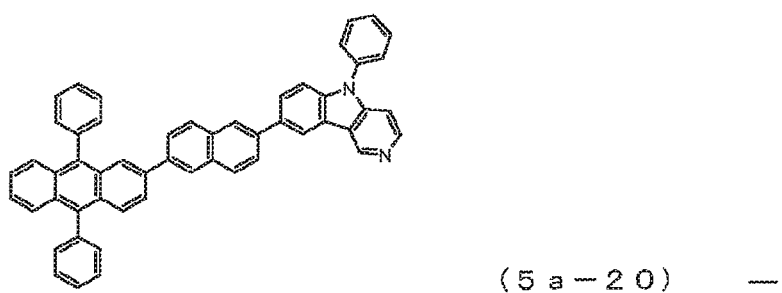

Alternatively, some of $R^{11}$ to $R^{14}$ may be detached and the remaining groups of $R^{11}$ to $R^{14}$ may be bonded to vacancies generated by the detachment via a substituted or unsubstituted methylene group, an oxygen atom, a sulfur atom, or a monoarylamino group to form a ring, for example, as in the compounds (3-1) to (3-6) in FIG. 21. Likewise, some of $R^{15}$ to $R^{18}$ may be detached and the remaining groups of $R^{15}$ to $R^{18}$ may be bonded to vacancies generated by the detachment via a substituted or unsubstituted methylene group, an oxygen atom, a sulfur atom, or a monoarylamino group to form a ring.

The aryl group in the monoarylamino group in this case can be exemplified by the same ones as those illustrated in relation to the aryl group in the monoarylamino group that can be present in the general formula (2). The aryl group in the monoarylamino group may be unsubstituted or substituted. Examples of the substituents can be exemplified by the same ones as those illustrated as the substituents optionally possessed by the aryl group in the monoarylamino group that can be present in the general formula (2). Modes which the substituents can adopt are also the same.

Preferred Embodiment of the General Formula (3)

As $A^2$, a divalent group of an aromatic hydrocarbon or a single bond is preferred, a divalent group resulting from the removal of two hydrogen atoms from benzene, biphenyl, or naphthalene or a single bond is more preferred, and a divalent group resulting from the removal of two hydrogen atoms from benzene or a single bond is particularly preferred.

As $Ar^6$, a phenyl group, a biphenylyl group, a naphthyl group, or an aromatic heterocyclic group is preferred, and an aromatic heterocyclic group is more preferred. The preferred examples of the aromatic heterocyclic group include a triazinyl group, a quinazolinyl group, a naphthopyrimidinyl group, a benzimidazolyl group, a pyridopyrimidinyl group, a naphthyridinyl group, a pyridyl group, a quinolyl group, an isoquinolyl group, a quinazolinyl group, or a benzoquinazolinyl group.

Concerning the preferred $R^{11}$ to $R^{14}$, an embodiment is preferred in which two adjacent groups, among $R^{11}$ to $R^{14}$, are an alkenyl group having 2 to 6 carbon atoms, an aromatic hydrocarbon group, or an aromatic heterocyclic group, and the two adjacent groups ($R^{11}$ to $R^{14}$) are bonded to each other via a single bond to form, together with a benzene ring to which $R^{11}$ to $R^{14}$ are bonded, a condensed ring. In this case, a vinyl group and a phenyl group are preferred as the alkenyl group having 2 to 6 carbon atoms, the aromatic hydrocarbon group, or the aromatic heterocyclic group. The preferred examples of the ring which is formed by the aromatic hydrocarbon group or the aromatic heterocyclic group together with the benzene ring to which $R^{11}$ to $R^{14}$ are bonded include a naphthalene ring, a phenanthrene ring, and a triphenylene ring.

An embodiment is also preferred in which, as indicated by the below-described general formulas (3a-1) to (3a-4) and (3b-1), any one of $R^{11}$ to $R^{14}$ is an aromatic hydrocarbon group or an aromatic heterocyclic group, another one of $R^{11}$ to $R^{14}$ is detached, thereby forming a vacancy, and the aromatic hydrocarbon group or the aromatic heterocyclic group is bonded to the vacancy via a substituted or unsubstituted methylene group, an oxygen atom, a sulfur atom, or a monoarylamino group to form a ring. The preferred examples of the aromatic hydrocarbon group or aromatic heterocyclic group in this case include a phenyl group, an indenyl group, an indolyl group, a benzofuranyl group, and a benzothienyl group. The preferred examples of the ring formed by the aromatic hydrocarbon group or the aromatic heterocyclic group and the benzene ring to which $R^{11}$ to $R^{14}$ are bonded include a fluorene ring, a carbazole ring, a dibenzofuran ring, a dibenzothiophene ring, an indenoindole ring, an indenobenzofuran ring, an indenobenzothiophene ring, a benzofuroindole ring, a benzothienoindole ring, and an indoloindole ring.

The compounds of the general formulas (3a-1) to (3b-1) are all novel compounds, and by using these compounds as materials for a luminous layer, it is possible to realize a high luminous efficiency.

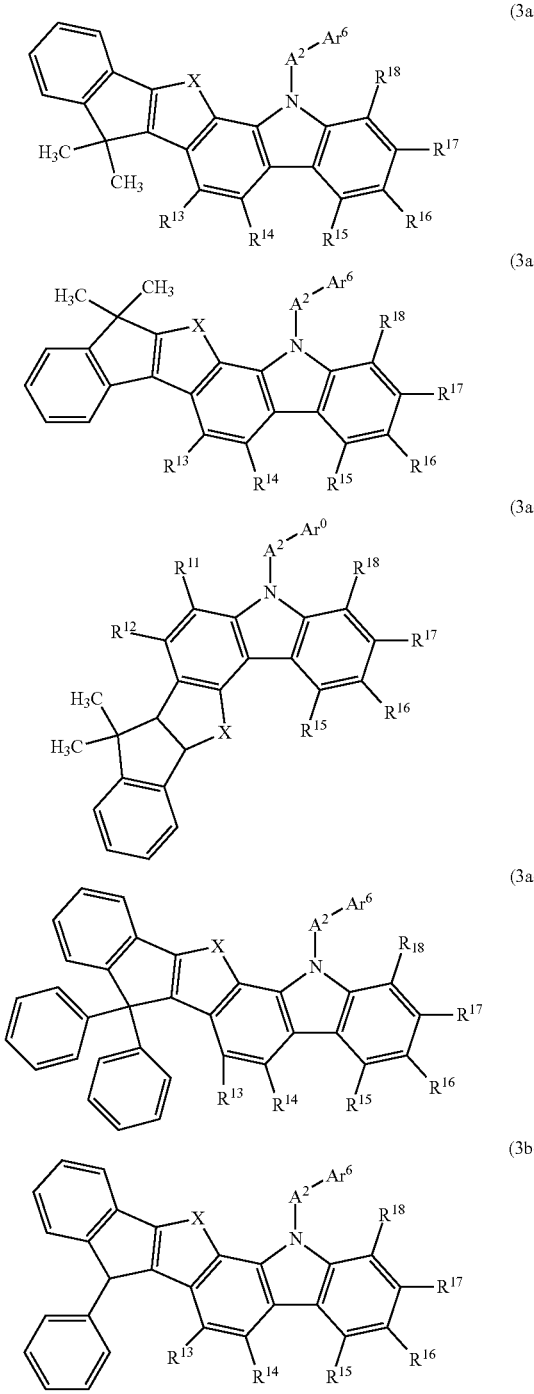

(3a-1)
(3a-2)
(3a-3)
(3a-4)
(3b-1)

wherein,

X represents a substituted or unsubstituted methylene group, an oxygen atom, a sulfur atom, or a monoarylamino group; and $A^2$, $Ar^6$, and $R^{11}$ to $R^{18}$ have the same meaning as that defined in the aforementioned general formula (3).

Concerning the preferred $R^{15}$ to $R^{18}$, an embodiment is preferred in which two adjacent groups or all groups, from among $R^{15}$ to $R^{18}$, are vinyl groups, and the two adjacent vinyl groups are bonded to each other via a single bond to form a condensed ring, that is, an embodiment in which $R^{15}$ to $R^{18}$ form a naphthalene ring or a phenanthrene ring together with the benzene ring to which $R^{15}$ to $R^{18}$ are bonded.

Alternatively, an embodiment is also preferred in which any one of $R^{15}$ to $R^{18}$ is an aromatic hydrocarbon group or an aromatic heterocyclic group. In this case, it is preferred that any one of $R^{15}$ to $R^{18}$ be a group selected from a fluorenyl group, a carbazolyl group, a dibenzofuranyl group, and a dibenzothienyl group, and it is more preferred that $R^{16}$ be a fluorenyl group, a carbazolyl group, a dibenzofuranyl group, or a dibenzothienyl group, and $R^{15}$, $R^{17}$, and $R^{18}$ be a hydrogen atom.

The preferred specific examples of the carbazole derivative of the general formula (3) can include compounds (3-1) to (3-23) having the structural formulas shown in FIG. 21 to FIG. 24, but the compound of the general formula (3) is not limited thereto. In the figures, it is also indicated whether each compound corresponds to any of the general formulas (3a-1) to (3a-4) and (3b-1). Whether there is no correspondence, the compound is marked "-".

The carbazole derivatives of the general formula (3) can be synthesized by a publicly known method or according thereto (see Patent Document 6). For example, as indicated in the below-described example, the synthesis can be performed by Suzuki coupling by using a compound having a structure corresponding to -$A^2$-$Ar^6$ and a halogen atom and a carbazole derivative having a hydrogen atom in a portion corresponding to -$A^2$-$Ar^6$ in the presence of a boron reagent such as tri-tert-butylphosphonium tetrafluoroborate, and a catalyst such as tris(dibenzylideneacetone)dipalladium.

The synthesized compound can be purified by column chromatography purification, adsorption purification with silica gel, activated carbon, or activated clay, recrystallization or crystallization with a solvent, a sublimation purification method, or the like. The compound to be used in the organic EL device of the present invention is finally purified by the sublimation purification method and supplied for use.

The indenoindole derivative of the general formula (2) or the carbazole derivative of the general formula (3) are used for the luminous layer of the organic EL device of the present invention, but a publicly known material can be used in addition thereto. The publicly known material can be exemplified by the following:

various metal complexes such as metal complexes including a quinolinol derivative such as $Alq_3$;
anthracene derivatives;
bis-styrylbenzene derivatives;
pyrene derivatives;
oxazole derivatives; and
polyparaphenylene vinylene derivatives.

In the present invention, the luminous layer may be composed of a host material and a dopant material.

The indenoindole derivative of the general formula (2) or the carbazole derivative of the general formula (3) is preferably used as the host material, but the aforementioned luminous materials, thiazole derivatives, benzimidazole derivatives, and polydialkylfluorene derivatives can be used.

Usable as the dopant material are, for example, quinacridone, coumarin, rubrene, perylene, pyrene, and derivatives thereof; benzopyran derivatives; indenophenanthrene derivatives; rhodamine derivatives; and aminostyryl derivatives.

A phosphorescent luminous material is preferably contained in the luminous layer in the present invention. A phosphorescent luminous body of a metal complex including iridium, platinum, or the like is preferred as the phosphorescent luminous material. Specific examples thereof include:
red phosphorescent luminous bodies, for example,
bis(3-methyl-2-phenylquinoline)iridium(III) acetylacetonate (Ir(3'-Mepq)$_2$(acac)),
Ir(piq)$_3$, and
Btp$_2$Ir(acac);
green phosphorescent luminous bodies, for example,
Ir(ppy)$_3$; and
blue phosphorescent luminous bodies, for example,
Flrpic, and
Flr6.
It is particularly preferred that a red phosphorescent luminous body be used as a dopant.

In this case, the indenoindole derivative of the general formula (2) or the carbazole derivative of the general formula (3) are preferred as the host material, but a quinazoline derivative can be used. Furthermore, a carbazole derivative, for example,
4,4'-di(N-carbazolyl)biphenyl (CBP),
TCTA, and
mCP
can be used as a hole injecting/transporting host material, and
p-bis(triphenylsilyl)benzene (UGH2),
2,2'2''-(1,3,5-phenylene)-tris(1-phenyl-1H-benzimidazole) (TPBI)
can be used as an electron transporting host material. By using such host material, a high-performance organic EL device can be produced.

The host material is preferably doped with the phosphorescent luminous material in an amount in a range of 1 to 30% by weight relative to the whole luminous layer by co-deposition to avoid concentration quenching.

A material which emits delayed fluorescence, such as a CDCB derivative, for example, PIC-TRZ, CC2Ta, PXZ-TRZ, and 4CzIPN, can be used as the luminous material (see Non Patent Document 1).

The above-described luminous layer is preferably formed by deposition or co-deposition of a gas including the indenoindole derivative of the general formula (2) or the carbazole derivative of the general formula (3), but the luminous layer can be also formed by a publicly known method such as a spin coat method and an ink jet method.

<Electron Transport Layer>

In the present invention, the electron transport layer (for example, the layer denoted by the reference numeral 7 in FIG. 1) provided on the above-described luminous layer can be formed by a publicly known method such as a vapor deposition method, a spin coat method, an ink jet method and the like by using a well-known electron transporting material.

Examples of the publicly known electron transport materials are presented hereinbelow:
various metal complexes such as metal complexes of quinolinol derivatives such as Alq$_3$ and BAlq;
triazole derivatives;
triazine derivatives;
oxadiazole derivatives;
pyridine derivatives;
pyrimidine derivatives;
benzimidazole derivatives;
thiadiazole derivatives;
anthracene derivatives;
carbodiimido derivatives;
quinoxaline derivatives;
pyridoindole derivatives;
phenanthroline derivatives; and
silole derivatives.

In the present invention, the electron transport layer is preferably formed by using a benzotriazole derivative represented by the following general formula (4) (can be referred to hereinbelow as "benzotriazole derivative of the general formula (4)") or an anthracene derivative represented by the following general formula (5) (can be referred to hereinbelow as "anthracene derivative of the general formula (5)") as the electron transport material.

The Benzotriazole Derivative Represented by the General Formula (4):

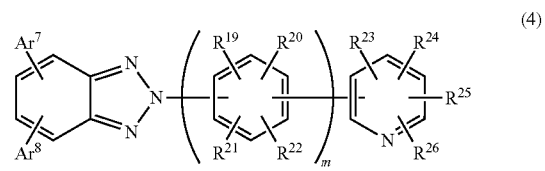

(4)

wherein,
Ar$^7$ represents an aromatic hydrocarbon group or an aromatic heterocyclic group;
Ar$^8$ represents a hydrogen atom, a deuterium atom, an aromatic hydrocarbon group or an aromatic heterocyclic group;
R$^{19}$ to R$^{26}$ each represent a hydrogen atom, a deuterium atom, a fluorine atom, a chlorine atom, a cyano group, an alkyl group having 1 to 6 carbon atoms, an aromatic hydrocarbon group, or an aromatic heterocyclic group;
m represents an integer of 0 to 2;
when m is 2, a plurality of existing R$^{19}$, R$^{20}$, R$^{21}$, and R$^{22}$ may be the same or different.

The benzotriazole derivative represented by the general formula (4) excels in electron injection and transport capacity and also excels in stability and durability of a thin film. By combining the electron transport layer formed from such a benzotriazole derivative with the hole transport layer including the above-described arylamine compound of the general formula (1), it is possible to inject holes and electrons into the luminous layer with good efficiency, thereby making it possible to ensure optimum carrier balance and greatly improve the characteristics of the organic EL device.

(Ar$^7$ and Ar$^8$ in the General Formula (4))

The aromatic hydrocarbon group or the aromatic heterocyclic group represented by Ar$^7$ and Ar$^8$ in the general formula (4) can be exemplified by the same ones as those illustrated in relation to the aromatic hydrocarbon group or the aromatic heterocyclic group represented by Ar$^1$ to Ar$^4$ in the general formula (1). These groups may be unsubstituted or may have a substituent. The substituents can be exemplified by the same ones as those illustrated as the substituents optionally possessed by the aromatic hydrocarbon group and the aromatic heterocyclic group represented by Ar$^1$ to Ar$^4$ in the general formula (1). Modes which the substituents can adopt are also the same.

(R$^{19}$ to R$^{26}$ in the General Formula (4))

The alkyl group having 1 to 6 carbon atoms which is represented by R$^{19}$ to R$^{26}$ in the general formula (4) may be straight-chain or branched. Specific examples of the alkyl group having 1 to 6 carbon atoms include a methyl group, an ethyl group, an n-propyl group, an isopropyl group, an n-butyl group, an isobutyl group, a tert-butyl group, an n-pentyl group, an isopentyl group, a neopentyl group, and an n-hexyl group, etc.

The alkyl group having 1 to 6 carbon atoms which is represented by $R^{19}$ to $R^{26}$ may be unsubstituted or may have a substituent. The following groups, in addition to a deuterium atom, a cyano group, and a nitro group, can exemplify the substituents:

a halogen atom, for example, a fluorine atom, a chlorine atom, a bromine atom, and an iodine atom;

an alkyloxy group having 1 to 6 carbon atoms, for example, a methyloxy group, an ethyloxy group, and a propyloxy group;

an alkenyl group, for example, a vinyl group and an allyl group;

an aryloxy group, for example, a phenyloxy group and a tolyloxy group;

an arylalkyloxy group, for example, a benzyloxy group and a phenethyloxy group;

an aromatic hydrocarbon group, for example, a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, and a triphenylenyl group;

an aromatic heterocyclic group, for example, a pyridyl group, a pyrimidinyl group, a triazinyl group, a thienyl group, a furyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, and a carbolinyl group.

These substituents may further have the substituents exemplified hereinabove. Further, these substituents may be present individually without forming a ring, or may be bonded to each other via a single bond, a substituted or unsubstituted methylene group, an oxygen atom, or a sulfur atom to form a ring.

Among the abovementioned substituents, alkyloxy groups having 1 to 6 carbon atoms may be straight-chain or branched.

The aromatic hydrocarbon group or the aromatic heterocyclic group, which is represented by $R^{19}$ to $R^{26}$ in the general formula (4), can be exemplified by the same ones as those illustrated in relation to the aromatic hydrocarbon group or the aromatic heterocyclic group, which is represented by $Ar^1$ to $Ar^4$ in the general formula (1). These groups may be unsubstituted or may have a substituent. The substituents can be exemplified by the same ones as those illustrated as the substituents optionally possessed by the aromatic hydrocarbon group and the aromatic heterocyclic group, which are represented by $Ar^1$ to $Ar^4$ in the general formula (1). Modes which the substituents can adopt are also the same.

$R^{19}$ to $R^{26}$ may be present individually without forming a ring, or may be bonded to each other via a single bond, a substituted or unsubstituted methylene group, an oxygen atom, or a sulfur atom to form a ring.

Preferred Embodiment of the General Formula (4)

As $Ar^7$, an aromatic hydrocarbon group or a carbazolyl group is preferred, and a phenyl group, a biphenylyl group, a terphenylyl group, a naphthyl group, an anthracenyl group, a phenanthrenyl group, a fluorenyl group, a pyrenyl group, a triphenylenyl group, or an N-phenylcarbazolyl group is more preferred.

As $Ar^8$, a hydrogen atom, a deuterium atom, an aromatic hydrocarbon group, or a carbazolyl group is preferred, a hydrogen atom, a deuterium group, a phenyl group, a biphenylyl group, a terphenylyl group, a naphthyl group, an anthracenyl group, a phenanthrenyl group, a fluorenyl group, a pyrenyl group, a triphenylenyl group, or an N-phenylcarbazolyl group is more preferred, a hydrogen atom or a deuterium atom is particularly preferred, and a hydrogen atom is most preferred.

Further, when $Ar^8$ is an aromatic hydrocarbon group or an aromatic heterocyclic group, from the standpoint of synthesis, it is preferred that $Ar^8$ be the same group as $Ar^7$.

As the substituents that are optionally possessed by $Ar^7$ and $Ar^8$, an aromatic hydrocarbon group, a quinolyl group, or an isoquinolyl group is preferred, and a phenyl group, a biphenylyl group, a terphenylyl group, a tetrakisphenyl group, a styryl group, a naphthyl group, an anthracenyl group, an acenaphthenyl group, a phenanthrenyl group, a fluorenyl group, an indenyl group, a pyrenyl group, a triphenylenyl group, a quinolyl group, or an isoquinolyl group is more preferred.

It is preferred that m be 1. When m=1, as the bonding position of the benzene ring in the pyridine ring, it is preferred that the benzene ring be bonded at the 3-position or 4-position in the pyridine ring, as shown in the following general formulas (4a) and (4b). Further, when m=1, as the positional relationship of the pyridine ring and benzotriazole in the benzene ring, it is preferred that the benzotriazole ring be bonded at a para-position or meta-position in the benzene ring to the pyridine ring, as shown in the following general formulas (4c) and (4d).

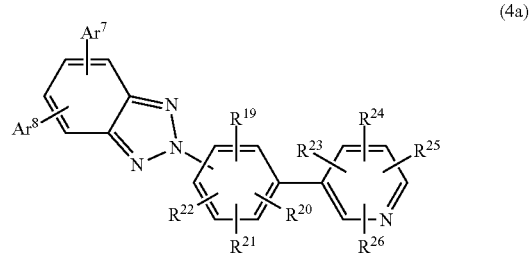

(4a)

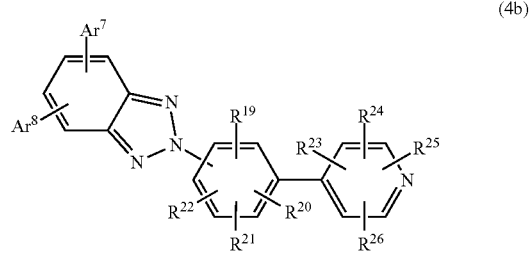

(4b)

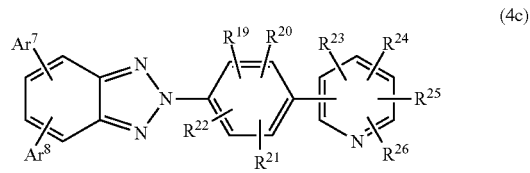

(4c)

-continued

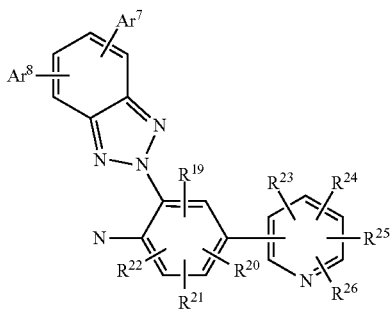
(4d)

wherein,

Ar⁷, Ar⁸, and $R^{19}$ to $R^{26}$ have the same meaning as that defined in the aforementioned general formula (4).

The preferred specific examples of the benzotriazole derivative of the general formula (4) can include the compounds (4-1) to (4-20) having the structural formulas shown in FIG. 25 to FIG. 28, but the compound of the general formula (4) is not limited thereto. In the figures, it is also indicated whether each compound corresponds to any of the general formulas (4a) to (4d).

The benzotriazole derivative of the general formula (4) can be synthesized by a publicly known method (see Patent Document 7).

The synthesized compound can be purified by column chromatography purification, adsorption purification with silica gel, activated carbon, or activated clay, recrystallization or crystallization with a solvent, a sublimation purification method, or the like. The compound to be used in the organic EL device of the present invention is finally purified by the sublimation purification method and supplied for use. The Anthracene Derivative Represented by the General Formula (5):

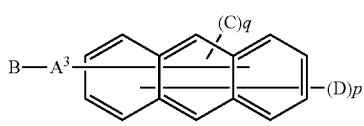
(5)

wherein, in p and q, p is an integer of 7 or 8 and q is an integer of 1 or 2, provided that a sum of p and q is 9;

$A^3$ represents a divalent group of an aromatic hydrocarbon, a divalent group of an aromatic heteroclic ring, or a single bond;

B represents an aromatic heterocyclic group;

C represents an aromatic hydrocarbon group or an aromatic heterocyclic group; when q is 2, a plurality of present C may be the same or different; and D represents a hydrogen atom, a deuterium atom, a fluorine atom, a chlorine atom, a cyano group, or an alkyl group having 1 to 6 carbon atoms, a plurality of present D may be the same or different.

As can be understood from the general formula (5), the anthracene derivative has a molecular structure in which the anthracene ring and the group B are connected by a divalent group or a single bond. One or two monovalent aromatic hydrocarbon groups or monovalent aromatic heterocyclic groups (group C) is bonded as a substituent to the anthracene ring to which the group B is connected.

The anthracene derivative represented by the general formula (5) excels in electron injection and transport capacity and also excels in stability and durability of a thin film. By combining the electron transport layer formed from such an anthracene derivative with the hole transport layer including the above-described arylamine compound of the general formula (1), it is possible to inject holes and electrons into the luminous layer with good efficiency, thereby making it possible to ensure optimum carrier balance and greatly improve the characteristics of the organic EL device.

($A^3$ in the General Formula (5))

The divalent group of an aromatic hydrocarbon or the divalent group of an aromatic heteroclic ring represented by $A^3$ in the general formula (5) can be exemplified by the same ones as those illustrated in relation to the divalent group of an aromatic hydrocarbon or the divalent group of an aromatic heteroclic ring represented by $A^1$ in the general formula (2). These divalent groups may be unsubstituted, or may have a substituent that can be introduced, provided that excellent properties of the anthracene derivative are not impaired. The substituents can be exemplified by the same ones as those illustrated as the substituents optionally possessed by the aromatic hydrocarbon group and the aromatic heterocyclic group represented by $Ar^1$ to $Ar^4$ in the general formula (1). Modes which the substituents can adopt are also the same.

(B in the General Formula (5))

Specific examples of the aromatic heterocyclic group represented by B in the general formula (5) include a pyridyl group, a pyrimidinyl group, a furyl group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, and a carbolinyl group, etc.

The aromatic heterocyclic group represented by B may be unsubstituted, or may have a substituent that can be introduced, provided that excellent properties of the anthracene derivative of the general formula (5) are not impaired. The following groups, in addition to a deuterium atom, a cyano group, and a nitro group, can exemplify the substituents.

a halogen atom, for example, a fluorine atom, a chlorine atom, a bromine atom, and an iodine atom;

an alkyl group having 1 to 6 carbon atoms, for example, a methyl group, an ethyl group, an n-propyl group, an isopropyl group, an n-butyl group, an isobutyl group, a tert-butyl group, an n-pentyl group, an isopentyl group, a neopentyl group, and an n-hexyl group;

a cycloalkyl group having 5 to 10 carbon atoms, for example, a cyclopentyl group, a cyclohexyl group, a 1-adamantyl group, and a 2-adamantyl group;

an alkyloxy group having 1 to 6 carbon atoms, for example, a methyloxy group, an ethyloxy group, and a propyloxy group;

a cycloalkyloxy group having 5 to 10 carbon atoms, for example, a cyclopentyloxy group, a cyclohexyloxy group, a 1-adamantyloxy group, and a 2-adamantyloxy group;

an alkenyl group, for example, a vinyl group and an allyl group;

an aryloxy group, for example, a phenyloxy group and a tolyloxy group;

an arylalkyloxy group, for example, a benzyloxy group and a phenethyloxy group;

an aromatic hydrocarbon group, for example, a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, and a triphenylenyl group;

an aromatic heterocyclic group, for example, a pyridyl group, a furyl group, a thienyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, and a carbolinyl group;

an aryloxy group, for example, a phenyloxy group, a biphenylyloxy group, a naphthyloxy group, an anthryloxy group, and a phenanthrenyloxy group;

an arylvinyl group, for example, a styryl group and a naphthylvinyl group; and an acyl group, for example, an acetyl group and a benzoyl group.

These substituents may further have the substituents exemplified hereinabove. Further, these substituents may be present individually without forming a ring, or may be bonded to each other via a single bond, a substituted or unsubstituted methylene group, an oxygen atom, or a sulfur atom to form a ring.

Among the abovementioned substituents, alkyl groups having 1 to 6 carbon atoms and alkyloxy groups having 1 to 6 carbon atoms may be straight-chain or branched.

(C in the General Formula (5))

The aromatic hydrocarbon group or the aromatic heterocyclic group represented by C in the general formula (5) can be exemplified by the same ones as those illustrated in relation to the aromatic hydrocarbon group or the aromatic heterocyclic group represented by $Ar^1$ to $Ar^4$ in the general formula (1). When a plurality of such groups are bonded to the same anthracene ring (when q is 2), the plurality of present C may be the same or different. These groups may be unsubstituted or may have a substituent. The substituents can be exemplified by the same ones as those illustrated in relation to the substituents that are optionally possessed by the aromatic hydrocarbon group and the aromatic heterocyclic group represented by $Ar^1$ to $Ar^4$ in the general formula (1). Modes which the substituents can adopt are also the same.

(D in the General Formula (5))

The alkyl group having 1 to 6 carbon atoms, which is represented by D in the general formula (5), may be straight-chain or branched. Specific examples of the alkyl group having 1 to 6 carbon atoms include a methyl group, an ethyl group, an n-propyl group, an isopropyl group, an n-butyl group, an isobutyl group, a tert-butyl group, an n-pentyl group, an isopentyl group, a neopentyl group, and an n-hexyl group, etc.

The plurality of present D may be the same or different. These groups may be present individually without forming a ring, or may be bonded to each other via a single bond, a substituted or unsubstituted methylene group, an oxygen atom, or a sulfur atom to form a ring.

Preferred Embodiment of the General Formula (5)

As $A^3$, divalent group of an aromatic hydrocarbon or a single bond is preferred, a divalent group derived from benzene, biphenyl, terphenyl, naphthalene, anthracene, fluorene, or phenanthrene or a single bond is more preferred, and a divalent group derived from benzene, biphenyl, naphthalene, fluorine, or phenanthrene or a single bond is particularly preferred.

As B, an aromatic heterocyclic group, more specifically, a pyridyl group, a pyrimidinyl group, a pyrrolyl group, a quinolyl group, an isoquinolyl group, an indolyl group, a carbazolyl group, a benzoxazolyl group, a benzothiazolyl group, a quinoxalinyl group, a benzimidazolyl group, a pyrazolyl group, a carbolinyl group, etc. are preferred, and a pyridyl group, a pyrimidinyl group, a quinolyl group, an isoquinolyl group, an indolyl group, a benzimidazolyl group, and a pyrazolyl group, or a carbolinyl group is more preferred.

As substituents of B, an aromatic hydrocarbon group is preferred, and a phenyl group, a biphenyl group, a phenanthrenyl group, an anthracenyl group, and a fluorenyl group are particularly preferred.

As C, an aromatic hydrocarbon group is preferred, and a phenyl group, a biphenylyl group, a naphthyl group, an anthracenyl group, or a phenanthrenyl group is more preferred.

It is preferred that in the general formula (5), B be a nitrogen-containing heterocyclic ring and D be a hydrogen atom. The anthracene derivative of such a preferred embodiment is particularly represented by the following general formulas (5a), (5b), or (5c).

The Anthracene Derivative Represented by the General Formula (5a);

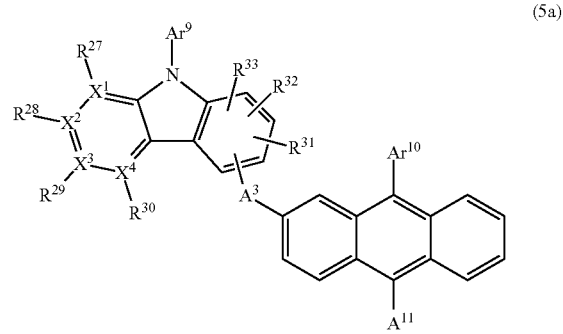

(5a)

wherein, $A^3$ has the same meaning as that defined in the aforementioned general formula (5);

$Ar^9$ to $Ar^{11}$ each represent an aromatic hydrocarbon group or an aromatic heterocyclic group;

$R^{27}$ to $R^{33}$ are each a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, or an aryloxy group and may be bonded to each other via a single bond, a substituted or unsubstituted methylene group, an oxygen atom, or a sulfur atom to form a ring; and $X^1$ to $X^4$ represent a carbon atom or a nitrogen atom, only any one of $X^1$ to $X^4$ is a nitrogen atom, and none of $R^{27}$ to $R^{30}$, including a hydrogen atom, is bonded to the nitrogen atom.

The nitrogen-containing heterocyclic ring of a three-ring structure to which $A^3$ is bonded corresponds to the group B in the general formula (5). $Ar^9$ is a substituent bonded to the nitrogen-containing aromatic ring, and $Ar^{10}$ and $Ar^{11}$ correspond to C in the general formula (5) (that is q=2).

$Ar^9$ to $Ar^{11}$:

The aromatic hydrocarbon group or the aromatic heterocyclic group represented by $Ar^9$ to $Ar^{11}$ in the general formula (5a) can be exemplified by the same ones as those illustrated in relation to the aromatic hydrocarbon group or the aromatic heterocyclic group represented by $Ar^1$ to $Ar^4$ in the general formula (1). These groups may be unsubstituted or may have a substituent. The substituents can be exemplified by the same ones as those illustrated as the substituents optionally possessed by the aromatic hydrocarbon group and the aromatic heterocyclic group represented by $Ar^1$ to $Ar^4$ in the general formula (1). Modes which the substituents can adopt are also the same.

As $Ar^9$ to $Ar^{11}$, an aromatic hydrocarbon group is preferred, and a phenyl group, a biphenylyl group, a naphthyl group, an anthracenyl group, a phenanthrenyl group, or a fluorenyl group is more preferred.

$R^{27}$ to $R^{33}$:

The alkyl group having 1 to 6 carbon atoms, the cycloalkyl group having 5 to 10 carbon atoms, or the alkenyl group having 2 to 6 carbon atoms, which is represented by $R^{27}$ to $R^{33}$ in the general formula (5a), can be exemplified by the same ones as those illustrated in relation to the alkyl group having 1 to 6 carbon atoms, the cycloalkyl group having 5 to 10 carbon atoms, or the alkenyl group having 2 to 6 carbon atoms, which is represented by $R^1$ to $R^8$ in the general formula (2). These groups may be unsubstituted or may have a substituent. The substituents can be exemplified by the same ones as those illustrated as the substituents optionally possessed by the alkyl group having 1 to 6 carbon atoms, the cycloalkyl group having 5 to 10 carbon atoms, and the alkenyl group having 2 to 6 carbon atoms which are represented by $R^1$ to $R^8$ in the general formula (2). Modes which the substituents can adopt are also the same.

The alkyloxy group having 1 to 6 carbon atoms or the cycloalkyloxy group having 5 to 10 carbon atoms, which is represented by $R^{27}$ to $R^{33}$ in the general formula (5a), can be exemplified by the same ones as those illustrated in relation to the alkyloxy group having 1 to 6 carbon atoms or the cycloalkyloxy group having 5 to 10 carbon atoms which is represented by $R^1$ to $R^8$ in the general formula (2). These groups may be unsubstituted or may have a substituent. The substituents can be exemplified by the same ones as those illustrated as the substituents optionally possessed by the alkyl group having 1 to 6 carbon atoms, the cycloalkyl group having 5 to 10 carbon atoms, and the alkenyl group having 2 to 6 carbon atoms which are represented by $R^1$ to $R^8$ in the general formula (2). Modes which the substituents can adopt are also the same.

The aromatic hydrocarbon group or the aromatic heterocyclic group, which is represented by $R^{27}$ to $R^{33}$ in the general formula (5a), can be exemplified by the same ones as those illustrated in relation to the aromatic hydrocarbon group or the aromatic heterocyclic group, which is represented by $Ar^1$ to $Ar^4$ in the general formula (1). These groups may be unsubstituted or may have a substituent. The substituents can be exemplified by the same ones as those illustrated as the substituents optionally possessed by the aromatic hydrocarbon group and the aromatic heterocyclic group, which are represented by $Ar^1$ to $Ar^4$ in the general formula (1). Modes which the substituents can adopt are also the same.

The aryloxy group, which is represented by $R^{27}$ to $R^{33}$ in the general formula (5a), can be exemplified by the same ones as those illustrated in relation to the aryloxy group, which is represented by $R^1$ to $R^8$ in the general formula (2). These groups may be unsubstituted or may have a substituent. The substituents can be exemplified by the same ones as those illustrated as the substituents optionally possessed by the aromatic hydrocarbon group and the aromatic heterocyclic group, which are represented by $Ar^1$ to $Ar^4$ in the general formula (1). Modes which the substituents can adopt are also the same.

$R^{27}$ to $R^{33}$ may be present individually without forming a ring, or may be bonded to each other via a single bond, a substituted or unsubstituted methylene group, an oxygen atom, or a sulfur atom to form a ring.

$X^1$ to $X^4$:

$X^1$, $X^2$, $X^3$, and $X^4$ in the general formula (5a) are endocyclic elements constituting part of the abovementioned nitrogen-containing heterocyclic ring, and each represent a carbon atom or a nitrogen atom, provided that only any one of them is a nitrogen atom. $R^1$ to $R^7$ and $Ar^9$ represent groups bonded to the nitrogen-containing heterocyclic ring.

Thus, in the ring formed by $X^1$, $X^2$, $X^3$, and $X^4$, $R^1$ to $R^4$ are shown as substituents, but when the endocyclic element is a nitrogen atom, it is assumed that none of $R^1$ to $R^4$ (including a hydrogen atom) is bonded to the nitrogen atom. For example, it means that when $X^1$ is a nitrogen atom, $R^{27}$ is not present, when $X^2$ is a nitrogen atom, $R^{28}$ is not present, when $X^3$ is a nitrogen atom, $R^{29}$ is not present, and when $X^4$ is a nitrogen atom, $R^{30}$ is not present.

It is preferred that only $X^3$ be a nitrogen atom ($X^1$, $X^2$, and $X^4$ are carbon atoms, and the group $R^{29}$ is not present). It is more preferred that, only $X^3$ be a nitrogen atom, $A^3$ be a single bond, and $A^3$ be bonded at the para-position to the nitrogen atom in the benzene ring, as represented by the following general formula (5a').

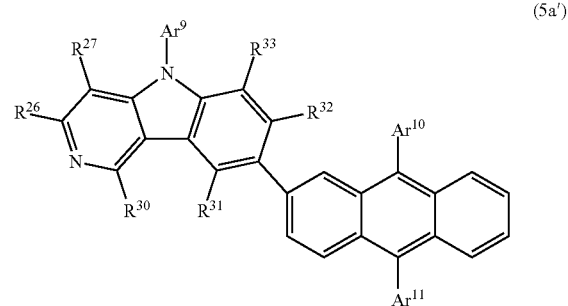

(5a')

wherein $Ar^9$ to $Ar^{11}$, $R^{27}$, $R^{28}$, and $R^{30}$ to $R^{33}$ have the same meaning as that defined in the aforementioned general formula (5a).

The preferred specific examples of the anthracene derivative of the general formula (5a) can include compounds (5a-1) to (5a-20) having the structural formulas shown in FIG. 29 to FIG. 32, but the compound of the general formula (5a) is not limited thereto. In the figures, it is also indicated whether each compound corresponds to the general formula (5a'). Whether there is no correspondence, the compound is marked "-".

The Anthracene Derivative Represented by the General Formula (5b);

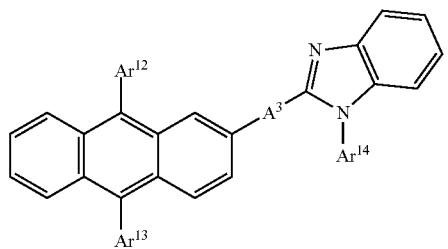

(5b)

wherein, $A^3$ has the same meaning as that defined in the aforementioned general formula (5); and $Ar^{12}$ to $Ar^{14}$ each are an aromatic hydrocarbon group or an aromatic heterocyclic group.

$Ar^{12}$ and $Ar^{13}$ in the general formula (5b) correspond to C in the general formula (5) (that is, q=2), and the nitrogen containing aromatic heterocyclic ring to which $A^3$ is bonded corresponds to the group B of the general formula (5). $Ar^{14}$ is a substituent bonded to the nitrogen-containing aromatic heterocyclic ring.

$Ar^{12}$ to $Ar^{14}$:

The aromatic hydrocarbon group or the aromatic heterocyclic group represented by $Ar^{12}$ to $Ar^{14}$ in the general formula (5b) can be exemplified by the same ones as those illustrated in relation to the aromatic hydrocarbon group or the aromatic heterocyclic group represented by $Ar^1$ to $Ar^4$ in the general formula (1). These groups may be unsubstituted or may have a substituent. The substituents can be exemplified by the same ones as those illustrated in relation to the substituents that are optionally possessed by the aromatic hydrocarbon group and the aromatic heterocyclic group represented by $Ar^1$ to $Ar^4$ in the general formula (1). Modes which the substituents can adopt are also the same.

As $Ar^{12}$ to $Ar^{14}$, an aromatic hydrocarbon group is preferred, and a phenyl group, a biphenylyl group, a naphthyl group, an anthracenyl group, a phenanthrenyl group, or a fluorenyl group is more preferred.

Figure 33:
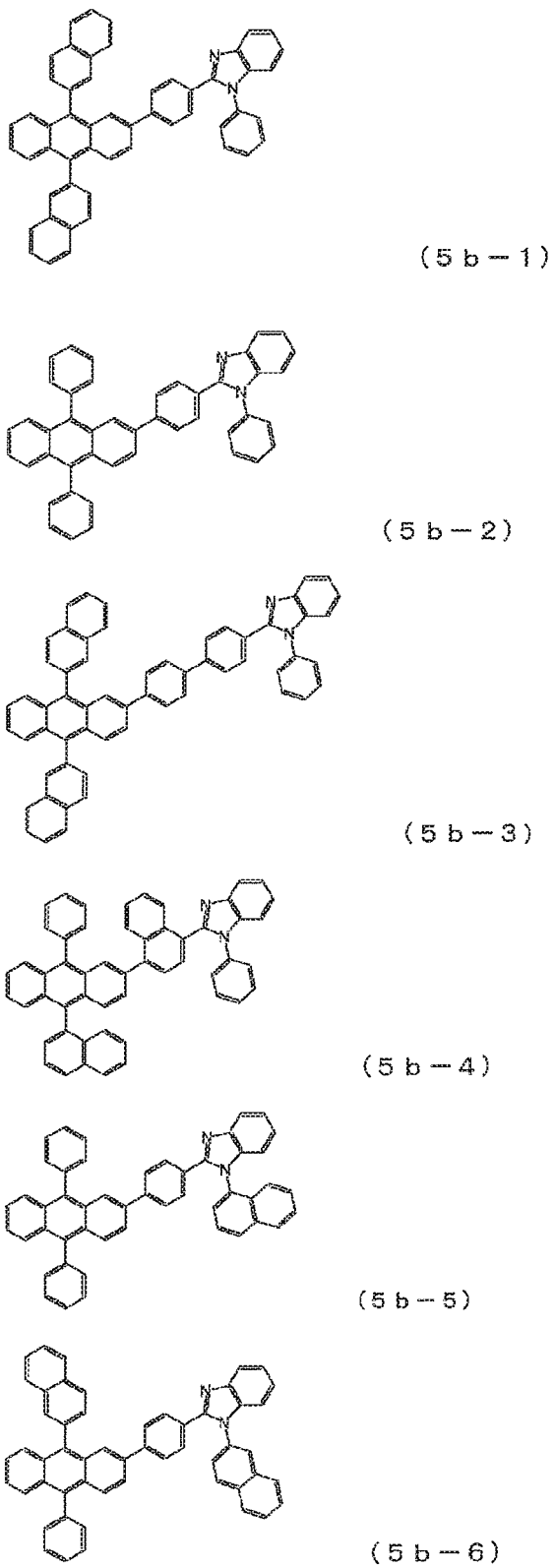
[FIG. 33] is a view showing the structural formulas of Compounds (5b-1) to (5b-6) in the anthracene derivative of the general formula (5b).
Figure 34:
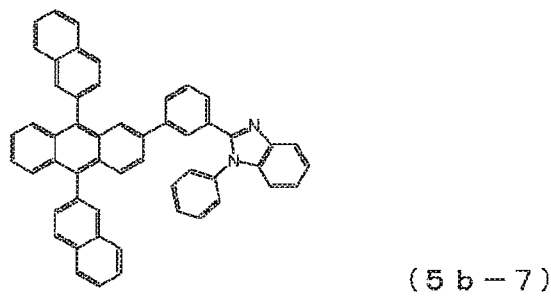
[FIG. 34] is a view showing the structural formulas of Compounds (5b-7) to (5b-11) in the anthracene derivative of the general formula (5b).
Figure 34:
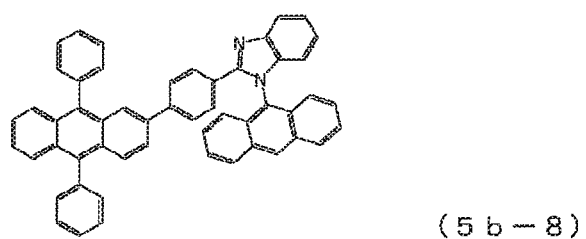
Figure 34:
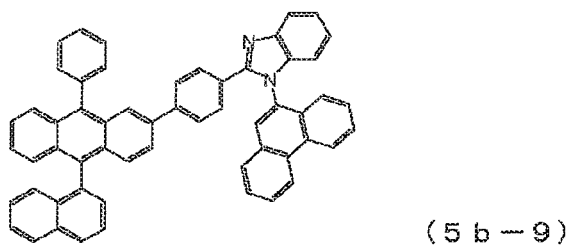
Figure 34:
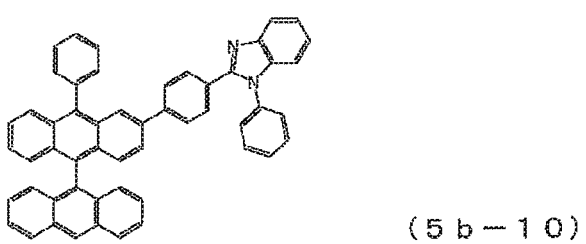
Figure 34:
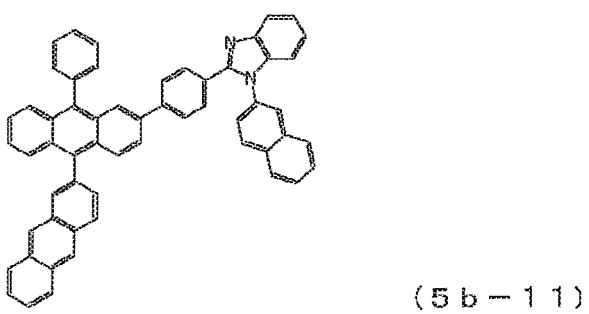
Figure 35:
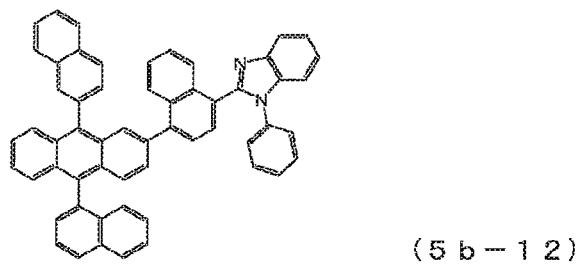
[FIG. 35] is a view showing the structural formulas of Compounds (5b-12) to (5b-16) in the anthracene derivative of the general formula (5b).
Figure 35:
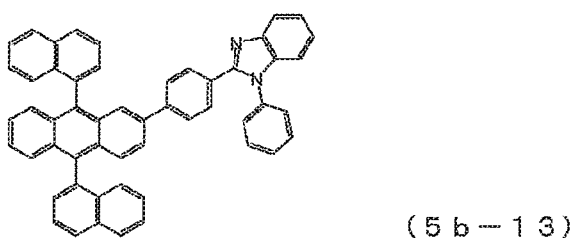
Figure 35:
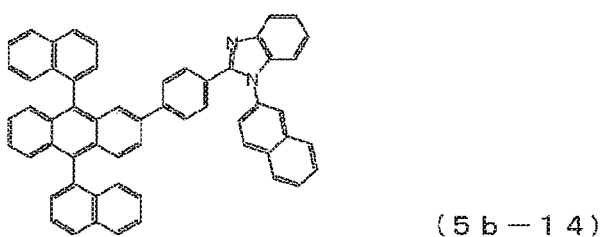
Figure 35:
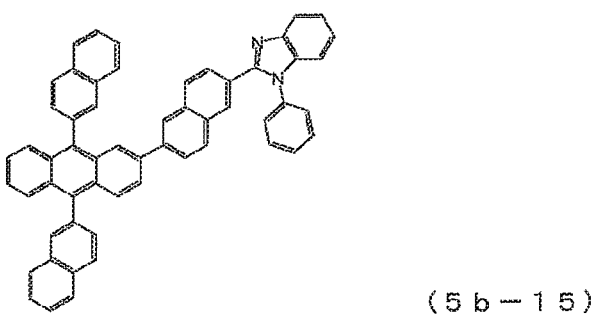
Figure 35:
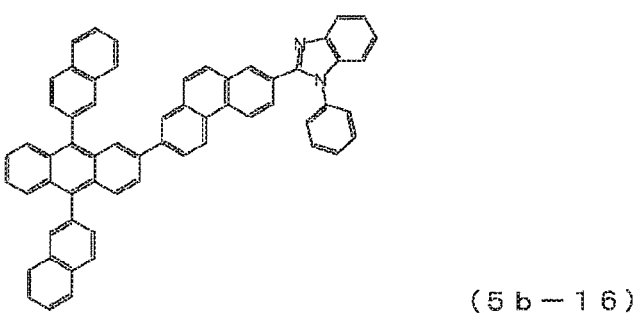
Figure 36:
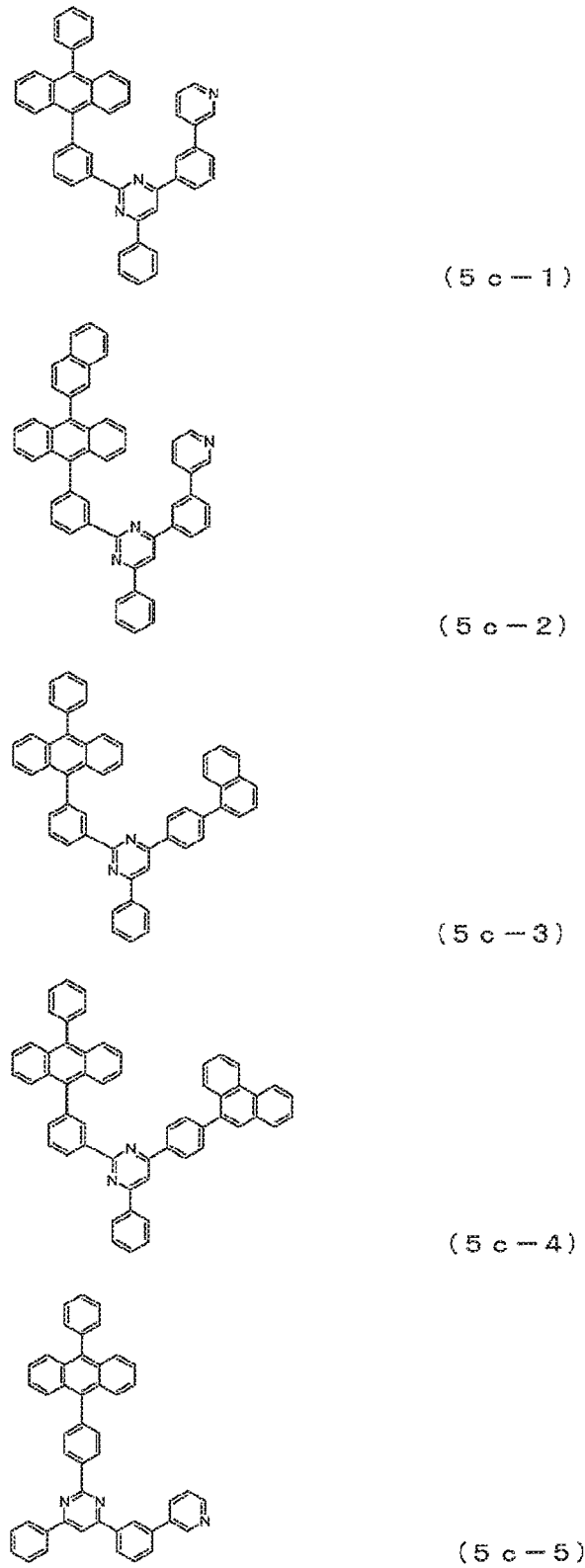
[FIG. 36] is a view showing the structural formulas of Compounds (5c-1) to (5c-5) in the anthracene derivative of the general formula (5c).
Figure 37:
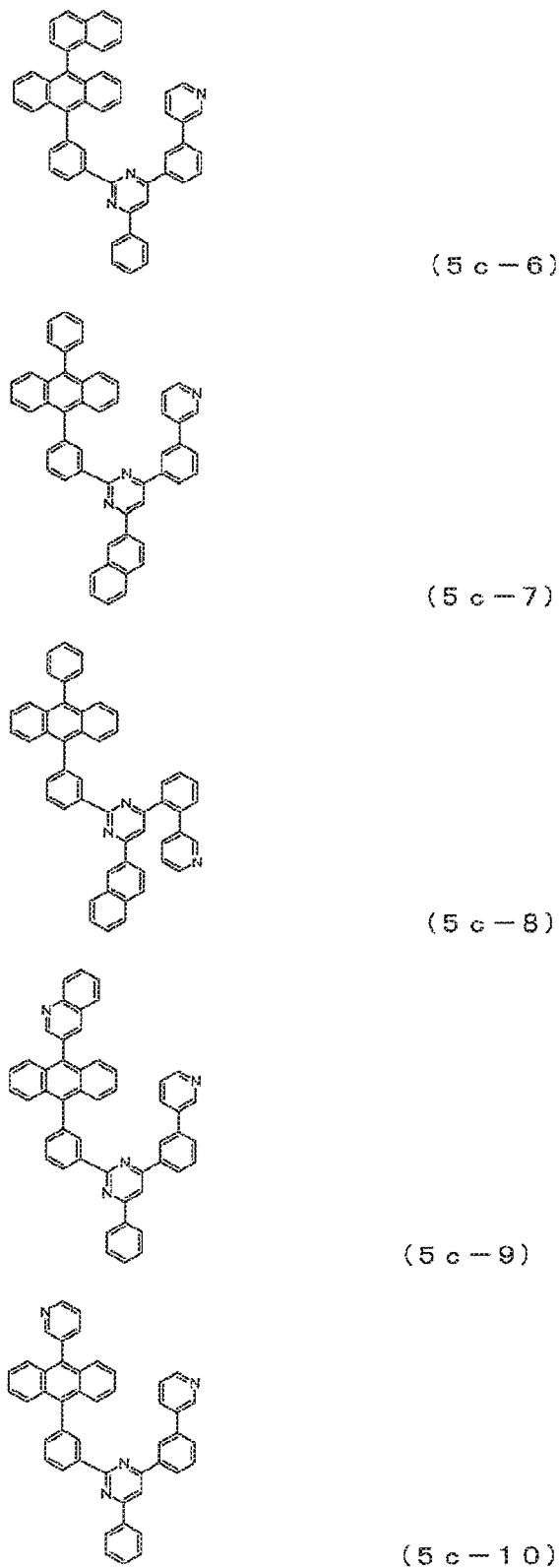
[FIG. 37] is a view showing the structural formulas of Compounds (5c-6) to (5c-10) in the anthracene derivative of the general formula (5c).
Figure 38:
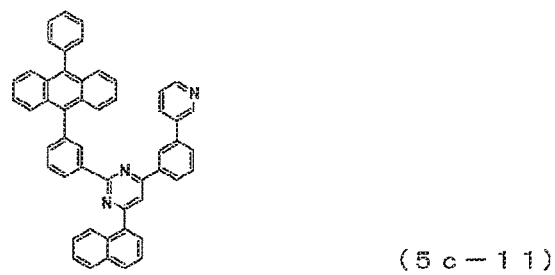
[FIG. 38] is a view showing the structural formulas of Compounds (5c-11) to (5c-15) in the anthracene derivative of the general formula (5c).
Figure 38:
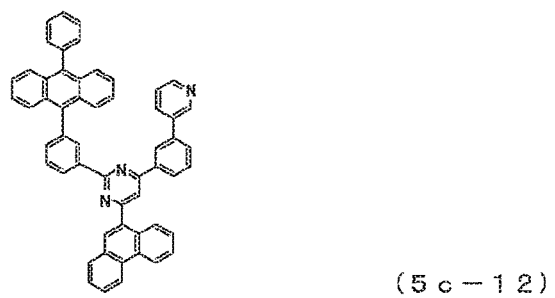
Figure 38:
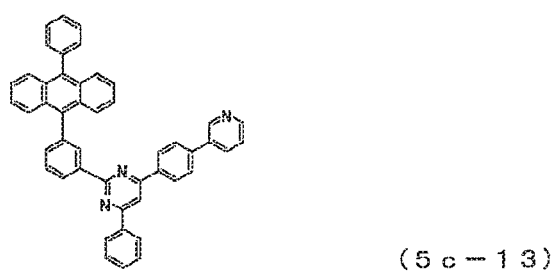
Figure 38:
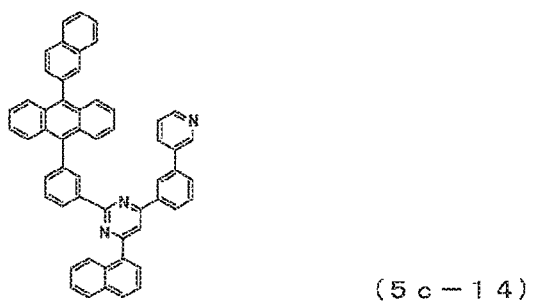
Figure 38:
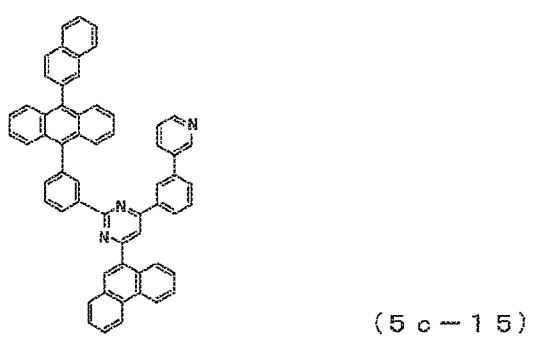
Figure 39:
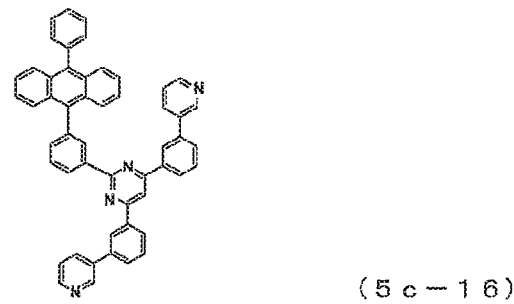
[FIG. 39] is a view showing the structural formulas of Compounds (5c-16) to (5c-20) in the anthracene derivative of the general formula (5c).
Figure 39:
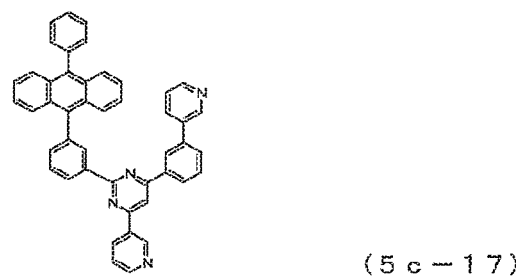
Figure 39:
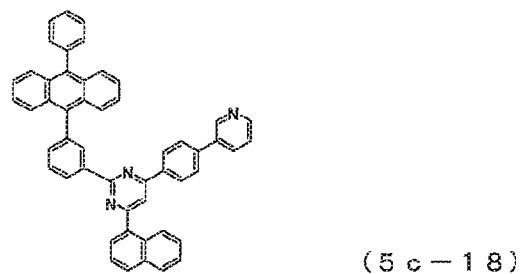
Figure 39:
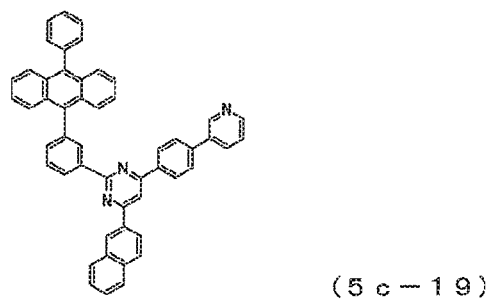
Figure 39:
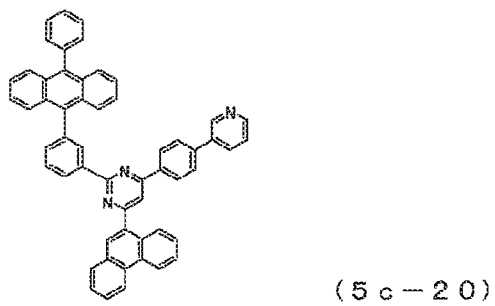
Figure 40:
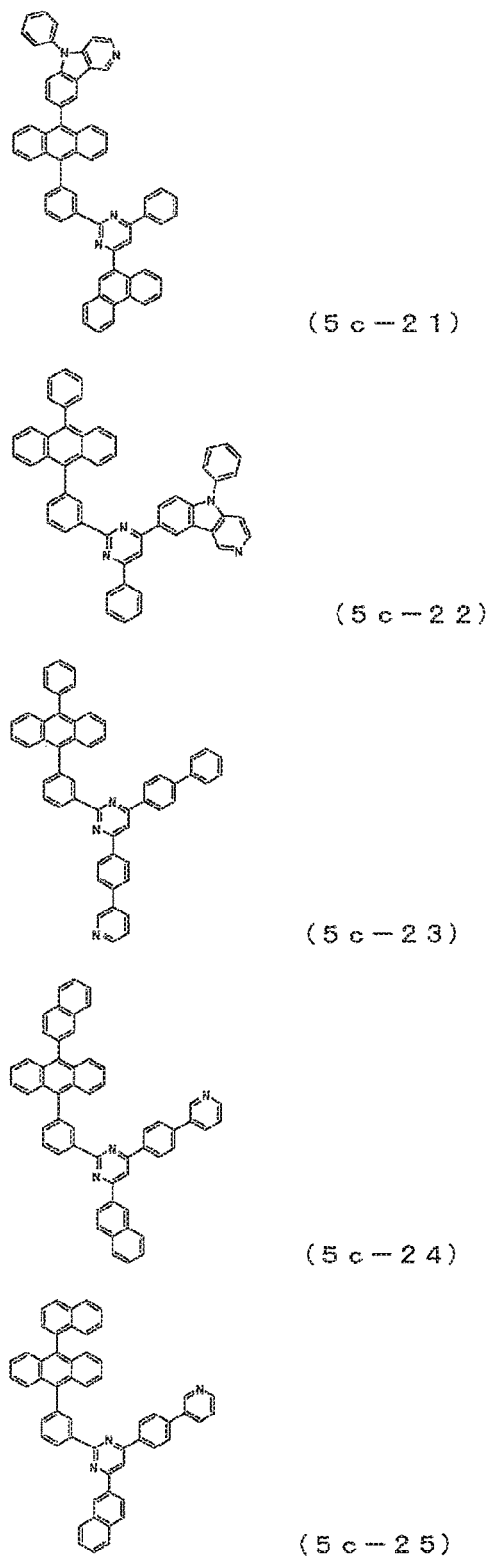
[FIG. 40] is a view showing the structural formulas of Compounds (5c-21) to (5c-25) in the anthracene derivative of the general formula (5c).
Figure 41:
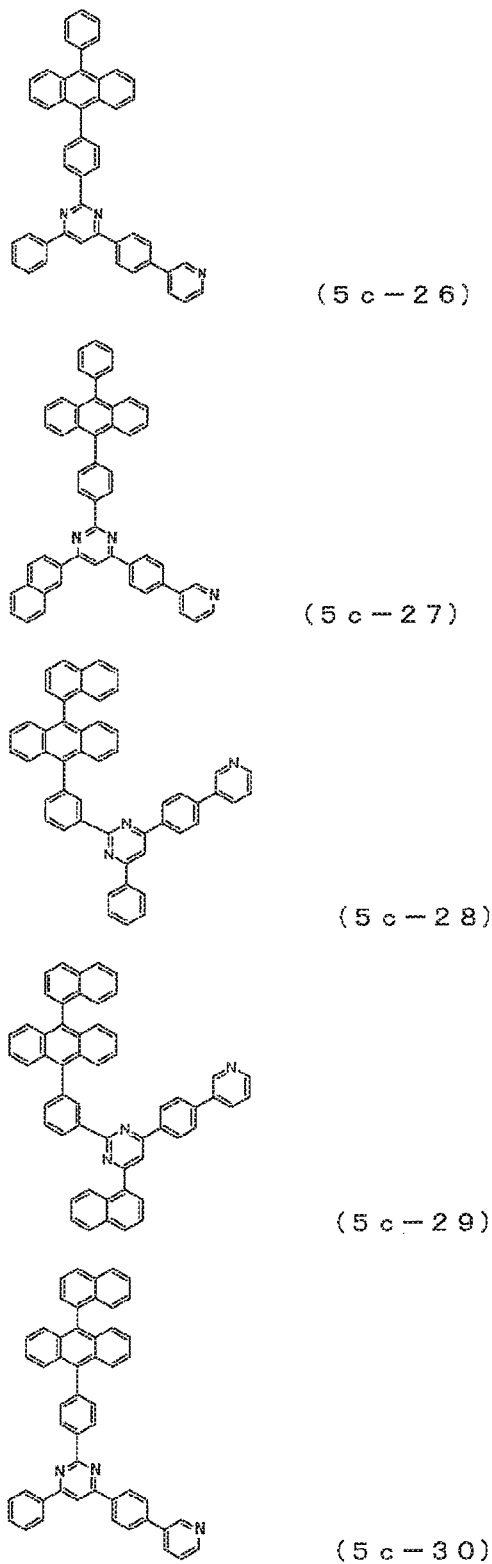
[FIG. 41] is a view showing the structural formulas of Compounds (5c-26) to (5c-30) in the anthracene derivative of the general formula (5c).
Figure 42:
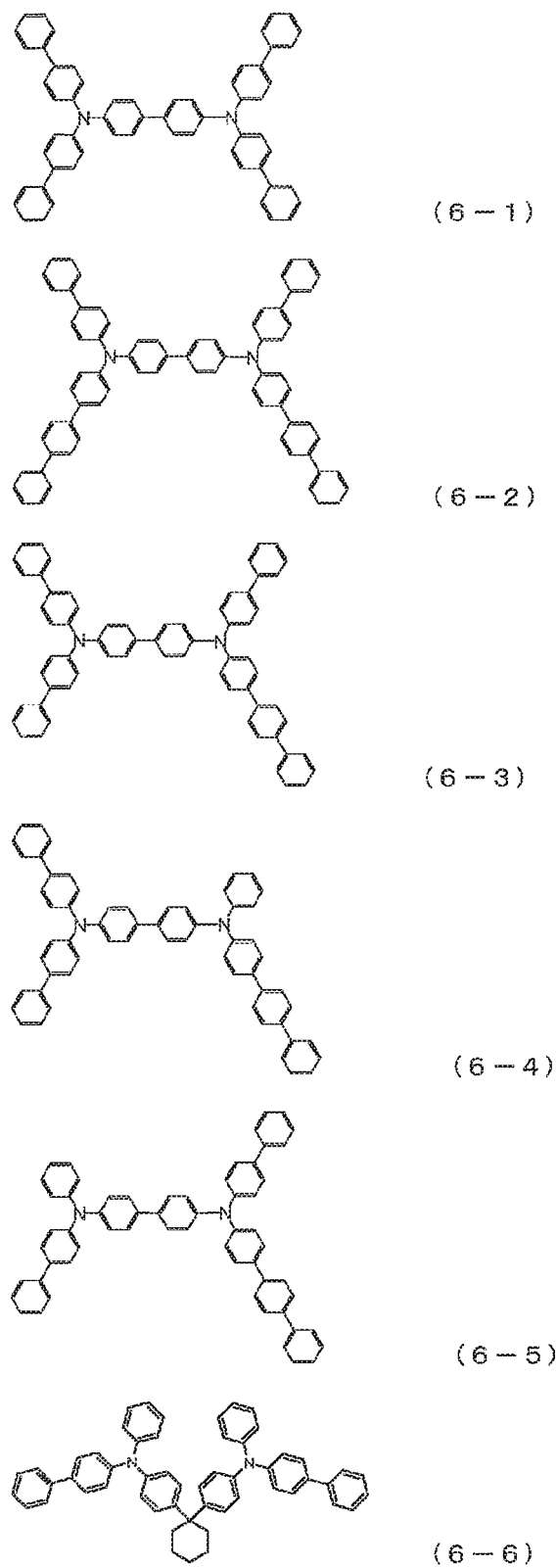
[FIG. 42] is a view showing the structural formulas of Compounds (6-1) to (6-6) in the triarylamine derivative of the general formula (6).
Figure 43:
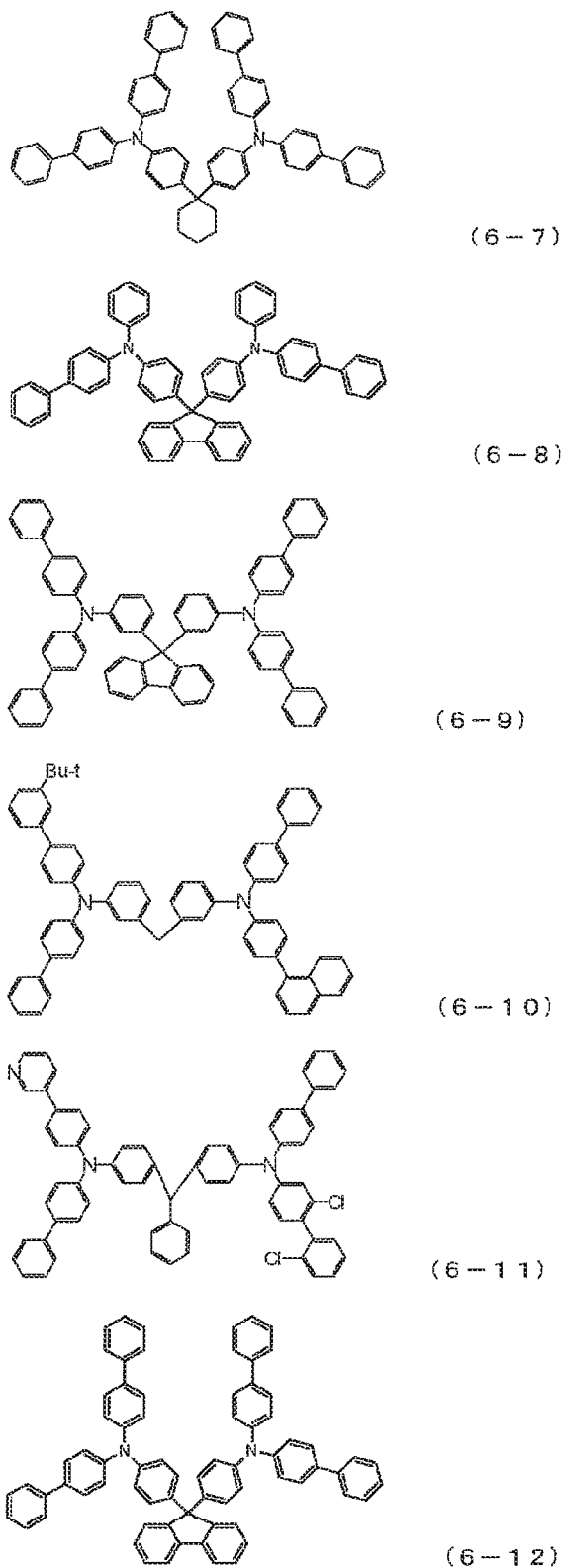
[FIG. 43] is a view showing the structural formulas of Compounds (6-7) to (6-12) in the triarylamine derivative of the general formula (6).
Figure 44:
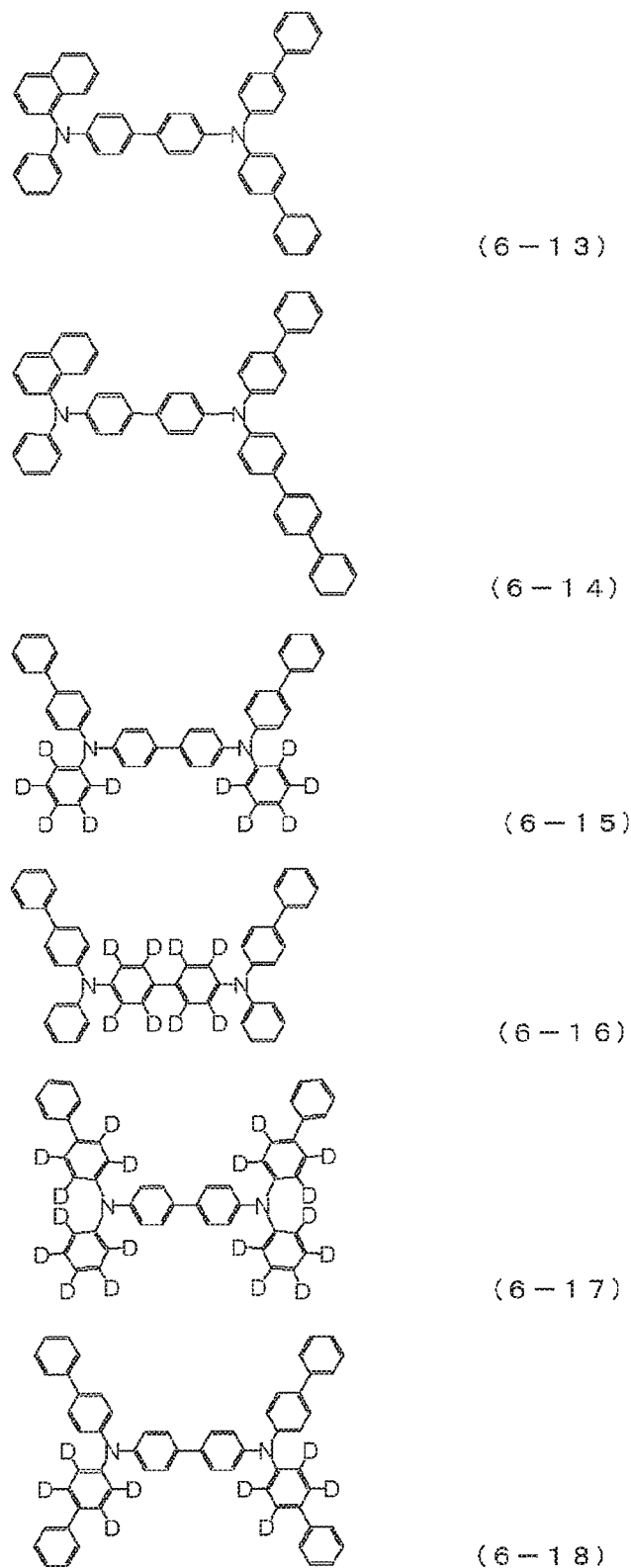
[FIG. 44] is a view showing the structural formulas of Compounds (6-13) to (6-18) in the triarylamine derivative of the general formula (6).
Figure 45:
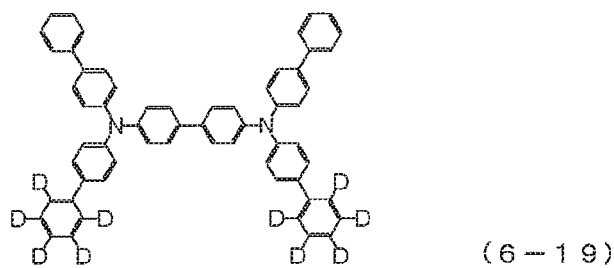
[FIG. 45] is a view showing the structural formulas of Compounds (6-19) to (6-23) in the triarylamine derivative of the general formula (6).
Figure 45:
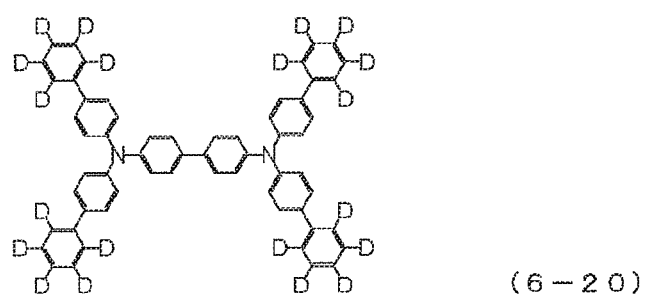
Figure 45:
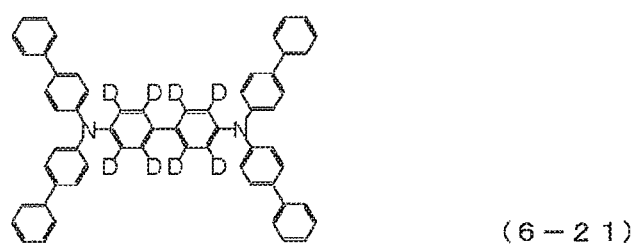
Figure 45:
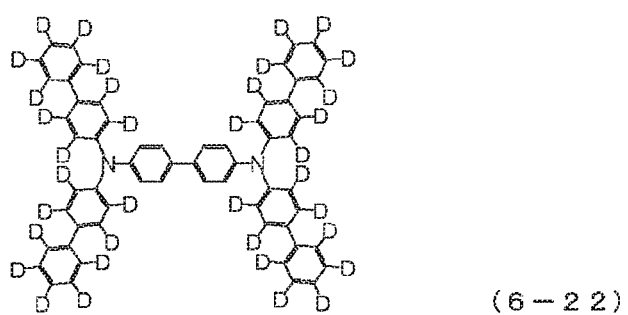
Figure 45:
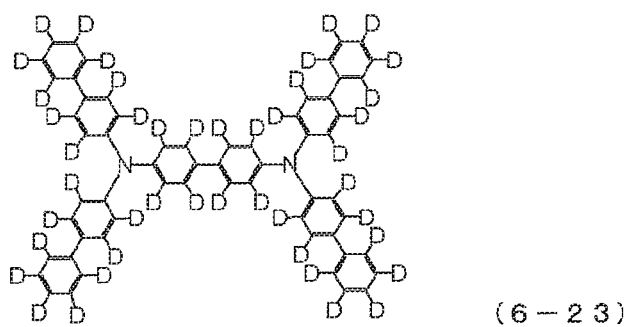

The preferred specific examples of the anthracene derivative of the general formula (5b) can include compounds (5b-1) to (5b-16) having the structural formulas shown in FIG. 33 to FIG. 35, but the compound of the general formula (5b) is not limited thereto.

The Anthracene Derivative Represented by the General Formula (5c);

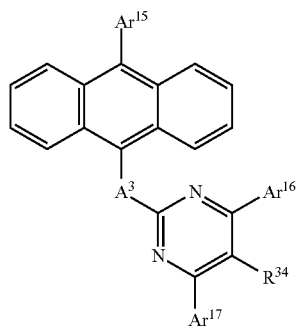

(5c)

wherein, $A^3$ has the same meaning as that defined in the aforementioned general formula (5);

$Ar^{15}$ to $Ar^{17}$ each represent an aromatic hydrocarbon group or an aromatic heterocyclic group; and $R^{34}$ represents a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, or an aryloxy group.

In the general formula (5c), the nitrogen containing aromatic heterocyclic ring to which $A^3$ is bonded corresponds to the group B in the general formula (5). Further, $Ar^{15}$ in the general formula (5c) corresponds to C in the general formula (5) (that is, q=1). $Ar^{16}$, $Ar^{17}$, and $R^8$ are substituents bonded to the nitrogen containing aromatic heterocyclic ring.

$Ar^{15}$ to $Ar^{17}$;

The aromatic hydrocarbon group or the aromatic heterocyclic group represented by $Ar^{15}$ to $Ar^{17}$ in the general formula (5c) can be exemplified by the same ones as those illustrated in relation to the aromatic hydrocarbon group or the aromatic heterocyclic group represented by $Ar^1$ to $Ar^4$ in the general formula (1). These groups may be unsubstituted or may have a substituent. The substituents can be exemplified by the same ones as those illustrated in relation to the substituents that are optionally possessed by the aromatic hydrocarbon group and the aromatic heterocyclic group represented by $Ar^1$ to $Ar^4$ in the general formula (1). Modes which the substituents can adopt are also the same.

As $Ar^{15}$ to $Ar^{17}$, an aromatic hydrocarbon group, a pyridyl group, a quinolyl group, an isoquinolyl group or a carbolinyl group is preferred, and a phenyl group, a biphenylyl group, a naphthyl group, an anthracenyl group, a phenanthrenyl group, a fluorenyl group, a pyridyl group, a quinolyl group, an isoquinolyl group, or a carbolinyl group is more preferred.

$R^{34}$;

The alkyl group having 1 to 6 carbon atoms, the cycloalkyl group having 5 to 10 carbon atoms, or the alkenyl group having 2 to 6 carbon atoms, which is represented by $R^{34}$ in the general formula (5c), can be exemplified by the same ones as those illustrated in relation to the alkyl group having 1 to 6 carbon atoms, the cycloalkyl group having 5 to 10 carbon atoms, or the alkenyl group having 2 to 6 carbon atoms which is represented by $R^1$ to $R^8$ in the general formula (2). These groups may be unsubstituted or may have a substituent. The substituents can be exemplified by the same ones as those illustrated as the substituents optionally possessed by the alkyl group having 1 to 6 carbon atoms, the cycloalkyl group having 5 to 10 carbon atoms, and the alkenyl group having 2 to 6 carbon atoms which are represented by $R^1$ to $R^8$ in the general formula (2). Modes which the substituents can adopt are also the same.

The alkyloxy group having 1 to 6 carbon atoms or the cycloalkyloxy group having 5 to 10 carbon atoms, which is represented by $R^{34}$ in the general formula (5c), can be exemplified by the same ones as those illustrated in relation to the alkyloxy group having 1 to 6 carbon atoms or the cycloalkyloxy group having 5 to 10 carbon atoms which is represented by $R^1$ to $R^8$ in the general formula (2). These groups may be unsubstituted or may have a substituent. The substituents can be exemplified by the same ones as those illustrated as the substituents optionally possessed by the alkyl group having 1 to 6 carbon atoms, the cycloalkyl group having 5 to 10 carbon atoms, and the alkenyl group having 2 to 6 carbon atoms which are represented by $R^1$ to $R^8$ in the general formula (2). Modes which the substituents can adopt are also the same.

The aromatic hydrocarbon group or the aromatic heterocyclic group, which is represented by $R^{34}$ in the general formula (5c), can be exemplified by the same ones as those illustrated in relation to the aromatic hydrocarbon group or the aromatic heterocyclic group, which are represented by $Ar^1$ to $Ar^4$ in the general formula (1). These groups may be unsubstituted or may have a substituent. The substituents can be exemplified by the same ones as those illustrated as the substituents optionally possessed by the aromatic hydrocarbon group and the aromatic heterocyclic group, which are represented by $Ar^1$ to $Ar^4$ in the general formula (1). Modes which the substituents can adopt are also the same.

The aryloxy group, which is represented by $R^{34}$ in the general formula (5c), can be exemplified by the same ones as those illustrated in relation to the aryloxy group, which is represented by $R^1$ to $R^8$ in the general formula (2). These groups may be unsubstituted or may have a substituent. The substituents can be exemplified by the same ones as those illustrated as the substituents optionally possessed by the aromatic hydrocarbon group and the aromatic heterocyclic group which are represented by $Ar^1$ to $Ar^4$ in the general formula (1). Modes which the substituents can adopt are also the same.

The preferred specific examples of the anthracene derivative of the general formula (5c) can include compounds (5c-1) to (5c-30) having the structural formulas shown in FIG. 36 to FIG. 41, but the compound of the general formula (5c) is not limited thereto.

The above-described anthracene derivative of the general formula (5) can be synthesized by a publicly known method (see Patent Documents 8 to 10).

The synthesized compound can be purified by column chromatography purification, adsorption purification with silica gel, activated carbon, or activated clay, recrystallization or crystallization with a solvent, a sublimation purification method, or the like. The compound to be used in the organic EL device of the present invention is finally purified by the sublimation purification method and supplied for use.

<Cathode>

An electrode material with a low work function, such as aluminum, or an alloy electrode material with a lower work function, such as a magnesium-silver alloy, a magnesium-indium alloy, and an aluminum-magnesium alloy, is used as the cathode in the organic EL device of the present invention.

<Other Layers>

The organic EL device of the present invention may have, as necessary, other layers. For example, in the example depicted in FIG. 1, the hole injection layer 3 is provided between the anode 2 and the hole transport layer 5, and the electron injection layer 8 is provided between the cathode 9 and the electron transport layer 7. Further, an electron blocking layer can be provided between the hole transport layer 5 and the luminous layer 6, and a hole blocking layer can be provided between the luminous layer 6 and the electron transport layer 7 (these configurations are not depicted in the figures).

The appropriately provided layers may be formed from publicly known materials and are formed by a publicly known method such as a vapor deposition method, a spin coat method, and an ink jet method according to the type of the material to be used.

Hole Injection Layer;

The hole injection layer 3 which is provided, as appropriate, between the anode 2 and the hole transport layer 5 can be formed using publicly known materials, for example, materials such as triphenylamine derivatives of a starburst type, and various triphenylamine tetramers;

porphyrin compounds represented by copper phthalocyanine;

heterocyclic compounds having acceptor property, for example, hexacyanoazatriphenylene; and coating-type polymer materials.

Further, since the above-described arylamine compound of the general formula (1) and the below-described triarylamine derivatives represent by the general formula (6) or (7) demonstrate a large hole mobility, the hole injection layer can be also formed using such arylamine compounds.

The material usually used for the hole injection layer is further P-doped with trisbromophenylamine hexachloroantimony, a radialene derivative (see WO2014/009310), or the like and can be used for the hole injection layer, or a polymer compound having the structure of a benzidine derivative such as TPD in a partial structure thereof can be used for the hole injection layer.

Electron Injection Layer;

The following materials can be used to form the electron injection layer:

an alkali metal salt such as lithium fluoride and cesium fluoride;

an alkaline earth metal salt such as magnesium fluoride; and a metal oxide such as aluminum oxide.

However, when the preferred electron transport layer and cathode are selected, this layer can be omitted.

Electron Blocking Layer;

The electron blocking layer, which is not depicted in FIG. 1, can be provided between the hole transport layer and the luminous layer. The electron blocking layer is formed to block the transmission of electrons from the luminous layer and increase the luminous efficiency. In addition to the arylamine compound of the general formula (1), for example, the following compounds demonstrating the electron blocking action can be used as the materials for forming the electron blocking layer.

Carbazole Derivatives, for Example, 4,4',4"-tri(N-carbazolyl)triphenylamine (TCTA), 9,9-bis[4-(carbazol-9-yl)phenyl]fluorene, 1,3-bis(carbazol-9-yl)benzene (mCP), 2,2-bis(4-carbazol-9-ylphenyl)adamantane (Ad-Cz); and compounds having a triphenylsilyl group and a triarylamine structure, for example, 9-[4-(carbazol-9-yl)phenyl]-9-[4-(triphenylsilyl)phenyl]-9H-fluorene.

Hole Blocking Layer;

The hole blocking layer, which is not depicted in FIG. 1, is provided, as appropriate, between the electron transport layer and the luminous layer. The hole blocking layer is formed to block the transmission of holes from the luminous layer and increase the luminous efficiency. The following materials, for example, can be used to form the hole blocking layer:

phenanthroline derivatives, for example, bathocuproine (BCP);

metal complexes of quinolinol derivatives, for example, aluminum(III) bis(2-methyl-8-quinolinato)-4-phenylphenolate (BAlq);

various rare earth complexes;

triazole derivatives;

triazine derivatives; and oxadiazole derivatives.

These materials may also serve as materials for the electron transport layer.

<Hole Transport Layer of Two-Layer Structure>

In the organic EL device of the present invention, the above-described arylamine compound of the general formula (1) is used as a hole transport agent, but as mentioned hereinabove, the hole transport layer including such an arylamine compound can have a two-layer structure.

Thus, as depicted in FIG. 1, it is preferred that the hole transport layer 5 be divided into the first hole transport layer 5a positioned on the anode 2 side and the second hole transport layer 5b positioned on the luminous layer 6 side, thereby forming a two-layer structure, and the arylamine compound of the general formula (1) be included in the second hole transport layer 5b. In this case, an arylamine different from that used in the second hole transport layer 5b is used in the first hole transport layer 5a.

When the hole transport layer is divided into two layers, as described hereinabove, the second hole transport layer 5b on the luminous layer 6 side demonstrates hole transport property and also very strong electron blocking property. This is because the above-described arylamine compound of the general formula (1) demonstrates strong electron blocking property in addition to excellent hole transport property. Therefore, by arranging the second hole transport layer 5b adjacently to the luminous layer 6, as shown in FIG. 1, it is possible to maintain a higher carrier balance in the luminous layer 6 which is very effective for improving the characteristics of the organic EL device.

The first hole transport layer 5a is formed using an arylamine derivative different from the arylamine derivative used to form the second hole transport layer 5b. This is because an arylamine skeleton demonstrates excellent hole transport property.

The arylamine derivative which is used to form the first hole transport layer 5a may be the above-described arylamine compound of the general formula (1), provided that it is different from that used for forming the second hole transport layer 5b. However, since electron blocking property is not needed that much for the first hole transport layer 5a, it is desirable that the first hole transport layer 5a be formed using a publicly known arylamine derivative which is used as a hole transport agent.

As a well-known arylamine derivative, it is preferred to use an arylamine derivative having a molecular structure in which two arylamine skeletons are bonded to each other via a single bond or a divalent hydrocarbon group, and the number of arylamine skeletons in the molecule be 2 to 6.

In the present invention, from the standpoint of providing excellent thin film stability and heat resistance in addition to the hole transport property and also facilitating the synthesis, it is more preferred that the first hole transport layer 5a be formed using the triarylamine derivative represented by the following general formula (6) or (7). Such triarylamine derivatives can be used individually or as a mixture of two or more thereof.

Triarylamine Derivative Represented by the General Formula (6);

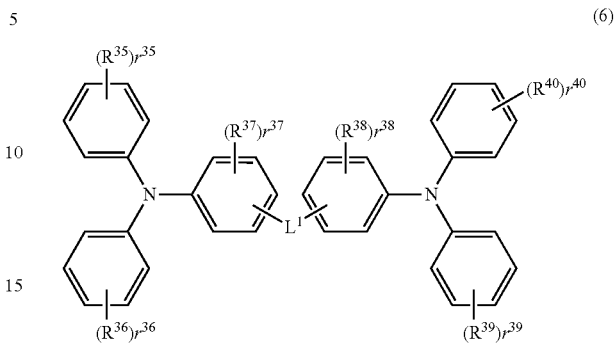

(6)

The triarylamine derivative represented by the general formula (6) has two triarylamine skeletons.

($r^{35}$ to $r^{40}$ in the General Formula (6))

In the general formula (6), $r^{35}$, $r^{36}$, $r^{39}$, and $r^{40}$ each represent an integer of 0 to 5, and $r^{37}$ and $r^{38}$ each represent an integer of 0 to 4. When $r^{35}$, $r^{36}$, $r^{39}$, and $r^{40}$ each are an integer of 2 to 5 or when $r^{37}$ and $r^{38}$ each are an integer of 2 to 4, a plurality of $R^{35}$ to $R^{40}$ which are bonded to the same benzene ring may be the same or different and may be present individually without forming a ring, or may be bonded to each other via a single bond, a substituted or unsubstituted methylene group, an oxygen atom, or a sulfur atom to form a ring.

($R^{35}$ to $R^{40}$ in the General Formula (6))

In the general formula (6), $R^{35}$ to $R^{40}$ each represent a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, or an aryloxy group. When a plurality of these groups are present in the same benzene ring, these groups may be bonded to each other via a single bond, a methylene group which have a substituent, an oxygen atom, or a sulfur atom to form a ring.

Specific examples of the alkyl group having 1 to 6 carbon atoms, the cycloalkyl group having 5 to 10 carbon atoms, or the alkenyl group having 2 to 6 carbon atoms, which is represented by $R^{35}$ to $R^{40}$ in the general formula (6), include a methyl group, an ethyl group, an n-propyl group, an isopropyl group, an n-butyl group, an isobutyl group, a tert-butyl group, an n-pentyl group, an isopentyl group, a neopentyl group, an n-hexyl group, a cyclopentyl group, a cyclohexyl group, a 1-adamantyl group, a 2-adamantyl group, a vinyl group, an allyl group, an isopropenyl group, and a 2-butenyl group, etc.

The alkyl groups having 1 to 6 carbon atoms and the alkenyl groups having 2 to 6 carbon atoms may be straight-chain or branched.

These groups may be unsubstituted or may have a substituent. The following groups, in addition to a deuterium atom, a cyano group, and a nitro group, can exemplify the substituents:

a halogen atom, for example, a fluorine atom, a chlorine atom, a bromine atom, and an iodine atom;

an alkyloxy group having 1 to 6 carbon atoms, for example, a methyloxy group, an ethyloxy group, and a propyloxy group;

an alkenyl group, for example, a vinyl group and an allyl group;

an aryloxy group, for example, a phenyloxy group and a tolyloxy group;

an arylalkyloxy group, for example, a benzyloxy group and a phenethyloxy group;

an aromatic hydrocarbon group, for example, a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, and a triphenylenyl group; and an aromatic heterocyclic group, for example, a pyridyl group, a pyrimidinyl group, a triazinyl group, a thienyl group, a furyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, and a carbolinyl group.

These substituents may further have the substituents exemplified hereinabove. Further, these substituents may be present individually without forming a ring, or may be bonded to each other via a single bond, a substituted or unsubstituted methylene group, an oxygen atom, or a sulfur atom to form a ring.

Among the abovementioned substituents, the alkyloxy groups having 1 to 6 carbon atoms may be straight-chain or branched.

Specific examples of the alkyloxy group having 1 to 6 carbon atoms or the cycloalkyloxy group having 5 to 10 carbon atoms, which is represented by $R^{35}$ to $R^{40}$ in the general formula (6), include a methyloxy group, an ethyloxy group, an n-propyloxy group, an isopropyloxy group, an n-butyloxy group, a tert-butyloxy group, an n-pentyloxy group, an n-hexyloxy group, a cyclopentyloxy group, a cyclohexyloxy group, a cycloheptyloxy group, a cyclooctyloxy group, a 1-adamantyloxy group, and a 2-adamantyloxy group, etc. The alkyloxy group having 1 to 6 carbon atoms may be straight-chain or branched. These groups may be unsubstituted or may have a substituent. The substituents can be exemplified by the same ones as those illustrated as the substituents optionally possessed by the alkyl group having 1 to 6 carbon atoms, the cycloalkyl group having 5 to 10 carbon atoms, and the alkenyl group having 2 to 6 carbon atoms which are represented by $R^{35}$ to $R^{40}$ in the general formula (6). Modes which the substituents can adopt are also the same.

The aromatic hydrocarbon group or the aromatic heterocyclic group represented by $R^{35}$ to $R^{40}$ in the general formula (6) can be exemplified by the same ones as those illustrated in relation to the aromatic hydrocarbon group or the aromatic heterocyclic group represented by $Ar^1$ to $Ar^4$ in the general formula (1). These groups may be unsubstituted or may have a substituent. The substituents can be exemplified by the same ones as those illustrated as the substituents optionally possessed by the aromatic hydrocarbon group and the aromatic heterocyclic group represented by $Ar^1$ to $Ar^4$ in the general formula (1). Modes which the substituents can adopt are also the same.

The aryloxy group represented by $R^{35}$ to $R^{40}$ in the general formula (6) can be specifically exemplified by a phenyloxy group, a biphenylyloxy group, a terphenylyloxy group, a naphthyloxy group, an anthracenyloxy group, a phenanthrenyloxy group, a fluorenyloxy group, an indenyloxy group, a pyrenyloxy group, and a perylenyloxy group, etc. These groups may be unsubstituted or may have a substituent. The substituents can be exemplified by the same ones as those illustrated as the substituents optionally possessed by the aromatic hydrocarbon group and the aromatic heterocyclic group represented by $Ar^1$ to $Ar^4$ in the general formula (1). Modes which the substituents can adopt are also the same.

$R^{35}$ to $R^{40}$ may be present individually without forming a ring, or may be bonded to each other via a single bond, a substituted or unsubstituted methylene group, an oxygen atom, or a sulfur atom to form a ring.

($L^1$ in the General Formula (6))

In the general formula (6), $L^1$ is a bridge group that connects the two arylamine skeletons and represents a divalent group shown by any of the structural formulas (C) to (G) indicated below or a single bond.

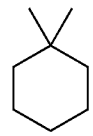

(C)

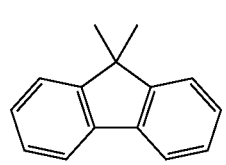

(D)

—$CH_2$—

(E)

—CH—

(F)

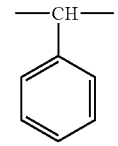

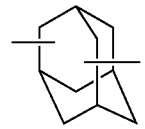

(G)

The preferred specific examples of the triarylamine derivative of the general formula (6) can include compounds (6-1) to (6-23) having the structural formulas shown in FIG. 42 to FIG. 45. The compound of the general formula (6) is not limited to these compounds.

Figure 46:
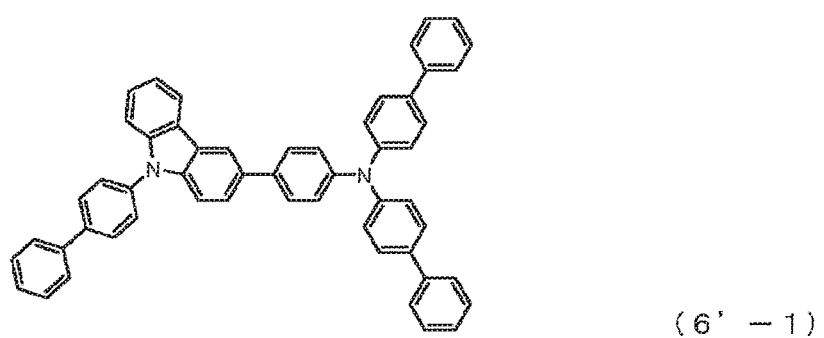
[FIG. 46] is a view showing the structural formulas of Compounds (6'-1) to (6'-2).
Figure 46:
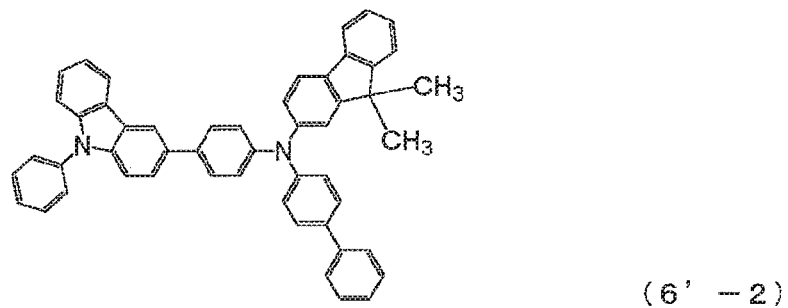
Figure 47:
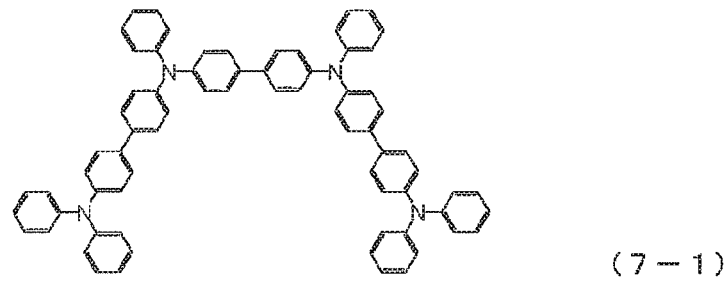
[FIG. 47] is a view showing the structural formulas of Compounds (7-1) to (7-4) in the triarylamine derivative of the general formula (7).
Figure 47:
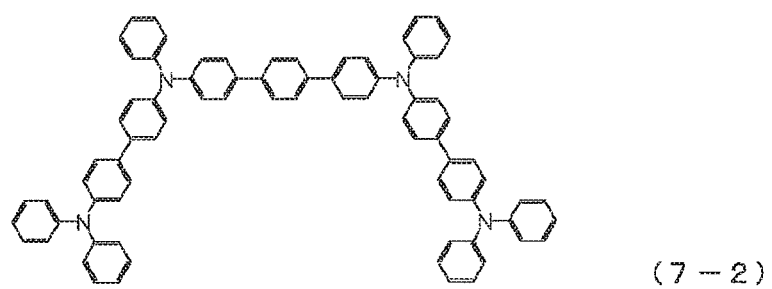
Figure 47:
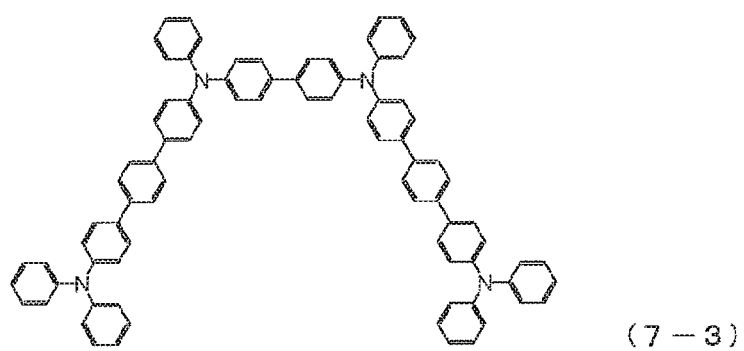
Figure 47:
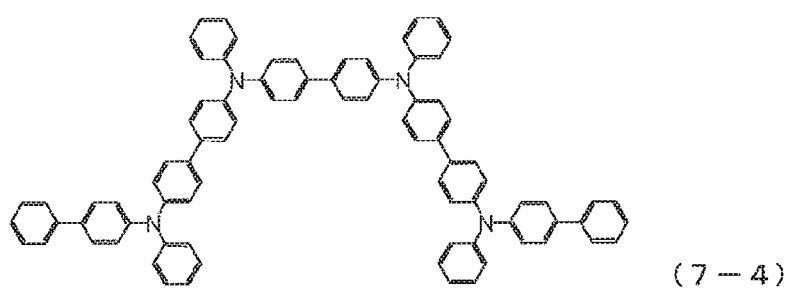
Figure 48:
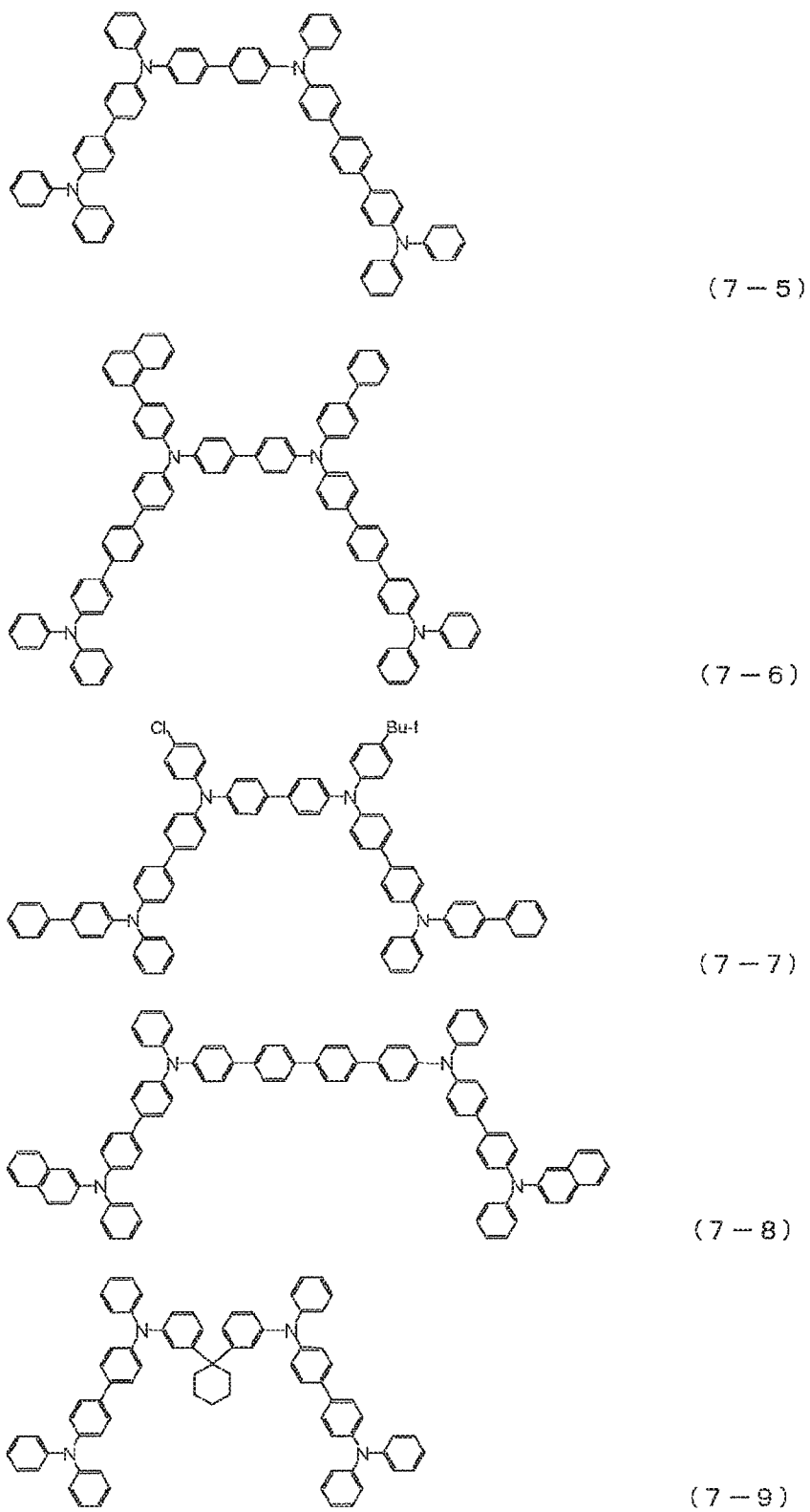
[FIG. 48] is a view showing the structural formulas of Compounds (7-5) to (7-9) in the triarylamine derivative of the general formula (7).
Figure 49:
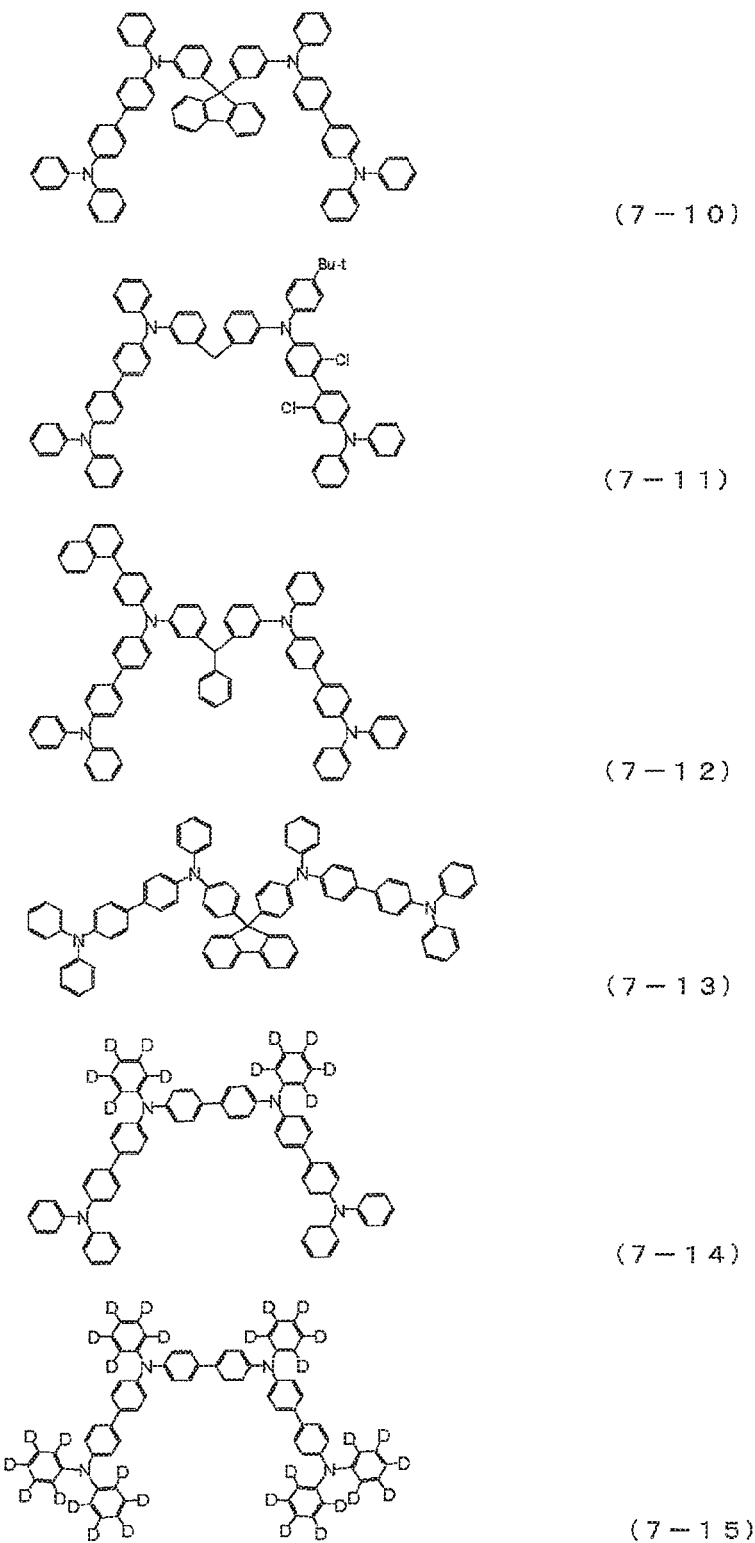
[FIG. 49] is a view showing the structural formulas of Compounds (7-10) to (7-15) in the triarylamine derivative of the general formula (7).
Figure 50:
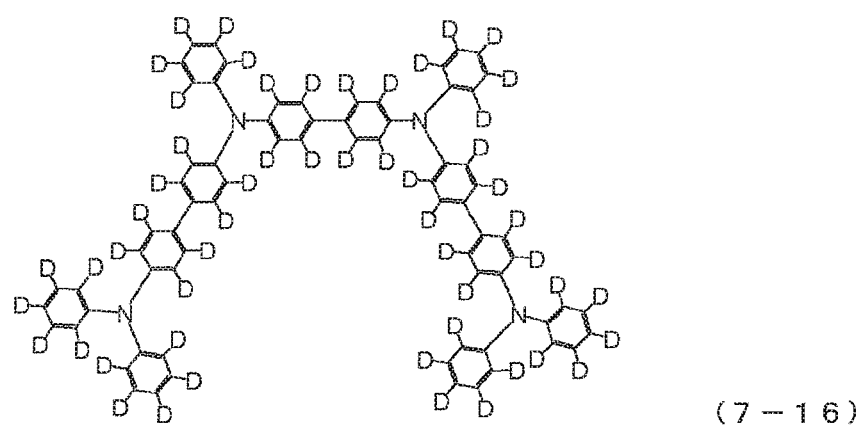
[FIG. 50] is a view showing the structural formulas of Compounds (7-16) to (7-17) in the triarylamine derivative of the general formula (7).
Figure 50:
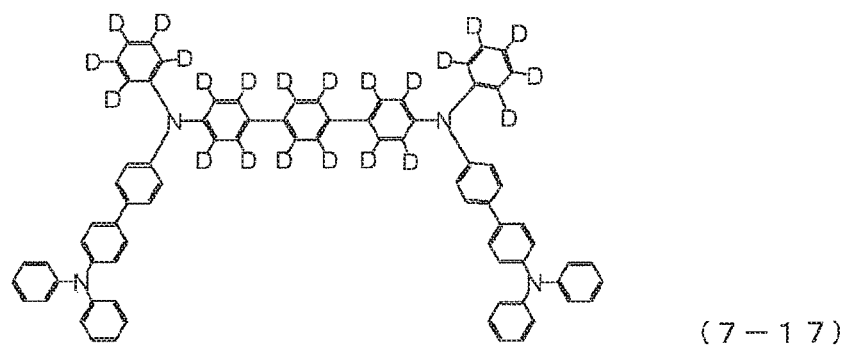

The preferred specific examples, other than the triarylamine derivatives of the general formula (6), of the arylamine derivative which is preferably used in the first hole transport layer and has a molecular structure in which two arylamine skeletons are present and bonded to each other via a single bond or a divalent group having no hetero atom, can include compounds (6'-1) to (6'-2) having the structural formulas shown in FIG. 46.

The triarylamine derivative of the general formula (6) can be synthesized by a publicly known method (see Patent Documents 11 and 12).

Likewise, the compounds (6'-1) to (6'-2) can be also synthesized by a publicly known method (see Patent Documents 11 and 12).

The synthesized compound can be purified by column chromatography purification, adsorption purification with silica gel, activated carbon, or activated clay, recrystallization or crystallization with a solvent, a sublimation purification method, or the like. The compound to be used in the organic EL device of the present invention is finally purified by the sublimation purification method and supplied for use.
Triarylamine Derivative Represented by the General Formula (7);

which are represented by $R^{35}$ to $R^{40}$ in the general formula (6). The modes that can be adopted are also the same. These groups may be unsubstituted or may have a substituent. The substituents can be exemplified by the same ones as those illustrated as the substituents optionally possessed by the

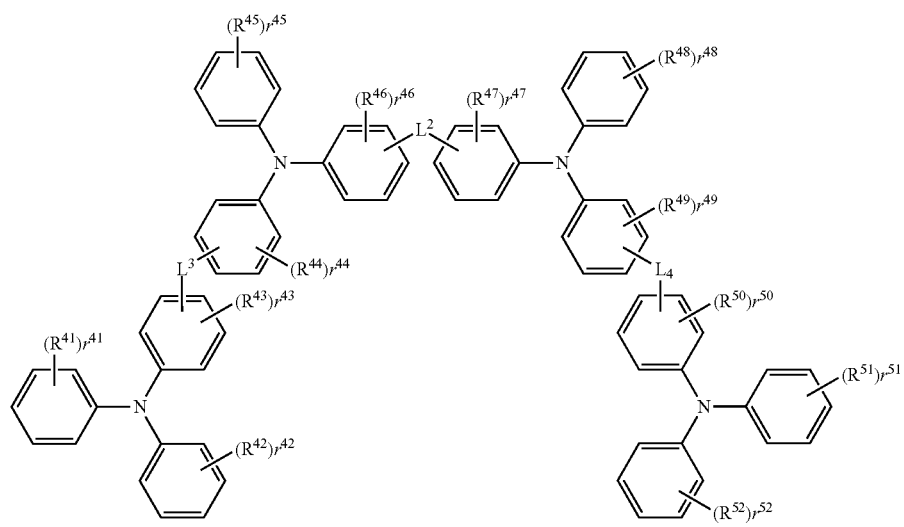

(7)

The triarylamine derivative represented by the general formula (7) has four triarylamine skeletons.

($r^{41}$ to $r^{52}$ in the general formula (7))

In the general formula (7), $r^{41}$ to $r^{52}$ are each an integer indicating the number of substituents $R^{41}$ to $R^{52}$ bonded to the aromatic ring. $r^{41}$, $r^{42}$, $r^{45}$, $r^{48}$, $r^{51}$, and $r^{52}$ each represent an integer of 0 to 5, and $r^{43}$, $r^{44}$, $r^{46}$, $r^{47}$, $r^{49}$, and $r^{50}$ each represent an integer of 0 to 4.

When $r^{41}$, $r^{42}$, $r^{45}$, $r^{48}$, $r^{51}$, and $r^{52}$ each are an integer of 2 to 5 or when $r^{43}$, $r^{44}$, $r^{46}$, $r^{47}$, $r^{49}$, and $r^{50}$ each are an integer of 2 to 4, a plurality of $R^{41}$ to $R^{52}$ which are bonded to the same benzene ring may be the same or different and may be present individually without forming a ring, or may be bonded to each other via a single bond, a substituted or unsubstituted methylene group, an oxygen atom, or a sulfur atom to form a ring.

($R^{41}$ to $R^{52}$ in the General Formula (7))

In the general formula (7), $R^{41}$ to $R^{52}$, which are bonded to the aromatic ring, each represent a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, or an aryloxy group.

When a plurality of these groups are present in the same benzene ring, these groups may be bonded to each other via a single bond, a methylene group which may have a substituent, an oxygen atom, or a sulfur atom to form a ring.

The alkyl group having 1 to 6 carbon atoms, the cycloalkyl group having 5 to 10 carbon atoms, or the alkenyl having 2 to 6 carbon atoms, which is represented by $R^{41}$ to $R^{52}$ in the general formula (7), can be exemplified by the same ones as those illustrated in relation to the alkyl group having 1 to 6 carbon atoms, the cycloalkyl group having 5 to 10 carbon atoms, or the alkenyl group having 2 to 6 carbon atoms, alkyl group having 1 to 6 carbon atoms, the cycloalkyl group having 5 to 10 carbon atoms, or the alkenyl group having 2 to 6 carbon atoms which is represented by $R^{35}$ to $R^{40}$ in the general formula (6). Modes which the substituents can adopt are also the same.

The alkyloxy group having 1 to 6 carbon atoms or the cycloalkyloxy group having 5 to 10 carbon atoms, which is represented by $R^{41}$ to $R^{52}$, can be exemplified by the same ones as those illustrated in relation to the alkyloxy group having 1 to 6 carbon atoms or the cycloalkyloxy group having 5 to 10 carbon atoms, which is represented by $R^{35}$ to $R^{40}$ in the general formula (6). The modes that can be adopted are also the same. These groups may be unsubstituted or may have a substituent. The substituents can be exemplified by the same ones as those illustrated as the substituents optionally possessed by the alkyl group having 1 to 6 carbon atoms, the cycloalkyl group having 5 to 10 carbon atoms, or the alkenyl group having 2 to 6 carbon atoms, which is represented by $R^{35}$ to $R^{40}$ in the general formula (6). Modes which the substituents can adopt are also the same.

The aromatic hydrocarbon group or the aromatic heterocyclic group, which is represented by $R^{41}$ to $R^{52}$, can be exemplified by the same ones as those illustrated in relation to the aromatic hydrocarbon group or the aromatic heterocyclic group, which is represented by $Ar^1$ to $Ar^4$ in the general formula (1). These groups may be unsubstituted or may have a substituent. The substituents can be exemplified by the same ones as those illustrated as the substituents optionally possessed by the aromatic hydrocarbon group and the aromatic heterocyclic group, which are represented by $Ar^1$ to $Ar^4$ in the general formula (1). Modes which the substituents can adopt are also the same.

The aryloxy group, which is represented by $R^{41}$ to $R^{52}$, can be exemplified by the same ones as those illustrated in relation to the aryloxy group which is represented by $R^{35}$ to $R^{40}$ in the general formula (6). These groups may be unsubstituted or may have a substituent. The substituents can be exemplified by the same ones as those illustrated as the substituents optionally possessed by aromatic hydrocarbon group and the aromatic heterocyclic group which are represented by $Ar^1$ to $Ar^4$ in the general formula (1). Modes which the substituents can adopt are also the same.

$R^{41}$ to $R^{52}$ may be present individually without forming a ring, or may be bonded to each other via a single bond, a substituted or unsubstituted methylene group, an oxygen atom, or a sulfur atom to form a ring.

($L^2$ to $L^4$ in the General Formula (7))

In the general formula (7), $L^2$ to $L^4$ may be the same or different and represent a divalent group illustrated by either of the structural formulas (H) and (I) indicated below, a divalent group illustrated by any of the structural formulas (C) to (G) indicated below in the general formula (6), or a single bond.

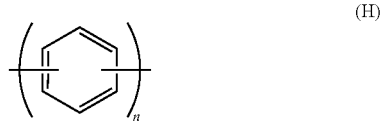

(H)

wherein,
n is an integer of 1 to 3.

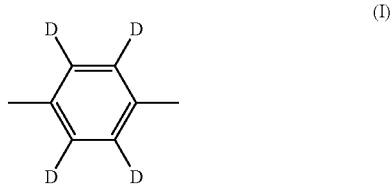

(I)

The preferred specific examples of the triarylamine derivative of the general formula (7) can include compounds (7-1) to (7-17) having the structural formulas shown in FIG. 47 to FIG. 50. The compound of the general formula (7) is not limited thereto.

The triarylamine derivative of the general formula (7) can be synthesized according to a publicly known method (see Patent Documents 11 and 12).

The synthesized compound can be purified by column chromatography purification, adsorption purification with silica gel, activated carbon, or activated clay, recrystallization or crystallization with a solvent, a sublimation purification method, or the like. The compound to be used in the organic EL device of the present invention is finally purified by the sublimation purification method and supplied for use.

EXAMPLES

The present invention will be described more concretely by way of Examples, but the present invention is in no way limited to the following Examples.

Example 1

Compound 1-5

Synthesis of 4-{(biphenyl-4-yl)-phenylamino}-4"-{(9,9-dimethyl-9H-fluoren-2-yl)-phenylamino}-1,1': 3',1"-terphenyl

| | |
|---|---|
| A nitrogen-purged reaction vessel was charged with | |
| N-(biphenyl-4-yl)-N-(4-bromophenyl)aniline | 8.0 g, |
| N-(9,9-dimethyl-9H-fluoren-2-yl)-N-{3'-(4,4,5,5-tetramethyl-[1,3,2]dioxaboran-2-yl)biphenyl-4-yl}aniline | 11.4 g, |
| potassium carbonate | 7.5 g, |
| water | 64 ml, |
| toluene | 64 ml, |
| ethanol | 16 ml, and |
| tetrakis(triphenylphosphine)palladium | 0.8 g. |

The mixture was heated and stirred for 16 h at 70° C. After cooling to room temperature and adding ethyl acetate and water, an organic layer was collected by a fractionation operation. The organic layer was concentrated and then recrystallized by using a mixed solvent of THF/acetone. As a result, 9.54 g (yield 69%) of a white powder of 4-{(biphenyl-4-yl)-phenylamino}-4"-{(9,9-dimethyl-9H-fluoren-2-yl)-phenylamino}-1,1':3',1"-terphenyl (Compound 1-5) was obtained.

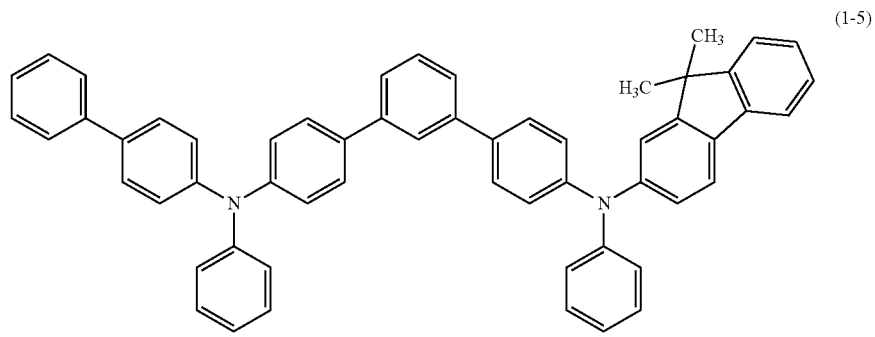

(1-5)

(1a-a)

The structure of the resulting white powder was identified using NMR. In $^1$H-NMR (THF-$d_8$), the following signals of 44 hydrogens were detected.
δ(ppm)=7.86 (1H),
7.68-6.97 (37H),
1.41 (6H)

Example 2

Compound 1-6

Synthesis of 4-{(9,9-dimethyl-9H-fluoren-2-yl)-phenylamino}-4"-{(naphthalen-1-yl)-phenylamino}-1,1':3',1"-terphenyl The reaction was conducted under the same conditions as in Example 1, except that
N-(3'-bromobiphenyl-4-yl)-N-(naphthalen-1-yl)aniline
was used instead of
N-(biphenyl-4-yl)-N-(4-bromophenyl)aniline and
4-{N-(9,9-dimethyl-9H-fluoren-2-yl)-phenylamino}-phenylboronic acid
was used instead of
N-(9,9-dimethyl-9H-fluoren-2-yl)-N-{3'-(4,4,5,5-tetramethyl-[1,3,2]dioxaboran-2-yl)biphenyl-4-yl}aniline. As a result, 7.88 g (yield 62%) of a pale yellowish white powder of 4-{(9,9-dimethyl-9H-fluoren-2-yl)-phenylamino}-4"-{(naphthalen-1-yl)-phenylamino}-1,1':3',1"-terphenyl (Compound 1-6) was obtained.

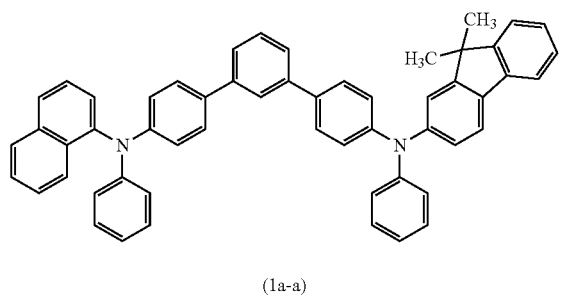

(1a-a)

The structure of the resulting pale yellowish white powder was identified using NMR. In $^1$H-NMR (CDCl$_3$), the following signals of 42 hydrogens were detected.
δ(ppm)=7.98 (1H),
7.98 (1H), 7.92 (1H), 7.84-7.75 (2H) 7.70-6.94 (32H),
1.49 (6H)

Example 3

Compound 1-21

Synthesis of 3,3"-bis{(biphenyl-4-yl)-phenylamino}-1,1':4',1"-terphenyl

| | |
|---|---|
| A nitrogen-purged reaction vessel was charged with | 6.20 g, |
| 1,4-dibromobenzene | |
| N-(biphenyl-4-yl)-N-{3-(4,4,5,5-tetramethyl-[1,3,2]dioxaboran-2-yl)phenyl}-phenylamine | 25.1 g, |
| potassium carbonate | 10.8 g, |
| water | 39 ml, |
| toluene | 380 ml, and |
| ethanol | 95 ml. |

Nitrogen gas was passed through the mixture for 30 min under ultrasonic irradiation. Then,

| | |
|---|---|
| tetrakis(triphenylphosphine)palladium | 0.95 g | was added, followed by heating and stirring for 18 h under refluxing. After cooling to room temperature and the addition of

| | |
|---|---|
| water | 200 ml and |
| heptane | 190 ml, | a precipitate was collected by filtration. The precipitate was dissolved under heating in 1200 ml of 1,2-dichlorobenzene, and adsorption purification was performed using 39 g of silica gel. Then, after the adsorption purification was performed using 19 g of activated clay, 725 ml of methanol was added and the precipitated cruide product was collected by filtration. The cruide was repeatedly crystallized using a mixed solvent of 1,2-dichloromethane/methanol and then reflux-washed using 300 ml of methanol. As a result, 15.22 g (yield 81%) of a white powder of 3,3"-bis{(biphenyl-4-yl)-phenylamino}-1,1':4',1"-terphenyl (Compound 1-21) was obtained.

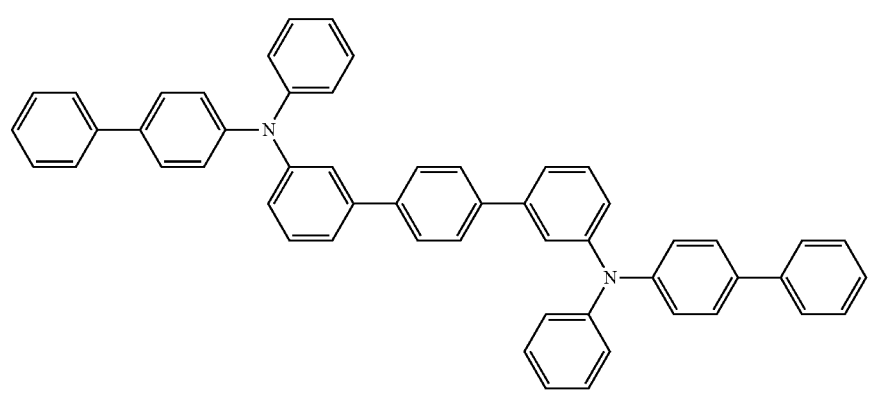

(1-21)

The structure of the resulting white powder was identified using NMR. In $^1$H-NMR (CDCl$_3$), the following signals of 40 hydrogens were detected.
δ(ppm)=7.61 (2H),
7.56-6.83 (38H)

Example 4

Compound 1-22

Synthesis of 2,2"-bis{(biphenyl-4-yl)-phenylamino}-1,1':4',1"-terphenyl

The reaction was conducted under the same conditions as in Example 3, except that N-(biphenyl-4-yl)-N-{2-(4,4,5,5-tetramethyl-[1,3,2]dioxaboran-2-yl)phenyl}-phenylamine was used instead of N-(biphenyl-4-yl)-N-{3-(4,4,5,5-tetramethyl-[1,3,2]dioxaboran-2-yl)phenyl}-phenylamine.
As a result, 11.11 g (yield 58%) of a white powder of 2,2"-bis{(biphenyl-4-yl)-phenylamino}-1,1':4',1"-terphenyl (Compound 1-22) was obtained.

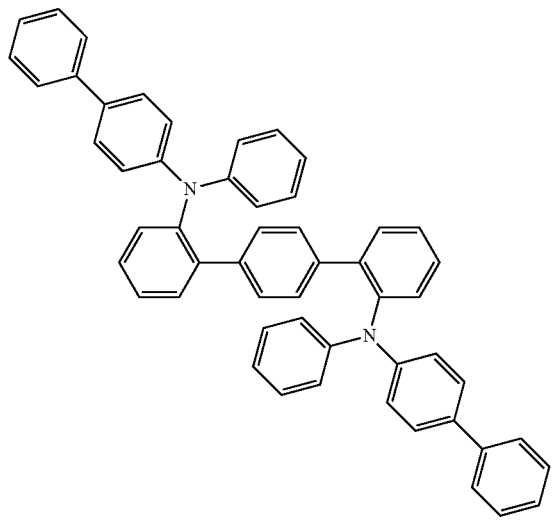

(1-22)

(1c-b)

The structure of the resulting white powder was identified using NMR. In $^1$H-NMR (THF-d$_8$), the following signals of 40 hydrogens were detected.
δ(ppm)=7.52 (4H),
7.40-7.20 (18H),
7.03 (8H),
6.90-6.75 (10H)

Example 5

Compound 1-32

Synthesis of 4-{(biphenyl-4-yl)-phenylamino}-2"-{(9,9-dimethyl-9H-fluoren-2-yl)-phenylamino}-1,1':4',1"-terphenyl A nitrogen-purged reaction vessel was charged with
| | |
|---|---|
| N-(biphenyl-4-yl)-N-(2"-bromo-1,1':4',1"-terphenyl-4-yl)aniline | 10.0 g, |
| 2-(phenylamino)-9,9-dimethyl-9H-fluorene | 6.2 g, |
| palladium acetate | 0.081 g, |
| t-butoxysodium | 3.5 g, |
| 50% (w/v) toluene solution of tri-t-butylphopshine | 0.146 g and |
| toluene | 100 ml. |

The mixture was heated and stirred overnight at 100° C. The insolubles were removed by filtration, and purification was performed by column chromatography (carrier: silica gel, eluent: heptane/dichloromethane) was performed after concentration. As a result, 4.77 g (yield 35%) of a white powder of 4-{(biphenyl-4-yl)-phenylamino}-2"-{(9,9-dimethyl-9H-fluoren-2-yl)-phenylamino}-1,1':4',1"-terphenyl (Compound 1-32) was obtained.

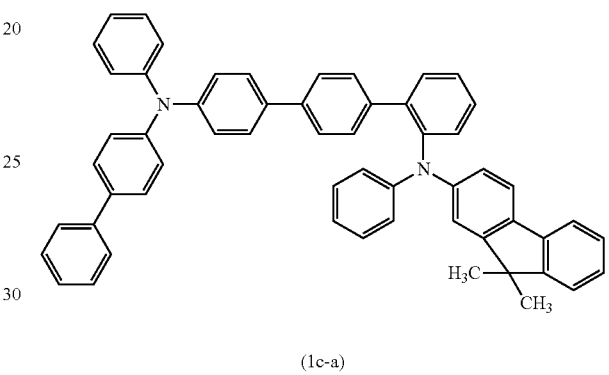

(1-32)

(1c-a)

The structure of the resulting white powder was identified using NMR. In $^1$H-NMR (THF-d$_8$), the following signals of 44 hydrogens were detected.
δ(ppm)=7.61-7.48 (4H),
7.42-6.92 (32H),
6.81 (1H),
6.76 (1H),
1.28 (6H)

Example 6

Compound 1-34

Synthesis of 4,4"-bis{(9,9-dimethyl-9H-fluoren-2-yl)-phenylamino}-1,1':3',1"-terphenyl A nitrogen-purged reaction vessel was charged with 4,4"-dibromo-1,1':3',1"-terphenyl 8.81 g, 2-(phenylamino)-9,9-dimethyl-9H-fluorene 13.6 g, t-butoxysodium 5.12 g, tris(dibenzylideneacetone)dipalladium 0.33 g, and 50% (w/v) toluene solution of tri-t-butylphopshine 0.63 ml.
The mixture was heated and stirred for 2 h under refluxing. After gradual cooling, methanol was added and a precipitate was collected by filtration. The precipitate was dissolved under heating in chlorobenzene, and adsorption purification was performed using silica gel. Then, after the adsorption purification with activated clay, crystallization was performed using a mixed solvent of chlorobenzene/methanol, and then reflux-washing was performed using methanol. As a result, 16.25 g (yield 90%) of a white powder of 4,4"-bis{(9,9-dimethyl-9H-fluoren-2-yl)-phenylamino}-1,1':3',1"-terphenyl (Compound 1-34) was obtained.

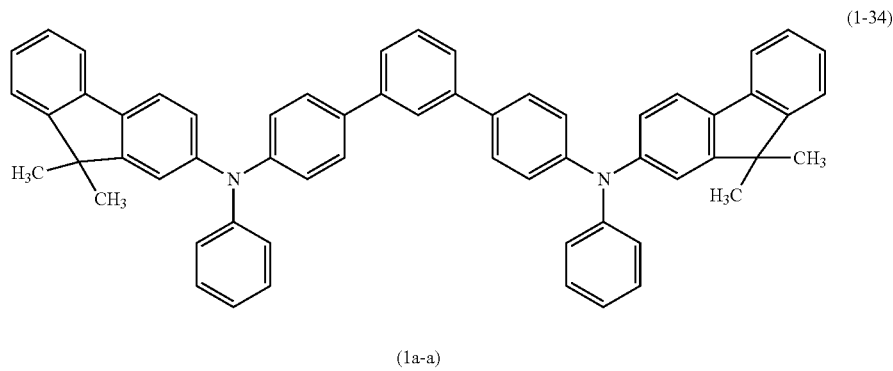 [SMILES: CC1(C)c2ccccc2-c2ccc(N(c3ccccc3)c3ccc(-c4cccc(-c5ccc(N(c6ccccc6)c6ccc7c(c6)C(C)(C)c6ccccc6-7)cc5)c4)cc3)cc21]

(1-34)

(1a-a)

The structure of the resulting white powder was identified using NMR. In $^1$H-NMR (CDCl$_3$), the following signals of 48 hydrogens were detected.

δ(ppm)=7.84 (1H),
7.70-7.03 (35H),
1.48 (12H)

Example 7

Compound 1-37

Synthesis of 2-{(biphenyl-4-yl)-phenylamino}-4"-{(9,9-dimethyl-9H-fluoren-2-yl)-phenylamino}-1,1':4',1"-terphenyl The reaction was conducted under the same conditions as in Example 5, except that N-(9,9-dimethyl-9H-fluoren-2-yl)-N-(2"-bromo-1,1':4',1"-terphenyl-4-yl)aniline was used instead of N-(biphenyl-4-yl)-N-(2"-bromo-1,1':4',1"-terphenyl-4-yl)aniline, and N-(biphenyl-4-yl)-N-phenylaniline
was used instead of
2-(phenylamino)-9,9-dimethyl-9H-fluorene.

As a result, 11.7 g (yield 73%) of a white powder of 2-{(biphenyl-4-yl)-phenylamino}-4"-{(9,9-dimethyl-9H-fluoren-2-yl)-phenylamino}-1,1':4',1"-terphenyl (Compound 1-37) was obtained.

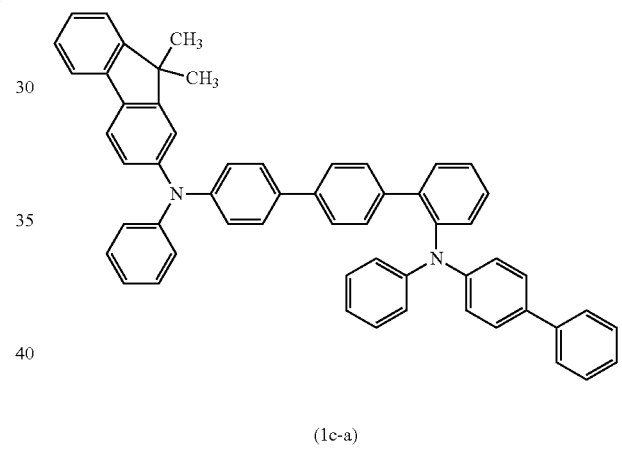

(1-37)

(1c-a)

The structure of the resulting white powder was identified using NMR. In $^1$H-NMR (CDCl$_3$), the following signals of 44 hydrogens were detected.
δ(ppm)=7.68 (1H),
7.64-6.84 (37H),
1.48 (6H)

Example 8

Compound 1-38

Synthesis of 4,4"-bis{N-(9,9-dimethyl-9H-fluoren-2-yl)-phenylamino}-1,1':2',1"-terphenyl The reaction was conducted under the same conditions as in Example 3, except that
1,2-diiodobenzene
was used instead of
1,4-dibromobenzene,
and
4-{(9,9-dimethyl-9H-fluoren-2-yl)-phenylamino}-phenylboronic acid
was used instead of
N-(biphenyl-4-yl)-N-{3-(4,4,5,5-tetramethyl-[1,3,2]dioxaboran-2-yl)phenyl}-phenylamine.

As a result, 6.6 g (yield 39%) of a white powder of 4,4"-bis{N-(9,9-dimethyl-9H-fluoren-2-yl)-phenylamino}-1,1':2',1"-terphenyl (Compound 1-38) was obtained.

(1-38)

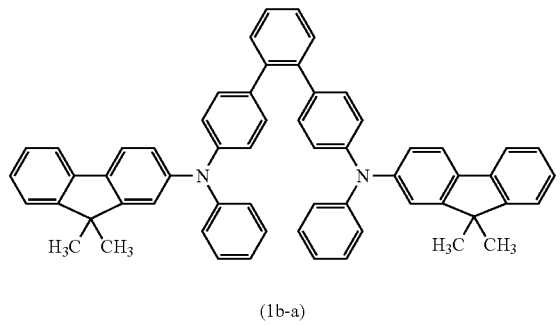

(1b-a)

The structure of the resulting white powder was identified using NMR. In ¹H-NMR (CDCl₃), the following signals of 48 hydrogens were detected.
δ(ppm)=7.64 (2H),
7.58 (2H),
7.45-6.99 (32H)
1.38 (12H)

Example 9

Compound 1-39

Synthesis of 4,4"-bis{N-bis(biphenyl-4-yl)amino}-1,1':2',1"-terphenyl

The reaction was conducted under the same conditions as in Example 3, except that
1,2-diiodobenzene
was used instead of
1,4-dibromobenzene,
and
4-{bis(biphenyl-4-yl)amino}-phenylboronic acid
was used instead of
N-(biphenyl-4-yl)-N-{3-(4,4,5,5-tetramethyl-[1,3,2]diox-aboran-2-yl)phenyl}-phenylamine.
As a result, 4.6 g (yield 24%) of a white powder of 4,4"-bis{N-bis(biphenyl-4-yl)amino}-1,1':2',1"-terphenyl (Compound 1-39) was obtained.

(1-39)

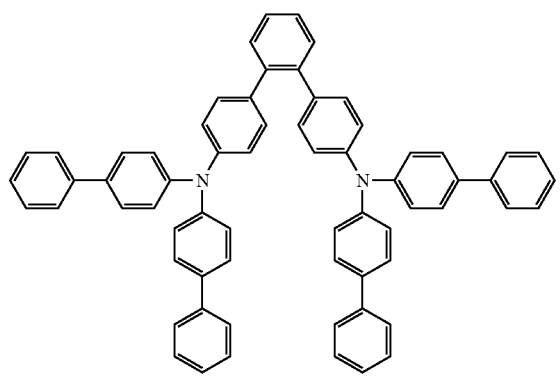

(1b-a)

The structure of the resulting white powder was identified using NMR. In ¹H-NMR (CDCl₃), the following signals of 48 hydrogens were detected.
δ(ppm)=7.57-7.28 (32H),
7.21 (8H),
7.11 (8H)

Example 10

Compound 1-41

Synthesis of 4,4"-bis{(biphenyl-4-yl)-(naphthalen-1-yl)amino}-1,1':2',1"-terphenyl The reaction was conducted under the same conditions as in Example 6, except that
4,4"-dibromo-1,1':2',1"-terphenyl
was used instead of
4,4"-dibromo-1,1':3',1"-terphenyl
and
N-(biphenyl-4-yl)-(naphthalen-1-yl)amine
was used instead of
2-(phenylamino)-9,9-dimethyl-9H-fluorene.
As a result, 5.0 g (yield 30%) of a white powder of 4,4"-bis{(biphenyl-4-yl)-(naphthalen-1-yl)amino}-1,1':2', 1"-terphenyl (Compound 1-41) was obtained.

(1-41)

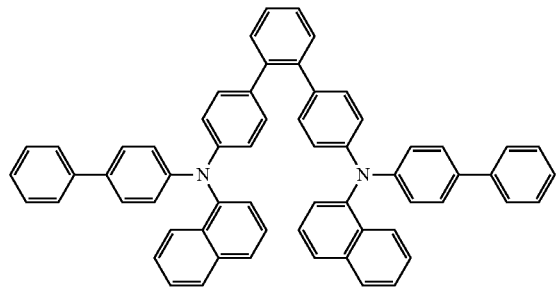

(1b-a)

The structure of the resulting white powder was identified using NMR. In ¹H-NMR (CDCl₃), the following signals of 44 hydrogens were detected.
δ(ppm)=7.93-7.84 (4H),
7.79 (2H),
7.60-7.26 (24H),
7.25-6.92 (14H)

Example 11

Compound 1-42

Synthesis of 4,4"-bis[{4-(naphthalen-1-yl)phenyl}-phenylamino]-1,1':2',1"-terphenyl The reaction was conducted under the same conditions as in Example 6, except that
4,4"-dibromo-1,1':2',1"-terphenyl
was used instead of
4,4"-dibromo-1,1':3',1"-terphenyl
and
{4-(naphthalen-1-yl)phenyl}-phenylamine
was used instead of
2-(phenylamino)-9,9-dimethyl-9H-fluorene.

As a result, 7.3 g (yield 43%) of a white powder of 4,4''-bis[{4-(naphthalen-1-yl)phenyl}-phenylamino]-1,1':2',1''-terphenyl (Compound 1-42) was obtained.

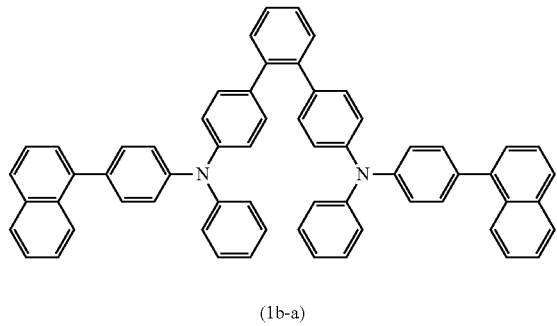

(1-42)

(1b-a)

The structure of the resulting white powder was identified using NMR. In $^1$H-NMR (CDCl$_3$), the following signals of 44 hydrogens were detected.
δ(ppm)=8.01 (2H),
7.91 (2H),
7.84 (2H),
7.53-6.98 (38H)

Example 12

Compound 1-45

Synthesis of 4,4''-bis[{4-(naphthalen-1-yl)phenyl}-phenylamino]-1,1':3',1''-terphenyl The reaction was conducted under the same conditions as in Example 6, except that
{4-(naphthalen-1-yl)phenyl}-phenylamine
was used instead of
2-(phenylamino)-9,9-dimethyl-9H-fluorene.
As a result, 167 g (yield 79%) of a white powder of 4,4''-bis[{4-(naphthalen-1-yl)phenyl}-phenylamino]-1,1':3',1''-terphenyl (Compound 1-45) was obtained.

The structure of the resulting white powder was identified using NMR. In $^1$H-NMR (CDCl$_3$), the following signals of 44 hydrogens were detected.

δ(ppm)=8.08 (2H), 7.94 (2H), 7.90-7.80 (3H), 7.65-7.00 (37H)

Example 13

Compound 1-47

Synthesis of 2,2''-bis{(9,9-dimethyl-9H-fluoren-2-yl)-phenylamino}-1,1':3',1''-terphenyl The reaction was conducted under the same conditions as in Example 3, except that 1,3-diiodobenzene was used instead of 1,4-dibromobenzene and 2-{(9,9-dimethyl-9H-fluoren-2-yl)-phenylamino}-phenylboronic acid was used instead of N-(biphenyl-4-yl)-N-{3-(4,4,5,5-tetramethyl-[1,3,2]dioxaboran-2-yl)phenyl}-phenylamine.

As a result, 4.2 g (yield 25) of a white powder of 2,2''-bis{(9,9-dimethyl-9H-fluoren-2-yl)-phenylamino}-1,1':3',1''-terphenyl (Compound 1-47) was obtained.

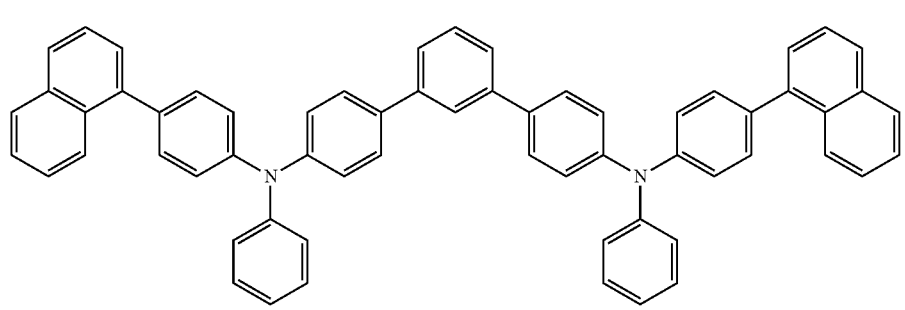

(1-45)

(1a-a)

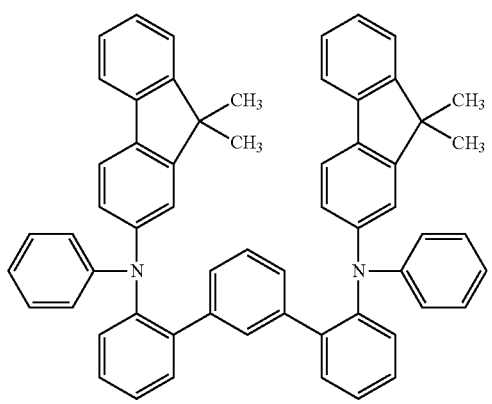

(1-47)

(1a-b)

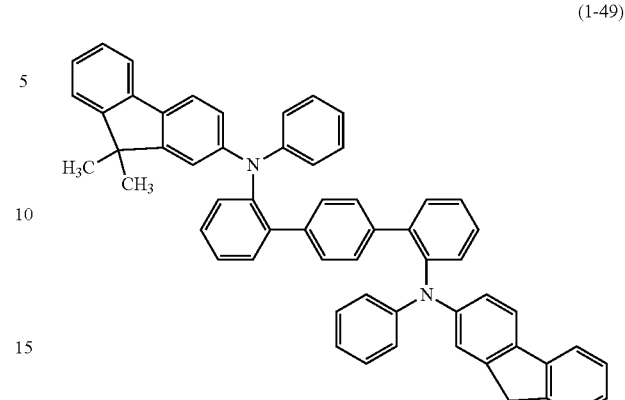

(1-49)

(1c-b)

The structure of the resulting white powder was identified using NMR. In $^1$H-NMR (CDCl$_3$), the following signals of 48 hydrogens were detected.

δ(ppm)=7.60 (2H), 7.38-7.09 (14H), 6.95-6.71 (14H), 6.66-6.56 (4H), 6.35 (2H), 6.26 (12H)

Example 14

Compound 1-49

Synthesis of 2,2"-bis{(9,9-dimethyl-9H-fluoren-2-yl)-phenylamino}-1,1':4',1"-terphenyl The reaction was conducted under the same conditions as in Example 3, except that 2-{(9,9-dimethyl-9H-fluoren-2-yl)-phenylamino}-phenylboronic acid was used instead of N-(biphenyl-4-yl)-N-{3-(4,4,5,5-tetramethyl-[1,3,2]dioxaboran-2-yl)phenyl}-phenylamine.

As a result, 13.7 g (yield 76%) of a white powder of 2,2"-bis{(9,9-dimethyl-9H-fluoren-2-yl)-phenylamino}-1,1':4',1"-terphenyl (Compound 1-49) was obtained.

The structure of the resulting white powder was identified using NMR. In $^1$H-NMR (THF-d$_8$), the following signals of 48 hydrogens were detected.

δ(ppm)=7.53 (2H), 7.35-6.81 (30H), 6.76 (2H), 6.67 (2H), 1.29 (12H)

Example 15

Compound 1-92

Synthesis of 4,4"-bis{N-(2-phenyl-biphenyl-4-yl)-N-phenylamino}-1,1':4',1"-terphenyl

| | |
|---|---|
| A nitrogen-purged reaction vessel was charged with | |
| N-(2-phenyl-biphenyl-4-yl)-N-phenylamine | 13.1 g, |
| 4,4"-diiodo-p-terphenyl | 20.0 g, |
| copper powder | 0.18 g, |
| potassium carbonate | 11.3 g, |
| 3,5-di-tert-bytylsalicylic acid | 0.70 g, |
| sodium hydrogen sulfite | 0.86 g, and |
| dodecylbenzene | 30 ml. |

The mixture was heated and stirred for 24 h at 210° C. A total of 30 ml of xylene and 60 ml of methanol were added under gradual cooling, and the precipitated solids were collected by filtration. The recovered solids were dissolved in toluene, and adsorption purification was performed by adding 40 ml of silica. After condensation, crystallization with ethyl acetate and methanol and then purification by recrystallization using chlorobenzene were performed. The solids were then reflux-washed with 200 ml of methanol. As a result, 17.0 g (yield 72%) of a yellowish white powder of 4,4"-bis{N-(2-phenyl-biphenyl-4-yl)-N-phenylamino}-1,1':4',1"-terphenyl (Compound 1-92) was obtained.

(1-92)

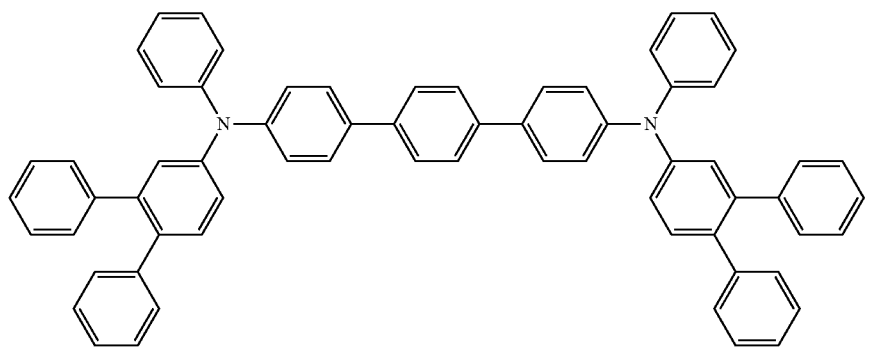

The structure of the resulting white powder was identified using NMR. In ¹H-NMR (CDCl₃), the following signals of 48 hydrogens were detected.
δ(ppm)=7.68 (4H),
7.62-7.55 (4H),
7.38-7.09 (40H)

<Measurement of Melting Point and Glass Transition Point>

The melting point and glass transition point of the arylamine compound of the general formula (1) were determined with a high-sensitivity differential scanning calorimeter (DSC3100SA, manufactured by Bruker AXS K. K.).

|  | Melting point | Glass transition point |
| --- | --- | --- |
| Example 1 (Compound 1-5) | Not measured | 117° C. |
| Example 2 (Compound 1-6) | Not measured | 117° C. |
| Example 3 (Compound 1-21) | 261° C. | 103° C. |
| Example 5 (Compound 1-32) | Not measured | 115° C. |
| Example 6 (Compound 1-34) | 286° C. | 124° C. |
| Example 7 (Compound 1-37) | 218° C. | 114° C. |
| Example 8 (Compound 1-38) | Not measured | 119° C. |
| Example 9 (Compound 1-39) | Not measured | 106° C. |
| Example 10 (Compound 1-41) | Not measured | 127° C. |
| Example 11 (Compound 1-42) | Not measured | 111° C. |
| Example 12 (Compound 1-45) | Not measured | 122° C. |
| Example 13 (Compound 1-47) | 239° C. | 116° C. |
| Example 14 (Compound 1-49) | 269° C. | 117° C. |
| Example 15 (Compound 1-92) | 249° C. | 124° C. |

The arylamine compound of the general formula (1) has a glass transition point of 100° C. or more which indicates a stable thin-film state.

<Measurement of Work Function>

A vapor-deposited film with a thickness of 100 nm was produced on an ITO substrate by using the arylamine compound of the general formula (1), and the work function was measured with an ionization potential measuring device (PYS-202, manufactured by Sumitomo Heavy Industries, Ltd.).

|  | Work function |
| --- | --- |
| Example 1 (Compound 1-5) | 5.68 eV |
| Example 2 (Compound 1-6) | 5.65 eV |
| Example 3 (Compound 1-21) | 5.79 eV |
| Example 4 (Compound 1-22) | 5.83 eV |
| Example 5 (Compound 1-32) | 5.69 eV |
| Example 6 (Compound 1-34) | 5.65 eV |
| Example 7 (Compound 1-37) | 5.67 eV |
| Example 8 (Compound 1-38) | 5.64 eV |
| Example 9 (Compound 1-39) | 5.66 eV |
| Example 10 (Compound 1-41) | 5.69 eV |
| Example 11 (Compound 1-42) | 5.75 eV |
| Example 12 (Compound 1-45) | 5.76 eV |
| Example 13 (Compound 1-47) | 5.72 eV |
| Example 14 (Compound 1-49) | 5.72 eV |
| Example 15 (Compound 1-92) | 5.67 eV |

The arylamine compound of the general formula (1) shows an advantageous energy level and has a satisfactory hole transport capacity when compared with the work function of 5.4 eV of the typical hole transport materials such as NPD and TPD.

Example 16

Compound 2-1

Synthesis of 7,7-dimethyl-12-(4-phenylquinazolin-2-yl)-7,12-dihydrobenzo[4,5]thieno[3,2-g]indeno[1,2-b]indole;

A nitrogen-purged reaction vessel was charged with

| 7,7-dimethyl-7,12-dihydrobenzo[4,5]thieno[3,2-g]indeno[1,2-b]indole | 4.9 g, |
| --- | --- |
| 2-chloro-4-phenylquinazoline | 5.7 g, |
| tris(dibenzylideneacetone)dipalladium | 0.3 g, |
| tri-tert-butylphosphonium tetrafluoroborate | 0.4 g, |
| tert-butoxysodium | 4.0 g, and |
| xylene | 74 ml. |

The mixture was heated and stirred for 12 h under refluxing. After cooling to room temperature, ethyl acetate and water were added and an organic layer was collected by a fractionation operation. The organic layer was concentrated and purified by column chromatography. As a result, 3.0 g (yield 38%) of a powder of 7,7-dimethyl-12-(4-phenylquinazolin-2-yl)-7,12-dihydrobenzo[4,5]thieno[3,2-g]indeno[1,2-b]indole (Compound 2-1) was obtained.

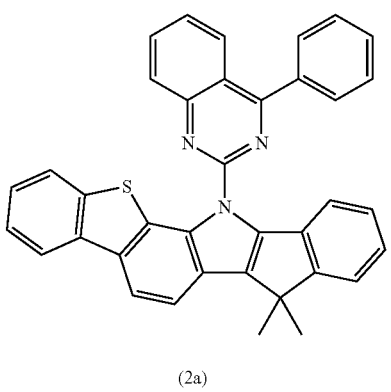

(2-1)

(2a)

Example 17

Compound 2-2

Synthesis of 7,7-dimethyl-12-(4-phenylbenzo[h]
quinazolin-2-yl)-7,12-dihydrobenzo[4,5]thieno[3,2-
g]indeno[1,2-b]indole The reaction was conducted under the same conditions as
in Example 16, except that
2-chloro-4-phenylbenzo[h]quinazoline
was used instead of
2-chloro-4-phenylquinazoline.
As a result, 3.2 g (yield 38%) of a powder of 7,7-dimethyl-
12-(4-phenylbenzo[h]quinazolin-2-yl)-7,12-dihydrobenzo
[4,5]thieno[3,2-g]indeno[1,2-b]indole (Compound 2-2) was
obtained.

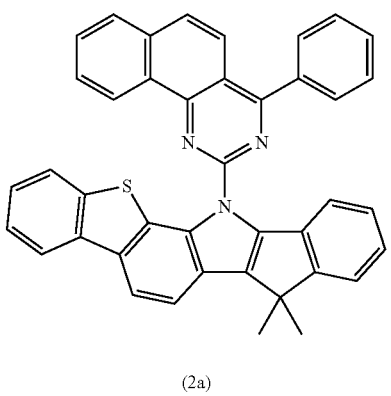

(2-2)

(2a)

Example 18

Compound 2-3

Synthesis of 12-(4,7-diphenylquinazolin-2-yl)-7,7-
dimethyl-7,12-dihydrobenzo[4,5]thieno[3,2-g]in-
deno[1,2-b]indole The reaction was conducted under the same conditions as
in Example 16, except that
2-chloro-4,7-diphenylquinazoline
was used instead of
2-chloro-4-phenylquinazoline.
As a result, 3.3 g (yield 38%) of a powder of 12-(4,7-
diphenylquinazolin-2-yl)-7,7-dimethyl-7,12-dihydrobenzo
[4,5]thieno[3,2-g]indeno[1,2-b]indole (Compound 2-3) was
obtained.

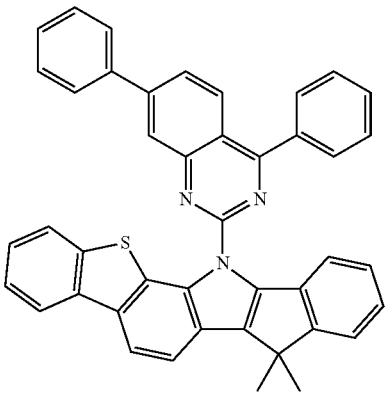

(2-3)

(2a)

Example 19

Compound 2-4

Synthesis of 12-(4,6-diphenylquinazolin-2-yl)-7,7-
dimethyl-7,12-dihydrobenzo[4,5]thieno[3,2-g]in-
deno[1,2-b]indole The reaction was conducted under the same conditions as
in Example 16, except that
2-chloro-4,6-diphenylquinazoline
was used instead of
2-chloro-4-phenylquinazoline.
As a result, 3.3 g (yield 38%) of a powder of 12-(4,6-
diphenylquinazolin-2-yl)-7,7-dimethyl-7,12-dihydrobenzo
[4,5]thieno[3,2-g]indeno[1,2-b]indole (Compound 2-4) was
obtained.

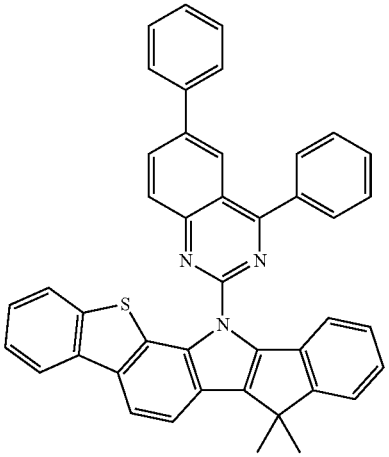

(2-4)

(2a)

Example 20

Compound 2-5

Synthesis of 13,13-dimethyl-8-(4-phenylquinazolin-2-yl)-8,13-dihydrobenzo[4,5]thieno[3,2-e]indeno[1,2-b]indole The reaction was conducted under the same conditions as in Example 16, except that 13,13-dimethyl-8,13-dihydrobenzo[4,5]thieno[3,2-e]indeno[1,2-b]indole was used instead of 7,7-dimethyl-7,12-dihydrobenzo[4,5]thieno[3,2-g]indeno[1,2-b]indole.

As a result, 3.0 g (yield 33%) of a powder of 13,13-dimethyl-8-(4-phenylquinazolin-2-yl)-8,13-dihydrobenzo[4,5]thieno[3,2-e]indeno[1,2-b]indole (Compound 2-5) was obtained.

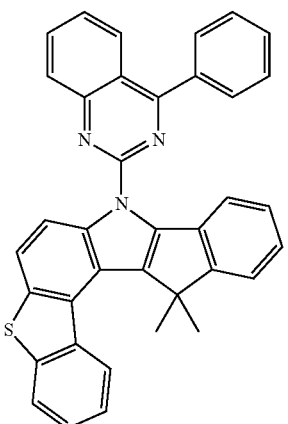

(2-5)

(2b)

Example 21

Compound 2-6

Synthesis of 8-(4,6-diphenylquinazolin-2-yl)-13,13-dimethyl-8,13-dihydrobenzo[4,5]thieno[3,2-e]indeno[1,2-b]indole The reaction was conducted under the same conditions as in Example 20, except that 2-chloro-4,6-diphenylquinazoline was used instead of 2-chloro-4-phenylquinazoline.

As a result, 3.3 g (yield 38) of a powder of 8-(4,6-diphenylquinazolin-2-yl)-13,13-dimethyl-8,13-dihydrobenzo[4,5]thieno[3,2-e]indeno[1,2-b]indole (Compound 2-6) was obtained.

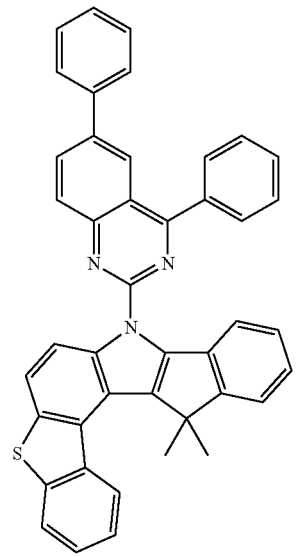

(2-6)

(2b)

Example 22

Compound 2-7

Synthesis of 7,7,13,13-tetramethyl-5-(4-phenylquinazolin-2-yl)-7,13-dihydro-5H-diindeno[1,2-b:1',2'-f]indole The reaction was conducted under the same conditions as in Example 16, except that 7,7,13,13-tetramethyl-7,13-dihydro-5H-diindeno[1,2-b:1',2'-f]indole was used instead of 7,7-dimethyl-7,12-dihydrobenzo[4,5]thieno[3,2-g]indeno[1,2-b]indole.

As a result, 3.0 g (yield 38%) of a powder of 7,7,13,13-tetramethyl-5-(4-phenylquinazolin-2-yl)-7,13-dihydro-5H-diindeno[1,2-b:1',2'-f]indole (Compound 2-7) was obtained.

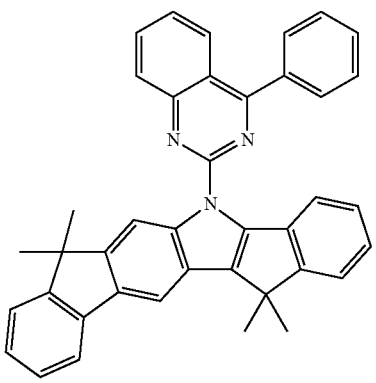

(2-7)

(2c)

Example 23

Compound 2-8

Synthesis of 7,7,13,13-tetramethyl-5-[3-(4-phenylquinazolin-2-yl)phenyl]-7,13-dihydro-5H-diindeno[1,2-b:1',2'-f]indole The reaction was conducted under the same conditions as in Example 22, except that 2-(3-bromophenyl)-4-phenylquinazoline was used instead of 2-chloro-4-phenylquinazoline.

As a result, 3.4 g (yield 38%) of a powder of 7,7,13,13-tetramethyl-5-[3-(4-phenylquinazolin-2-yl)phenyl]-7,13-dihydro-5H-diindeno[1,2-b:1',2'-f]indole (Compound 2-8) was obtained.

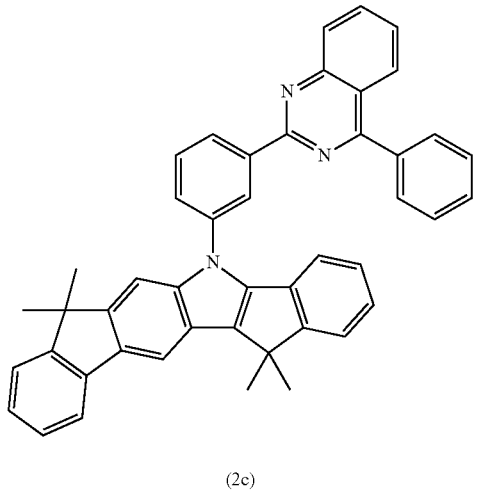

(2-8)

Example 24

Compound 2-9

Synthesis of 7,7-dimethyl-12-(4-phenylbenzo[h]quinazolin-2-yl)-7,12-dihydrobenzofuro[3,2-g]indeno[1,2-b]indole The reaction was conducted under the same conditions as in Example 17, except that 7,7-dimethyl-7,12-dihydrobenzofuro[3,2-g]indeno[1,2-b]indole was used instead of 7,7-dimethyl-7,12-dihydrobenzo[4,5]thieno[3,2-g]indeno[1,2-b]indole.

As a result, 3.0 g (yield 38%) of a powder of 7,7-dimethyl-12-(4-phenylbenzo[h]quinazolin-2-yl)-7,12-dihydrobenzofuro[3,2-g]indeno[1,2-b]indole (Compound 2-9) was obtained.

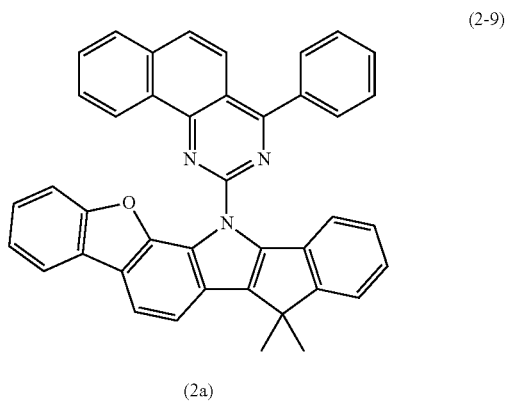 [SMILES: CC1(C)c2ccccc2-c2c1c1ccc3c4ccccc4oc3c1n2-c1nc(-c2ccccc2)c2ccc3ccccc3c2n1]

(2a)

Example 25

Compound 2-10

Synthesis of 12-(4,6-diphenylbenzo[h]quinazolin-2-yl)-7,7-dimethyl-7,12-dihydrobenzofuro[3,2-g]indeno[1,2-b]indole The reaction was conducted under the same conditions as in Example 24, except that 2-chloro-4,6-diphenylbenzo[h]quinazoline was used instead of 2-chloro-4-phenylbenzo[h]quinazoline.

As a result, 3.5 g (yield 38%) of a powder of 12-(4,6-diphenylbenzo[h]quinazolin-2-yl)-7,7-dimethyl-7,12-dihydrobenzofuro[3,2-g]indeno[1,2-b]indole (Compound 2-10) was obtained.

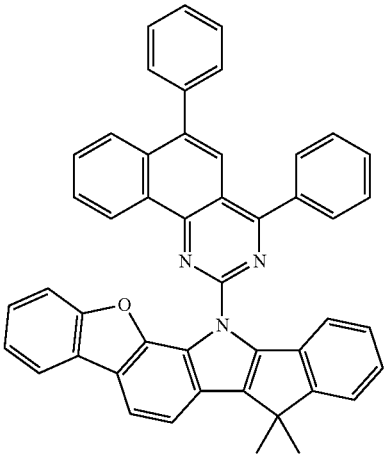

(2a)

Example 26

Compound 2-11

Synthesis of 13,13-dimethyl-8-(4-phenylquinazolin-2-yl)-8,13-dihydrobenzofuro[3,2-e]indeno[1,2-b]indole The reaction was conducted under the same conditions as in Example 16, except that
13,13-dimethyl-8,13-dihydrobenzofuro[3,2-e]indeno[1,2-b]indole
was used instead of
7,7-dimethyl-7,12-dihydrobenzo[4,5]thieno[3,2-g]indeno[1,2-b]indole.
As a result, 3.0 g (yield 38%) of a powder of 13,13-dimethyl-8-(4-phenylquinazolin-2-yl)-8,13-dihydrobenzofuro[3,2-e]indeno[1,2-b]indole (Compound 2-11) was obtained.

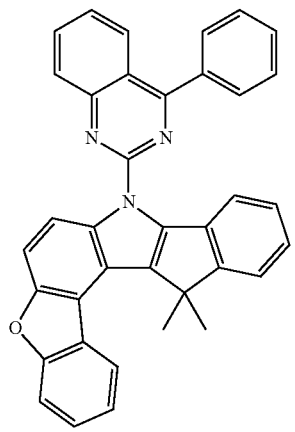

(2-11)

Example 27

Compound 2-12

Synthesis of 13,13-dimethyl-8-(4,6-diphenylquinazolin-2-yl)-8,13-dihydrobenzofuro[3,2-e]indeno[1,2-b]indole The reaction was conducted under the same conditions as in Example 26, except that
2-chloro-4,6-diphenylquinazoline
was used instead of
2-chloro-4-phenylquinazoline.
As a result, 3.2 g (yield 38%) of a powder of 13,13-dimethyl-8-(4,6-diphenylquinazolin-2-yl)-8,13-dihydrobenzofuro[3,2-e]indeno[1,2-b]indole (Compound 2-12) was obtained.

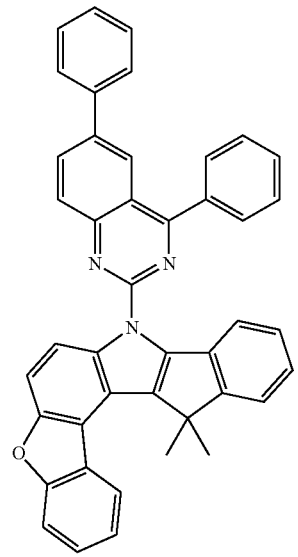

(2-12)

(2b)

Example 28

Compound 3-1

Synthesis of 13-(4,6-diphenylquinazolin-2-yl)-7,7-dimethyl-7,13-dihydroindeno[2',1':4,5]thieno[2,3-a]carbazole The reaction was conducted under the same conditions as in Example 27, except that
7,7-dimethyl-7,13-dihydroindeno[2',1':4,5]thieno[2,3-a]carbazole
was used instead of
13,13-dimethyl-8,13-dihydrobenzofuro[3,2-e]indeno[1,2-b]indole.
As a result, 7.0 g (yield 38%) of a powder of 13-(4,6-diphenylquinazolin-2-yl)-7,7-dimethyl-7,13-dihydroindeno[2',1':4,5]thieno[2,3-a]carbazole (Compound 3-1) was obtained.

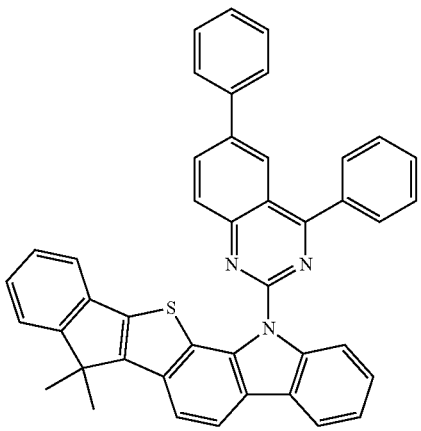

(3-1)

(3a-1)

Example 29

Compound 3-2

Synthesis of 13-[4-(biphenyl-4-yl)-quinazolin-2-yl]-7,7-dimethyl-7,13-dihydroindeno[2',1':4,5]thieno[2,3-]carbazole The reaction was conducted under the same conditions as in Example 28, except that 4-(biphenyl-4-yl)-2-chloroquinazoline was used instead of 2-chloro-4,6-diphenylquinazoline.

As a result, 6.7 g (yield 37%) of a powder of 13-[4-(biphenyl-4-yl)-quinazolin-2-yl]-7,7-dimethyl-7,13-dihydroindeno[2',1':4,5]thieno[2,3-a]carbazole (Compound 3-2) was obtained.

(3-2)

(3a-1)

Example 30

Compound 3-3

Synthesis of 7,7-dimethyl-13-[4-(phenyl-$d_5$)-quinazolin-2-yl]-7,13-dihydroindeno[2',1':4,5]thieno[2,3-a]carbazole The reaction was conducted under the same conditions as in Example 28, except that 2-chloro-4-(phenyl-$d_5$) quinazoline was used instead of 2-chloro-4,6-diphenylquinazoline.

As a result, 8.4 g (yield 32%) of a powder of 7,7-dimethyl-13-[4-(phenyl-$d_5$)-quinazolin-2-yl]-7,13-dihydroindeno[2',1':4,5]thieno[2,3-a]carbazole (Compound 3-3) was obtained.

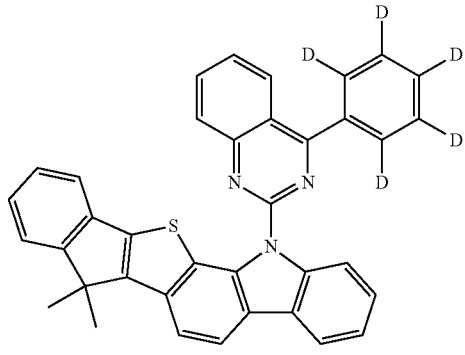

(3-3)

(3a-1)

Example 31

Compound 3-4

Synthesis of 7,7-dimethyl-13-[4-(4-phenylquinazolin-2-yl)phenyl]-7,13-dihydroindeno[2',1':4,5]thieno[2,3-a]carbazole The reaction was conducted under the same conditions as in Example 28, except that 2-(4-bromophenyl)-4-phenylquinazoline was used instead of 2-chloro-4,6-diphenylquinazoline.

As a result, 5.2 g (yield 28%) of a powder of 7,7-dimethyl-13-[4-(4-phenylquinazolin-2-yl)phenyl]-7,13-dihydroindeno[2',1':4,5]thieno[2,3-a]carbazole (Compound 3-4) was obtained.

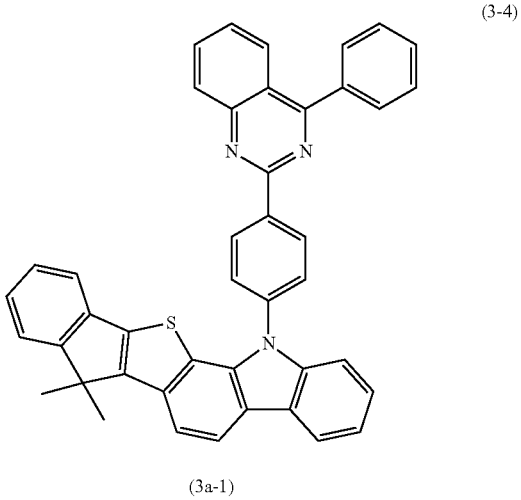 [SMILES: CC1(C)c2ccccc2-c2sc3c(ccc4c5ccccc5n(-c5ccc(-c6nc(-c7ccccc7)c7ccccc7n6)cc5)c43)c21]

(3-4)

(3a-1)

Example 32

Compound 3-5

Synthesis of 7,7-dimethyl-13-[3-(4-phenylquinazo-lin-2-yl)phenyl]-7,13-dihydroindeno[2',1':4,5]thieno[2,3-a]carbazole The reaction was conducted under the same conditions as in Example 28, except that 2-(3-bromophenyl)-4-phenylquinazoline was used instead of 2-chloro-4,6-diphenylquinazoline.

As a result, 8.4 q (yield 32%) of a powder of 7,7-dimethyl-13-[3-(4-phenylquinazolin-2-yl)phenyl]-7,13-dihydroindeno[2',1':4,5]thieno[2,3-a]carbazole (Compound 3-5) was obtained.

(3-5)

(3a-1)

Example 33

Compound 3-6

Synthesis of 7,7-dimethyl-13-(4-phenylbenzo[h]quinazolin-2-yl)-7,13-dihydroindeno[2',1':4,5]thieno[2,3-a]carbazole The reaction was conducted under the same conditions as in Example 28, except that 2-chloro-4-phenylbenzo[h]quinazoline was used instead of 2-chloro-4,6-diphenylquinazoline.

As a result, 8.4 g (yield 32%) of a powder of 7,7-dimethyl-13-(4-phenylbenzo[h]quinazolin-2-yl)-7,13-dihydroindeno[2',1':4,5]thieno[2,3-a]carbazole (Compound 3-6) was obtained.

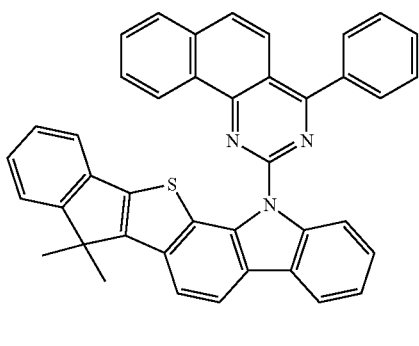

(3-6)

(3a-1)

Example 34

Compound 3-7

Synthesis of 8,8-dimethyl-5-(4-phenylbenzo[n]quinazolin-2-yl)-5,8-dihydroindeno[2',1':4,5]thieno[3,2-c]carbazole The reaction was conducted under the same conditions as in Example 33, except that 8,8-dimethyl-5,8-dihydroindeno[2',1':4,5]thieno[3,2-c]carbazole was used instead of 7,7-dimethyl-7,13-dihydroindeno[2',1':4,5]thieno[2,3-a]carbazole.

As a result, 9.3 g (yield 35%) of a powder of 8,8-dimethyl-5-(4-phenylbenzo[h]quinazolin-2-yl)-5,8-dihydroindeno[2',1':4,5]thieno[3,2-c]carbazole (Compound 3-7) was obtained.

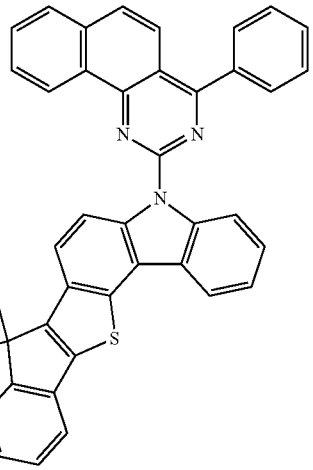

(3-7)

(3a-3)

Example 35

Compound 3-8

Synthesis of 7,7-dimethyl-13-(4-phenylquinazolin-2-yl)-7,13-dihydroindeno[2',1':4,5]furo[2,3-a]carbazole The reaction was conducted under the same conditions as in Example 16, except that 7,7-dimethyl-7,13-dihydroindeno[2',1':4,5]furo[2,3-a]carbazole was used instead of 7,7-dimethyl-7,12-dihydrobenzo[4,5]thieno[3,2-g]indeno[1,2-b]indole.

As a result, 6.2 g (yield 32%) of a powder of 7,7-dimethyl-13-(4-phenylquinazolin-2-yl)-7,13-dihydroindeno[2',1':4,5]furo[2,3-a]carbazol (Compound 3-8) was obtained.

(3-8)

(3a-1)

Example 36

Compound 3-9

Synthesis of 7,7-dimethyl-13-(4-phenylbenzo[h]quinazolin-2-yl)-7,13-dihydroindeno[2',1':4,5]furo[2,3-a]carbazole The reaction was conducted under the same conditions as in Example 35, except that 2-chloro-4-phenylbenzo[h]quinazoline was used instead of 2-chloro-4-phenylquinazoline.

As a result, 8.6 g (yield 30) of a powder of 7,7-dimethyl-13-(4-phenylbenzo[h]quinazolin-2-yl)-7,13-dihydroindeno[2',1':4,5]furo[2,3-a]carbazole (Compound 3-9) was obtained.

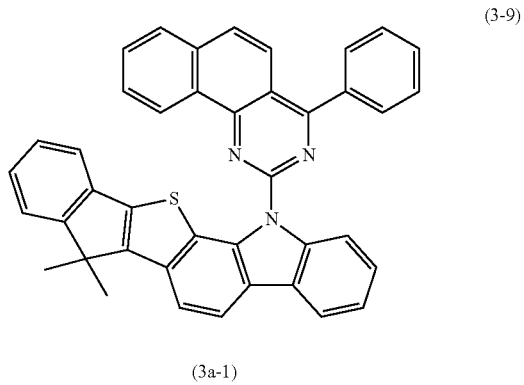 [SMILES: CC1(C)c2ccccc2-c2sc3c(ccc4c5ccccc5n(-c5nc(-c6ccccc6)c6ccc7ccccc7c6n5)c43)c21]

(3-9)

(3a-1)

Example 37

Compound 3-10

Synthesis of 13-(4,6-diphenylquinazolin-2-yl)-7,7-dimethyl-7,13-dihydroindeno[2',1':4,5]furo[2,3-a]carbazole The reaction was conducted under the same conditions as in Example 35, except that 2-chloro-4,6-diphenylquinazoline was used instead of 2-chloro-4-phenylquinazoline.

As a result, 7.2 g (yield 29%) of a powder of 13-(4,6-diphenylquinazolin-2-yl)-7,7-dimethyl-7,13-dihydroindeno[2',1':4,5]furo[2,3-a]carbazole (Compound 3-10) was obtained.

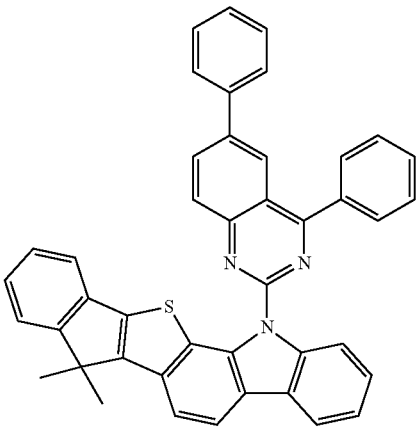

(3-10)

(3a-1)

Example 38

Compound 3-11

Synthesis of 7,7-diphenyl-13-(4-phenylquinazolin-2-yl)-7,13-dihydroindeno[2',1':4,5]thieno[2,3-a]carbazole The reaction was conducted under the same conditions as in Example 16, except that 7,7-diphenyl-7,13-dihydroindeno[2',1':4,5]thieno[2,3-a]carbazole was used instead of 7,7-dimethyl-7,12-dihydrobenzo[4,5]thieno[3,2-g]indeno[1,2-b]indole.

As a result, 6.7 g (yield 37) of a powder of 7,7-diphenyl-13-(4-phenylquinazolin-2-yl)-7,13-dihydroindeno[2',1':4,5]thieno[2,3-a]carbazole (Compound 3-11) was obtained.

(3-11)

(3a-4)

Example 39

Compound 3-12

Synthesis of 9,9-dimethyl-15-(4-phenylquinazolin-2-yl)-9,15-dihydrobenzo[a]indeno[2',1':4,5]thieno[3,2-i]carbazoles The reaction was conducted under the same conditions as in Example 16, except that 9,9-dimethyl-9,15-dihydrobenzo[a]indeno[2',1':4,5]thieno[3,2-i]carbazole was used instead of 7,7-dimethyl-7,12-dihydrobenzo[4,5]thieno[3,2-g]indeno[1,2-b]indole.

As a result, 4.8 g (yield 42%) of a powder of 9,9-dimethyl-15-(4-phenylquinazolin-2-yl)-9,15-dihydrobenzo[a]indeno[2',1':4,5]thieno[3,2-i]carbazole (Compound 3-12) was obtained.

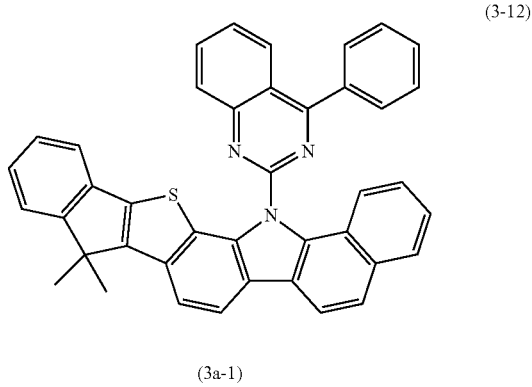 [SMILES: CC1(C)c2ccccc2-c2sc3c(ccc4c5ccc6ccccc6c5n(-c5nc(-c6ccccc6)c6ccccc6n5)c43)c21]

(3-12)

(3a-1)

Example 40

Compound 3-13

Synthesis of 7-phenyl-13-(4-phenylquinazolin-2-yl)-7,13-dihydroindolo[2',3':4,5]thieno[2,3-a]carbazole The reaction was conducted under the same conditions as in Example 16, except that 7-phenyl-7,13-dihydroindolo[2',3':4,5]thieno[2,3-a]carbazole was used instead of 7,7-dimethyl-7,12-dihydrobenzo[4,5]thieno[3,2-g]indeno[1,2-b]indole.

As a result, 4.3 g (yield 43%) of a powder of 7-phenyl-13-(4-phenylquinazolin-2-yl)-7,13-dihydroindolo[2',3':4,5]thieno[2,3-a]carbazole (Compound 3-13) was obtained.

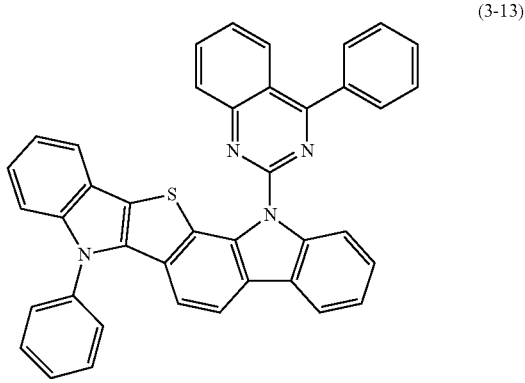

(3-13)

(3b-1)

Example 41

Compound 3-14

Synthesis of 12,12-dimethyl-1-(4-phenylquinazolin-2-yl)-1,12-dihydroindeno[1',2':4,5]thieno[2,3-a]carbazole The reaction was conducted under the same conditions as in Example 16, except that 12,12-dimethyl-1,12-dihydroindeno[1',2':4,5]thieno[2,3-a]carbazole was used instead of 7,7-dimethyl-7,12-dihydrobenzo[4,5]thieno[3,2-g]indeno[1,2-b]indole.

As a result, 6.3 g (yield 44%) of a powder of 12,12-dimethyl-1-(4-phenylquinazolin-2-yl)-1,12-dihydroindeno[1',2':4,5]thieno[2,3-a]carbazole (Compound 3-14) was obtained.

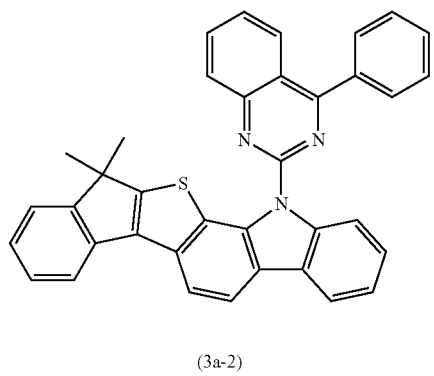

(3-14)

Example 42

Compound 3-15

Synthesis of 7,7-dimethyl-13-(naphthalen-2-yl)-7,13-dihydroindeno[2',1':4,5]thieno[2,3-a]carbazole The reaction was conducted under the same conditions as in Example 28, except that 2-bromonaphthalene was used instead of 2-chloro-4,6-diphenylquinazoline.

As a result, 5.4 g (yield 47%) of a powder of 7,7-dimethyl-13-(naphthalen-2-yl)-7,13-dihydroindeno[2',1':4,5]thieno[2,3-a]carbazole (Compound 3-15) was obtained.

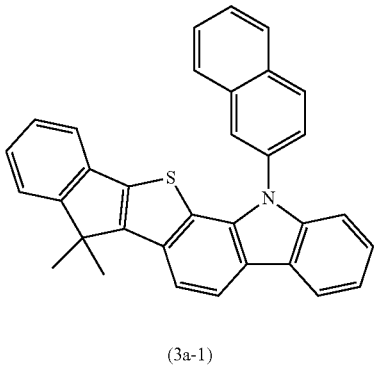

(3-15)

(3a-1)

Example 43

An organic EL device was produced, as depicted in FIG. 1, by forming in advance an ITO electrode as the transparent anode 2 on the glass substrate 1, and then vapor depositing thereon the hole injection layer 3, the first hole transport layer 5a, the second hole transport layer 5b, the luminous layer 6, the electron transport layer 7, the electron injection layer 8, and the cathode (aluminum electrode) 9 in the order of description.

More specifically, the glass substrate 1 on which an ITO film with a thickness of 150 nm was grown was ultrasonically cleaned for 20 min in isopropyl alcohol and then dried for 10 min on a hot plate heated to 200° C. Then, UV/ozone treatment was performed for 15 min, the ITO-attached glass substrate was attached inside a vacuum vapor deposition device, and pressure was reduced to 0.001 Pa or less.

Then, HIM-1 of the structural formula indicated below was formed to a film thickness of 5 nm as the hole injection layer 3 so as to cover the transparent electrode 2.

A triarylamine derivative (6-1) represented by the structural formula indicated below was formed as the first hole transport layer 5a to a film thickness of 60 nm on the hole injection layer 3. This triarylamine derivative had two triphenylamine structures in a molecule.

The Compound (1-5) of Example 1 was formed as the second hole transport layer 5b to a film thickness of 5 nm on the first hole transport layer 5a.

A compound EMD-1 of the structural formula indicated below and the Compound (2-4) of Example 19 were formed as the luminous layer 6 to a film thickness of 20 nm on the second hole transport layer 5b by binary vapor deposition at vapor deposition rates such that the vapor deposition rate ratio of EMD-1 to Compound (2-4) was 5:95.

A benzotriazole derivative (4-1) of the structural formula indicated below and ETM-1 of the structural formula indicated below were formed as the electron transport layer 7 to a film thickness of 30 nm on the luminous layer 6 by binary vapor deposition at vapor deposition rates such that the vapor deposition rate ratio of the benzotriazole derivative (4-1) to ETM-1 was 50:50.

Lithium fluoride was formed as the electron injection layer 8 to a film thickness of 1 nm on the electron transport layer 7.

Finally, the cathode 9 was formed by vapor depositing aluminum to 100 nm.

The produced organic EL device was measured for the light emission characteristics exhibited when a direct current voltage was applied at normal temperature in the atmosphere. The results of the measurements are shown in Table 1.

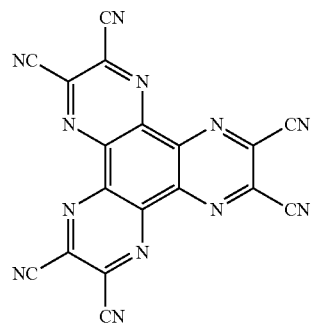
(HIM-1)
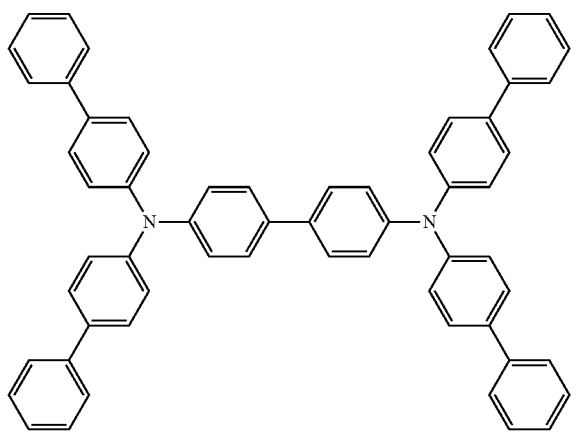
(6-1)
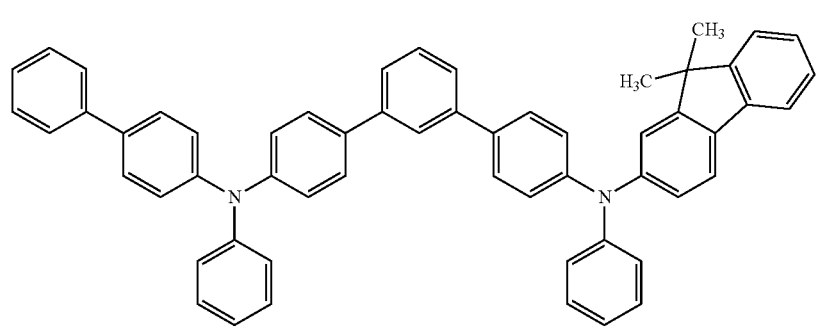
(1a-a)
(1-5)
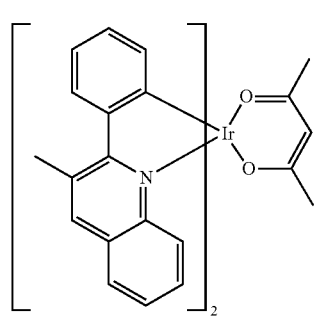
(EMD-1)
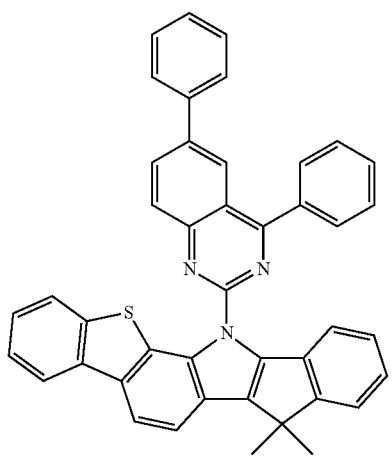
(2-4)
(2a)

-continued (4-1)

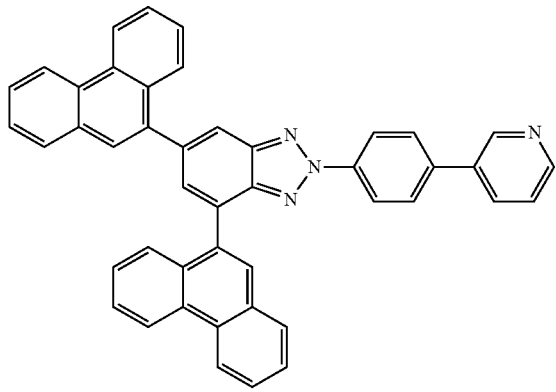

(4a) (4c)

(ETM-1)

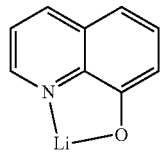

Example 44

An organic EL device was prepared under the same conditions as in Example 43, except that the Compound (1-32) of Example 5 was used instead of the Compound (1-5) as the material for the second hole transport layer 5b. The resulting organic EL device was measured for the light emission characteristics exhibited when a direct current voltage was applied at normal temperature in the atmosphere. The results of the measurements are shown in Table 1.

(1-32)

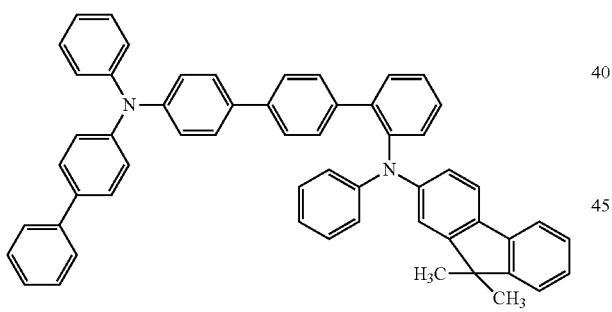

(1c-a)

Example 45

An organic EL device was prepared under the same conditions as in Example 43, except that the Compound (1-34) of Example 6 was used instead of the Compound (1-5) as the material for the second hole transport layer 5b. The resulting organic EL device was measured for the light emission characteristics exhibited when a direct current voltage was applied at normal temperature in the atmosphere. The results of the measurements are shown in Table 1.

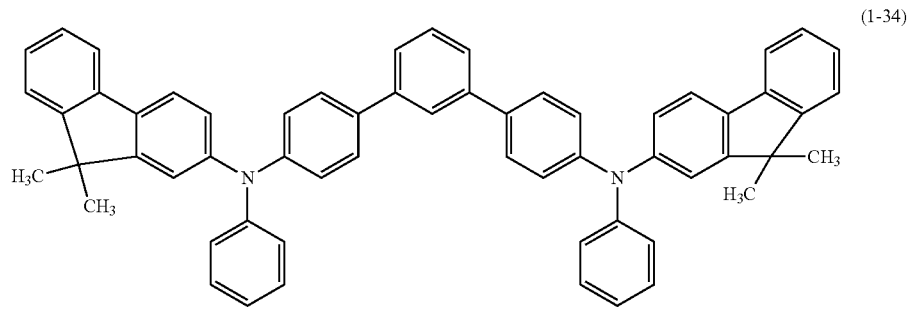

(1a-a)

Example 46

An organic EL device was prepared under the same conditions as in Example 43, except that the Compound (1-37) of Example 7 was used instead of the Compound (1-5) as the material for the second hole transport layer 5b. The resulting organic EL device was measured for the light emission characteristics exhibited when a direct current voltage was applied at normal temperature in the atmosphere. The results of the measurements are shown in Table 1.

Example 47

An organic EL device was prepared under the same conditions as in Example 43, except that the Compound (1-38) of Example 8 was used instead of the Compound (1-5) as the material for the second hole transport layer 5b. The resulting organic EL device was measured for the light emission characteristics exhibited when a direct current voltage was applied at normal temperature in the atmosphere. The results of the measurements are shown in Table 1.

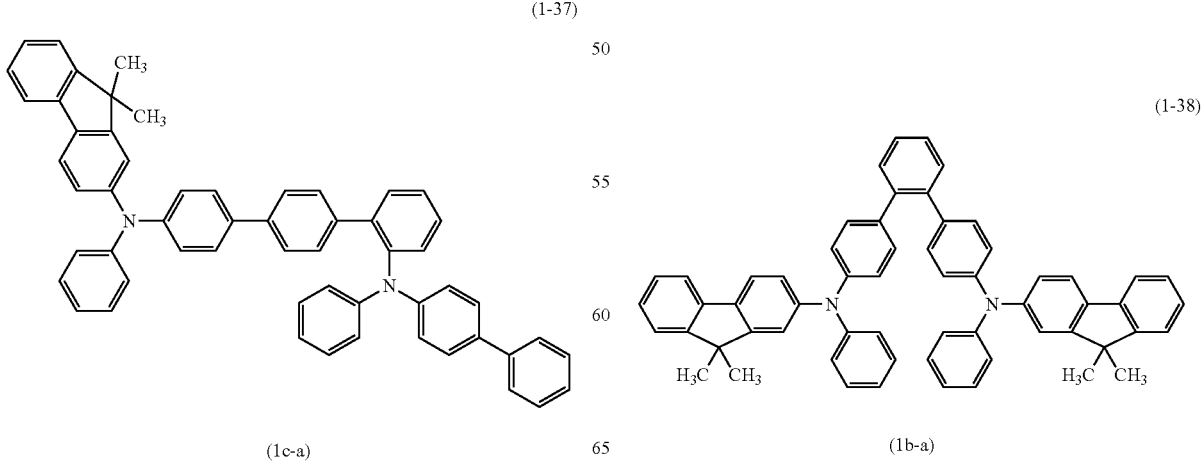

(1c-a)  (1b-a)

Example 48

An organic EL device was prepared under the same conditions as in Example 43, except that the Compound (1-49) of Example 14 was used instead of the Compound (1-5) as the material for the second hole transport layer 5b. The resulting organic EL device was measured for the light emission characteristics exhibited when a direct current voltage was applied at normal temperature in the atmosphere. The results of the measurements are shown in Table 1.

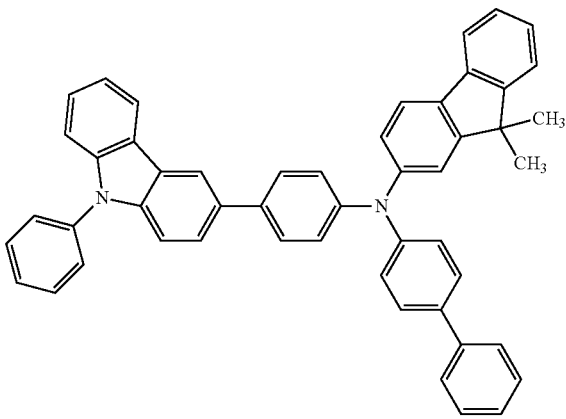

(6'-2)

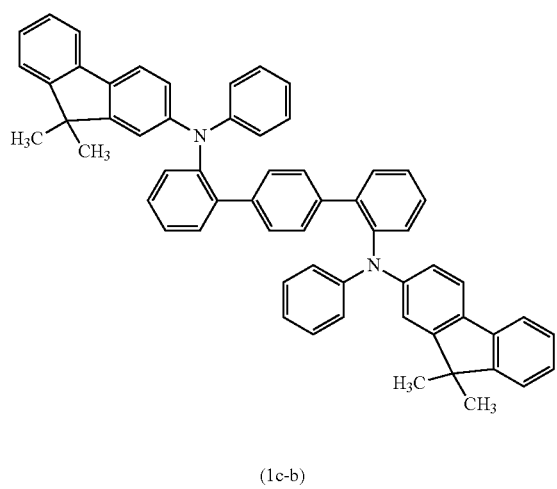

(1-49)

Example 49

An organic EL device was prepared under the same conditions as in Example 43, except that the Compound (3-14) of Example 41 was used instead of the Compound (2-4) as the material for the luminous layer 6. The resulting organic EL device was measured for the light emission characteristics exhibited when a direct current voltage was applied at normal temperature in the atmosphere. The results of the measurements are shown in Table 2.

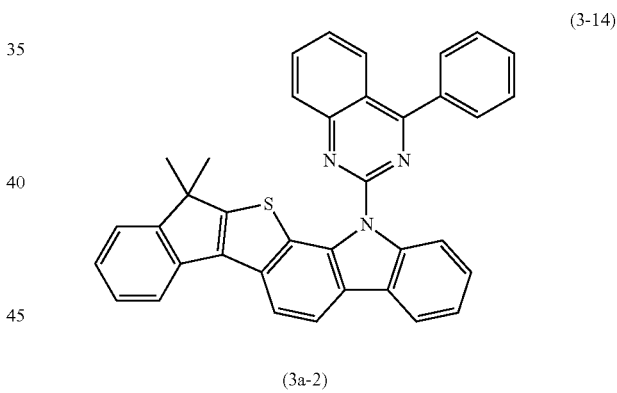

(3-14)

(3a-2)

(1c-b)

Comparative Example 1

For comparison, an organic EL device was produced under the same conditions as in Example 43, except that an arylamine Compound (6'-2) of the structural formula indicated below was used instead of the triarylamine derivative (6-1) as the material for the first hole transport layer 5a, and an arylamine Compound (6'-2) of the structural formula indicated below was used instead of the Compound (1-5) as the material for the second hole transport layer 5b. In this case, the first hole transport layer 5a and the second hole transport layer 5b function as an integrated hole transport layer (thickness 65 nm). The produced organic EL device was measured for the light emission characteristics exhibited when a direct current voltage was applied at normal temperature in the atmosphere. The results of the measurements are shown in Table 1.

Example 50

An organic EL device was prepared under the same conditions as in Example 49, except that the Compound (1-32) of Example 5 was used instead of the Compound (1-5) as the material for the second hole transport layer 5b. The resulting organic EL device was measured for the light emission characteristics exhibited when a direct current voltage was applied at normal temperature in the atmosphere. The results of the measurements are shown in Table 2.

Example 51

An organic EL device was prepared under the same conditions as in Example 49, except that the Compound (1-34) of Example 6 was used instead of the Compound (1-5) as the material for the second hole transport layer 5b. The resulting organic EL device was measured for the light emission characteristics exhibited when a direct current voltage was applied at normal temperature in the atmosphere. The results of the measurements are shown in Table 2.

Example 52

An organic EL device was prepared under the same conditions as in Example 49, except that the Compound (1-37) of Example 7 was used instead of the Compound (1-5) as the material for the second hole transport layer 5b. The resulting organic EL device was measured for the light emission characteristics exhibited when a direct current voltage was applied at normal temperature in the atmosphere. The results of the measurements are shown in Table 2.

Example 53

An organic EL device was prepared under the same conditions as in Example 49, except that the Compound (1-38) of Example 8 was used instead of the Compound (1-5) as the material for the second hole transport layer 5b. The resulting organic EL device was measured for the light emission characteristics exhibited when a direct current voltage was applied at normal temperature in the atmosphere. The results of the measurements are shown in Table 2.

Example 54

An organic EL device was prepared under the same conditions as in Example 49, except that the Compound (1-49) of Example 14 was used instead of the Compound (1-5) as the material for the second hole transport layer 5b. The resulting organic EL device was measured for the light emission characteristics exhibited when a direct current voltage was applied at normal temperature in the atmosphere. The results of the measurements are shown in Table 2.

Comparative Example 2

For comparison, an organic EL device was produced under the same conditions as in Example 49, except that the arylamine Compound (6-2) of the structural formula indicated above was used instead of the triarylamine derivative (6-1) as the material for the first hole transport layer 5a, and the arylamine Compound (6'-2) of the structural formula indicated above was used instead of the Compound (1-5) as the material for the second hole transport layer 5b. In this case, the first hole transport layer 5a and the second hole transport layer 5b function as an integrated hole transport layer (thickness 65 nm). The produced organic EL device was measured for the light emission characteristics exhibited when a direct current voltage was applied at normal temperature in the atmosphere. The results of the measurements are shown in Table 2.

Example 55

An organic EL device was prepared under the same conditions as in Example 43, except that the carbazole derivative (3-16) represented by the structural formula indicated below was used instead of the Compound (2-4) as the material for the luminous layer 6. The resulting organic EL device was measured for the light emission characteristics exhibited when a direct current voltage was applied at normal temperature in the atmosphere. The results of the measurements are shown in Table 3.

(3-16)

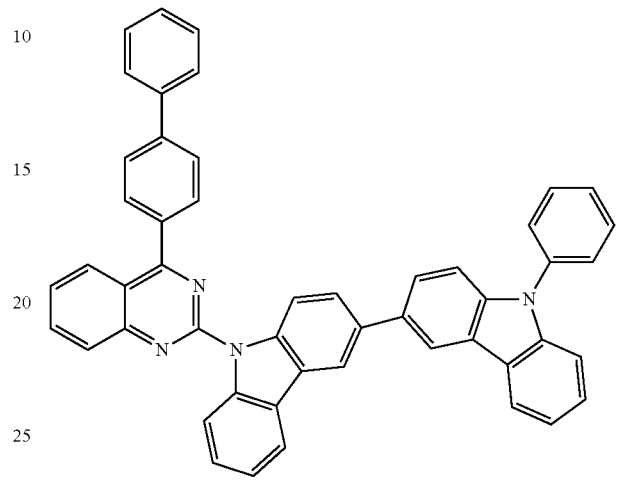

Example 56

An organic EL device was prepared under the same conditions as in Example 55, except that the Compound (1-32) of Example 5 was used instead of the Compound (1-5) as the material for the second hole transport layer 5b. The resulting organic EL device was measured for the light emission characteristics exhibited when a direct current voltage was applied at normal temperature in the atmosphere. The results of the measurements are shown in Table 3.

Example 57

An organic EL device was prepared under the same conditions as in Example 55, except that the Compound (1-34) of Example 6 was used instead of the Compound (1-5) as the material for the second hole transport layer 5b. The resulting organic EL device was measured for the light emission characteristics exhibited when a direct current voltage was applied at normal temperature in the atmosphere. The results of the measurements are shown in Table 3.

Example 58

An organic EL device was prepared under the same conditions as in Example 55, except that the Compound (1-37) of Example 7 was used instead of the Compound (1-5) as the material for the second hole transport layer 5b. The resulting organic EL device was measured for the light emission characteristics exhibited when a direct current voltage was applied at normal temperature in the atmosphere. The results of the measurements are shown in Table 3.

Example 59

An organic EL device was prepared under the same conditions as in Example 55, except that the Compound (1-38) of Example 8 was used instead of the Compound (1-5) as the material for the second hole transport layer 5b. The resulting organic EL device was measured for the light emission characteristics exhibited when a direct current voltage was applied at normal temperature in the atmosphere. The results of the measurements are shown in Table 3.

Example 60

An organic EL device was prepared under the same conditions as in Example 55, except that the Compound (1-49) of Example 14 was used instead of the Compound (1-5) as the material for the second hole transport layer 5b. The resulting organic EL device was measured for the light emission characteristics exhibited when a direct current voltage was applied at normal temperature in the atmosphere. The results of the measurements are shown in Table 3.

Comparative Example 3

For comparison, an organic EL device was produced under the same conditions as in Example 55, except that the arylamine Compound (6'-2) of the structural formula indicated above was used instead of the triarylamine derivative (6-1) as the material for the first hole transport layer 5a, and the arylamine Compound (6'-2) of the structural formula indicated above was used instead of the Compound (1-34) as the material for the second hole transport layer 5b. In this case, the first hole transport layer 5a and the second hole transport layer 5b function as an integrated hole transport layer (thickness 65 nm). The produced organic EL device was measured for the light emission characteristics exhibited when a direct current voltage was applied at normal temperature in the atmosphere. The results of the measurements are shown in Table 3.

The results obtained in measuring the device life by using the organic EL devices produced in Examples 43 to 60 and Comparative Examples 1 to are shown in Tables 1 to 3. The device life was measured as a time till the luminance attenuated to 6790 cd/m$^2$ (corresponds to 97% when the initial luminance is 100%; 97% attenuation) when a constant-current drive was performed at an emission luminance at the emission start time (initial luminance) of 7000 cd/m$^2$.

TABLE 1

|  | First hole transport layer | Second hole transport layer | Luminous layer | *1 (*5) | *2 (*5) | *3 (*5) | *4 (*5) | Device life, 97% attenuation (h) |
| --- | --- | --- | --- | --- | --- | --- | --- | --- |
| Ex. 43 | Cpd. 6-1 | Cpd. 1-5 | Cpd. 2-4/EMD-1 | 4.10 | 2770 | 27.70 | 21.43 | 166 |
| Ex. 44 | Cpd. 6-1 | Cpd. 1-32 | Cpd. 2-4/EMD-1 | 4.36 | 2642 | 26.42 | 19.11 | 151 |
| Ex. 45 | Cpd. 6-1 | Cpd. 1-34 | Cpd. 2-4/EMD-1 | 4.01 | 2606 | 26.06 | 20.58 | 132 |
| Ex. 46 | Cpd. 6-1 | Cpd. 1-37 | Cpd. 2-4/EMD-1 | 4.27 | 2768 | 27.68 | 20.54 | 145 |
| Ex. 47 | Cpd. 6-1 | Cpd. 1-38 | Cpd. 2-4/EMD-1 | 4.13 | 2509 | 25.09 | 19.15 | 130 |
| Ex. 48 | Cpd. 6-1 | Cpd. 1-49 | Cpd. 2-4/EMD-1 | 4.10 | 2814 | 28.14 | 21.80 | 160 |
| Comp. Ex. 1 | Cpd. 6'-2 | Cpd. 6'-2 | Cpd. 2-4/EMD-1 | 4.06 | 2394 | 23.97 | 18.54 | 55 |

*1: Voltage [V]
*2: Luminance [cd/m$^2$]
*3: Luminous efficiency [cd/A]
*4: Power efficiency [lm/W]
(*5): @10 mA/cm$^2$
Cpd.: Compound

TABLE 2

|  | First hole transport layer | Second hole transport layer | Luminous layer | *1 (*5) | *2 (*5) | *3 (*5) | *4 (*5) | Device life, 97% attenuation (h) |
| --- | --- | --- | --- | --- | --- | --- | --- | --- |
| Ex. 49 | Cpd. 6-1 | Cpd. 1-5 | Cpd. 3-14/EMD-1 | 3.35 | 2696 | 27.00 | 25.34 | 184 |
| Ex. 50 | Cpd. 6-1 | Cpd. 1-32 | Cpd. 3-14/EMD-1 | 3.58 | 2562 | 25.63 | 22.59 | 168 |
| Ex. 51 | Cpd. 6-1 | Cpd. 1-34 | Cpd. 3-14/EMD-1 | 3.27 | 2525 | 25.30 | 24.34 | 145 |
| Ex. 52 | Cpd. 6-1 | Cpd. 1-37 | Cpd. 3-14/EMD-1 | 3.50 | 2694 | 27.00 | 24.29 | 160 |
| Ex. 53 | Cpd. 6-1 | Cpd. 1-38 | Cpd. 3-14/EMD-1 | 3.38 | 2424 | 24.28 | 22.64 | 129 |
| Ex. 54 | Cpd. 6-1 | Cpd. 1-49 | Cpd. 3-14/EMD-1 | 3.35 | 2742 | 27.48 | 25.79 | 178 |
| Comp. Ex. 2 | Cpd. 6'-2 | Cpd. 6'-2 | Cpd. 3-14/EMD-1 | 3.31 | 2269 | 22.71 | 21.58 | 42 |

*1: Voltage [V]
*2: Luminance [cd/m$^2$]
*3: Luminous efficiency [cd/A]
*4: Power efficiency [lm/W]
(*5): @10 mA/cm$^2$
Cpd.: Compound

TABLE 3

| | First hole transport layer | Second hole transport layer | Luminous layer | *1 (*5) | *2 (*5) | *3 (*5) | *4 (*5) | Device life, 97% attenuation (h) |
|---|---|---|---|---|---|---|---|---|
| Ex. 55 | Cpd. 6-1 | Cpd. 1-5 | Cpd. 3-16/EMD-1 | 3.80 | 2584 | 25.84 | 21.35 | 277 |
| Ex. 56 | Cpd. 6-1 | Cpd. 1-32 | Cpd. 3-16/EMD-1 | 4.06 | 2453 | 24.56 | 19.03 | 252 |
| Ex. 57 | Cpd. 6-1 | Cpd. 1-34 | Cpd. 3-16/EMD-1 | 3.71 | 2415 | 24.20 | 20.50 | 218 |
| Ex. 58 | Cpd. 6-1 | Cpd. 1-37 | Cpd. 3-16/EMD-1 | 3.97 | 2581 | 25.82 | 20.46 | 242 |
| Ex. 59 | Cpd. 6-1 | Cpd. 1-38 | Cpd. 3-16/EMD-1 | 3.83 | 2321 | 23.23 | 19.07 | 200 |
| Ex. 60 | Cpd. 6-1 | Cpd. 1-49 | Cpd. 3-16/EMD-1 | 3.81 | 2634 | 26.34 | 21.72 | 326 |
| Comp. Ex. 3 | Cpd. 6'-2 | Cpd. 6'-2 | Cpd. 3-16/EMD-1 | 3.80 | 1980 | 19.80 | 16.90 | 86 |

*1: Voltage [V]
*2: Luminance [cd/m$^2$]
*3: Luminous efficiency [cd/A]
*4: Power efficiency [lm/W]
(*5): @10 mA/cm$^2$
Cpd.: Compound As indicated in Table 1, comparing Examples 43 to 48 and Comparative Example 1, which had the same combination of materials of the luminous layer, in the organic EL devices of Examples 43 to 48, the luminous efficiency at the time a current with a current density of 10 mA/cm$^2$ was flowing was 25.09 cd/A to 28.14 cd/A which was higher than 23.97 cd/A in the organic EL device of Comparative Example 1. Further, the power efficiency in the organic EL devices of Examples 43 to 48 was 19.11 lm/W to 21.80 lm/W which was also higher than 18.54 lm/W in the organic EL device of Comparative Example 1. The device life (97% attenuation) in the organic EL devices of Examples 43 to 48 was 130 h to 166 h which was much longer than 55 h in the organic EL device of Comparative Example 1.

As indicated in Table 2, comparing Examples 49 to 54 and Comparative Example 2, which had the same combination of materials of the luminous layer, in the organic EL devices of Examples 49 to 54, the luminous efficiency at the time a current with a current density of 10 mA/cm$^2$ was flowing was 24.28 cd/A to 27.48 cd/A which was higher than 22.71 cd/A in the organic EL device of Comparative Example 2. Further, the power efficiency in the organic EL devices of Examples 49 to 54 was 22.59 lm/W to 25.79 lm/W which was also higher than 21.58 lm/W in the organic EL device of Comparative Example 2. The device life (97% attenuation) in the organic EL devices of Examples 49 to 54 was 129 h to 184 h which was much longer than 42 h in the organic EL device of Comparative Example 2.

As indicated in Table 3, comparing Examples 55 to 60 and Comparative Example 3, which had the same combination of materials of the luminous layer, in the organic EL devices of Examples 55 to 60, the luminous efficiency at the time a current with a current density of 10 mA/cm$^2$ was flowing was 23.23 cd/A to 26.34 cd/A which was higher than 19.80 cd/A in the organic EL device of Comparative Example 3. Further, the power efficiency in the organic EL devices of Examples 55 to 60 was 19.03 lm/W to 21.72 lm/W which was also higher than 16.90 lm/W in the organic EL device of Comparative Example 3. The device life (97% attenuation) in the organic EL devices of Examples 55 to 60 was 200 h to 326 h which was much longer than 86 h in the organic EL device of Comparative Example 3.

Example 61

An organic EL device was produced, as depicted in FIG. 1, by forming in advance an ITO electrode as the transparent anode 2 on the glass substrate 1, and then vapor depositing thereon the hole injection layer 3, the first hole transport layer 5a, the second hole transport layer 5b, the luminous layer 6, the electron transport layer 7, the electron injection layer 8, and the cathode (aluminum electrode) 9 in the order of description.

More specifically, the glass substrate 1 on which an ITO film with a thickness of 150 nm was grown was ultrasonically cleaned for 20 min in isopropyl alcohol and then dried for 10 min on a hot plate heated to 200° C. Then, UV/ozone treatment was performed for 15 min, the ITO-attached glass substrate was attached inside a vacuum vapor deposition device, and pressure was reduced to 0.001 Pa or less.

Then, HIM-1 of the structural formula indicated above was formed to a film thickness of 5 nm as the hole injection layer 3 so as to cover the transparent electrode 2.

The triarylamine derivative (6-1) represented by the structural formula indicated above was formed as the first hole transport layer 5a to a film thickness of 60 nm on the hole injection layer 3.

The Compound (1-6) of Example 2 was formed as the second hole transport layer 5b to a film thickness of 5 nm on the first hole transport layer 5a.

A compound EMD-1 of the structural formula indicated above and the Compound (2-3) of Example 18 were formed as the luminous layer 6 to a film thickness of 20 nm on the second hole transport layer 5b by binary vapor deposition at vapor deposition rates such that the vapor deposition rate ratio of EMD-1 to Compound (2-3) was 5:95.

An anthracene derivative (5a-1) of the structural formula indicated below and ETM-1 of the structural formula indicated above were formed as the electron transport layer 7 to a film thickness of 30 nm on the luminous layer 6 by binary vapor deposition at vapor deposition rates such that the vapor deposition rate ratio of the anthracene derivative (5a-1) to ETM-1 was 50:50.

Lithium fluoride was formed as the electron injection layer 8 to a film thickness of 1 nm on the electron transport layer 7.

Finally, the cathode 9 was formed by vapor depositing aluminum to 100 nm.

The produced organic EL device was measured for the light emission characteristics exhibited when a direct current voltage was applied at normal temperature in the atmosphere. The results of the measurements are shown in Table 4.

(1-6)

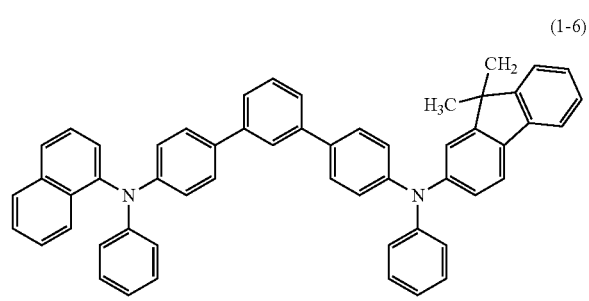

(1a-a)

(2-3)

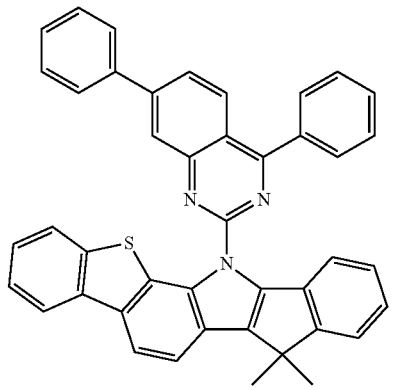

(2a)

(5a-1)

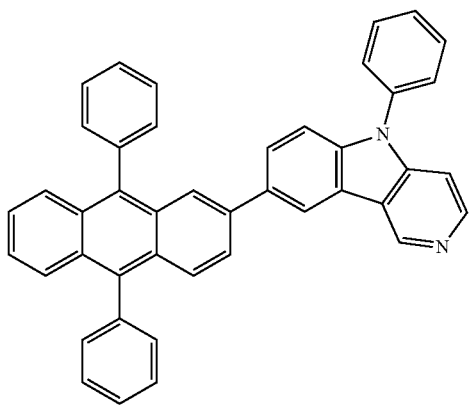

Example 62

An organic EL device was prepared under the same conditions as in Example 61, except that the Compound (1-34) of Example 6 was used instead of the Compound (1-6) as the material for the second hole transport layer 5b. The resulting organic EL device was measured for the light emission characteristics exhibited when a direct current voltage was applied at normal temperature in the atmosphere. The results of the measurements are shown in Table 4.

Example 63

An organic EL device was prepared under the same conditions as in Example 61, except that the Compound (1-37) of Example 7 was used instead of the Compound (1-6) as the material for the second hole transport layer 5b. The resulting organic EL device was measured for the light emission characteristics exhibited when a direct current voltage was applied at normal temperature in the atmosphere. The results of the measurements are shown in Table 4.

Example 64

An organic EL device was prepared under the same conditions as in Example 61, except that the Compound (1-41) of Example 10 was used instead of the Compound (1-6) as the material for the second hole transport layer 5b. The resulting organic EL device was measured for the light emission characteristics exhibited when a direct current voltage was applied at normal temperature in the atmosphere. The results of the measurements are shown in Table 4.

(1-41)

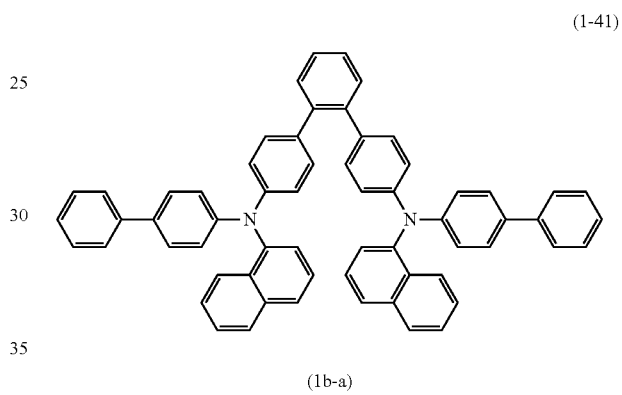

(1b-a)

Comparative Example 4

For comparison, an organic EL device was produced under the same conditions as in Example 61, except that the arylamine Compound (6'-2) of the structural formula indicated above was used instead of the triarylamine derivative of the general formula (6-1) as the material for the first hole transport layer 5a, and the arylamine Compound (6'-2) of the structural formula indicated above was used instead of the Compound (1-6) as the material for the second hole transport layer 5b. In this case, the first hole transport layer 5a and the second hole transport layer 5b function as an integrated hole transport layer (thickness 65 nm). The produced organic EL device was measured for the light emission characteristics exhibited when a direct current voltage was applied at normal temperature in the atmosphere. The results of the measurements are shown in Table 4.

Example 65

An organic EL device was prepared under the same conditions as in Example 61, except that the Compound (3-11) of Example 38 was used instead of the Compound (2-3) as the material for the luminous layer 6. The resulting organic EL device was measured for the light emission characteristics exhibited when a direct current voltage was applied at normal temperature in the atmosphere. The results of the measurements are shown in Table 5.

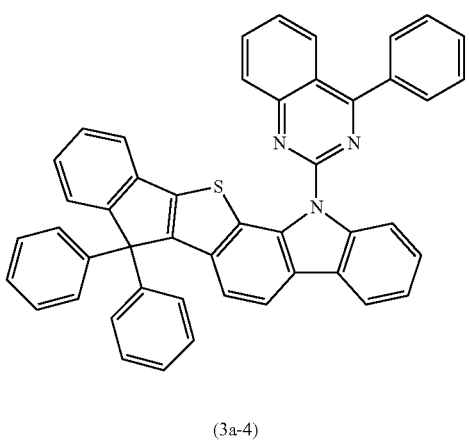

(3a-4)

Example 66

An organic EL device was prepared under the same conditions as in Example 65, except that the Compound (1-34) of Example 6 was used instead of the Compound (1-6) as the material for the second hole transport layer 5b. The resulting organic EL device was measured for the light emission characteristics exhibited when a direct current voltage was applied at normal temperature in the atmosphere. The results of the measurements are shown in Table 5.

Example 67

An organic EL device was prepared under the same conditions as in Example 65, except that the Compound (1-37) of Example 7 was used instead of the Compound (1-6) as the material for the second hole transport layer 5b. The resulting organic EL device was measured for the light emission characteristics exhibited when a direct current voltage was applied at normal temperature in the atmosphere. The results of the measurements are shown in Table 5.

Example 68

An organic EL device was prepared under the same conditions as in Example 65, except that the Compound (1-41) of Example 10 was used instead of the Compound (1-6) as the material for the second hole transport layer 5b. The resulting organic EL device was measured for the light emission characteristics exhibited when a direct current voltage was applied at normal temperature in the atmosphere. The results of the measurements are shown in Table 5.

Comparative Example 5

For comparison, an organic EL device was produced under the same conditions as in Example 65, except that the arylamine Compound (6'-2) of the structural formula indicated above was used instead of the triarylamine derivative of the general formula (6-1) as the material for the first hole transport layer 5a, and the arylamine Compound (6'-2) of the structural formula indicated above was used instead of the Compound (1-6) as the material for the second hole transport layer 5b. In this case, the first hole transport layer 5a and the second hole transport layer 5b function as an integrated hole transport layer (thickness 65 nm). The produced organic EL device was measured for the light emission characteristics exhibited when a direct current voltage was applied at normal temperature in the atmosphere. The results of the measurements are shown in Table 5.

The results obtained in measuring the device life by using the organic EL devices produced in Examples 61 to 68 and Comparative Examples 4 and 5 are shown in Tables 4 and 5. The device life was measured as a time till the luminance attenuated to 6790 $cd/m^2$ (corresponds to 97% when the initial luminance is 100%; 97% attenuation) when a constant-current drive was performed at an emission luminance at the emission start time (initial luminance) of 7000 $cd/m^2$.

TABLE 4

| | First hole transport layer | Second hole transport layer | Luminous layer | *1 (*5) | *2 (*5) | *3 (*5) | *4 (*5) | Device life, 97% attenuation (h) |
|---|---|---|---|---|---|---|---|---|
| Ex. 61 | Cpd. 6-1 | Cpd. 1-6 | Cpd. 2-3/EMD-1 | 4.02 | 2739 | 27.41 | 21.40 | 107 |
| Ex. 62 | Cpd. 6-1 | Cpd. 1-34 | Cpd. 2-3/EMD-1 | 4.09 | 2675 | 26.79 | 20.61 | 129 |
| Ex. 63 | Cpd. 6-1 | Cpd. 1-37 | Cpd. 2-3/EMD-1 | 4.21 | 2794 | 27.95 | 20.87 | 141 |
| Ex. 64 | Cpd. 6-1 | Cpd. 1-41 | Cpd. 2-3/EMD-1 | 4.16 | 2645 | 26.47 | 20.00 | 161 |
| Comp. Ex. 4 | Cpd. 6'-2 | Cpd. 6'-2 | Cpd. 2-3/EMD-1 | 3.81 | 2129 | 21.30 | 17.57 | 51 |

*1: Voltage [V]
*2: Luminance [$cd/m^2$]
*3: Luminous efficiency [cd/A]
*4: Power efficiency [lm/W]
(*5): @10 $mA/cm^2$
Cpd.: Compound

TABLE 5

| | First hole transport layer | Second hole transport layer | Luminous layer | *1 (*5) | *2 (*5) | *3 (*5) | *4 (*5) | Device life, 97% attenuation (h) |
|---|---|---|---|---|---|---|---|---|
| Ex. 65 | Cpd. 6-1 | Cpd. 1-6 | Cpd. 3-11/EMD-1 | 3.40 | 2506 | 25.07 | 23.19 | 201 |
| Ex. 66 | Cpd. 6-1 | Cpd. 1-34 | Cpd. 3-11/EMD-1 | 3.39 | 2529 | 25.30 | 23.47 | 199 |

TABLE 5-continued

| | First hole transport layer | Second hole transport layer | Luminous layer | *1 (*5) | *2 (*5) | *3 (*5) | *4 (*5) | Device life, 97% attenuation (h) |
|---|---|---|---|---|---|---|---|---|
| Ex. 67 | Cpd. 6-1 | Cpd. 1-37 | Cpd. 3-11/EMD-1 | 3.33 | 2406 | 24.10 | 22.76 | 218 |
| Ex. 68 | Cpd. 6-1 | Cpd. 1-41 | Cpd. 3-11/EMD-1 | 3.38 | 2509 | 25.11 | 23.33 | 176 |
| Comp. Ex. 5 | Cpd. 6'-2 | Cpd. 6'-2 | Cpd. 3-11/EMD-1 | 3.28 | 2223 | 22.27 | 21.34 | 65 |

*1: Voltage [V]
*2: Luminance [cd/m$^2$]
*3: Luminous efficiency [cd/A]
*4: Power efficiency [lm/W]
(*5): @10 mA/cm$^2$
Cpd.: Compound As indicated in Table 4, comparing Examples 61 to 64 and Comparative Example 4, which had the same combination of materials of the luminous layer, in the organic EL devices of Examples 61 to 64, the luminous efficiency at the time a current with a current density of 10 mA/cm$^2$ was flowing was 26.47 cd/A to 27.95 cd/A which was higher than 21.30 cd/A in the organic EL device of Comparative Example 4. Further, the power efficiency in the organic EL devices of Examples 61 to 64 was 20.00 lm/W to 21.40 lm/W which was also higher than 17.57 lm/W in the organic EL device of Comparative Example 4. The device life (97% attenuation) in the organic EL devices of Examples 61 to 64 was 107 h to 161 h which was much longer than 51 h in the organic EL device of Comparative Example 4.

As indicated in Table 5, comparing Examples 65 to 68 and Comparative Example 5, which had the same combination of materials of the luminous layer, in the organic EL devices of Examples 65 to 68, the luminous efficiency at the time a current with a current density of 10 mA/cm$^2$ was flowing was 24.10 cd/A to 25.30 cd/A which was higher than 22.27 cd/A in the organic EL device of Comparative Example 5. Further, the power efficiency in the organic EL devices of Examples 65 to 68 was 22.76 lm/W to 23.47 lm/W which was also higher than 21.34 lm/W in the organic EL device of Comparative Example 5. The device life (97% attenuation) in the organic EL devices of Examples 65 to 68 was 176 h to 218 h which was much longer than 65 h in the organic EL device of Comparative Example 5.

In the organic EL device of the present invention, carrier balance inside the organic EL device is improved by combining a specific arylamine compound with a specific indenoindole derivative or specific carbazole derivative (and a specific benzotriazole derivative or a specific anthracene derivative). Furthermore, since the materials are combined such as to obtain the carrier balance matching the properties of the light-emitting materials, an organic EL device can be realized which is superior in luminous efficiency and life to the conventional organic EL devices.

INDUSTRIAL APPLICABILITY

In the organic EL device of the present invention, a specific arylamine compound is combined with a specific indenoindole derivative or a specific carbazole derivative (and a specific benzotriazole derivative or a specific anthracene derivative). As a result, the luminous efficiency is increased and durability of the organic EL device is improved. Thus, the organic EL device of the present invention can be put to uses such as domestic electrical appliances and illumination.

DESCRIPTION OF REFERENCE NUMERALS

1 Glass substrate
2 Transparent anode
3 Hole injection layer
5 Hole transport layer
5a First hole transport layer
5b Second hole transport layer
6 Luminous layer
7 Electron transport layer
8 Electron injection layer
9 Cathode

The invention claimed is:
1. An organic electroluminescence device having an anode, a hole transport layer, a luminous layer, an electron transport layer, and a cathode in order of description, wherein
the hole transport layer includes Compound (1-5), Compound (1-6), Compound (1-32), Compound (1-37), Compound (1-39), Compound (1-41), Compound (1-42), or Compound (1-45):

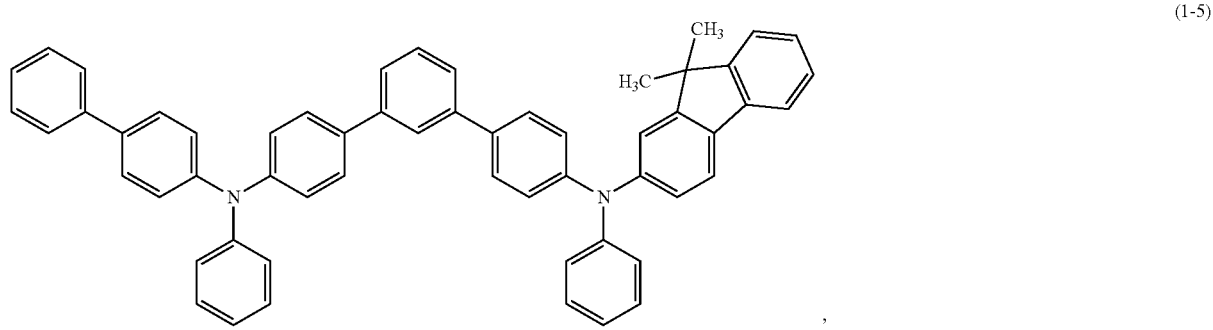

(1-5)

-continued
(1-6)
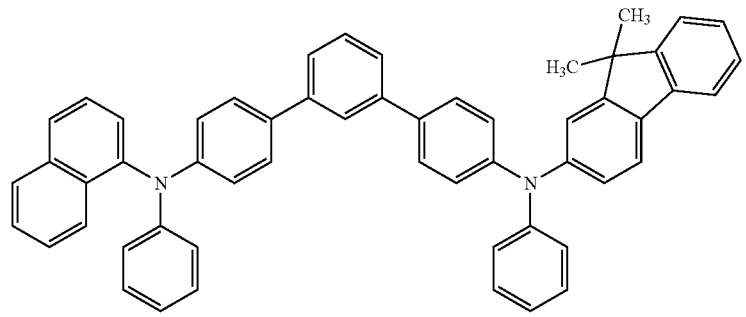
(1-32)
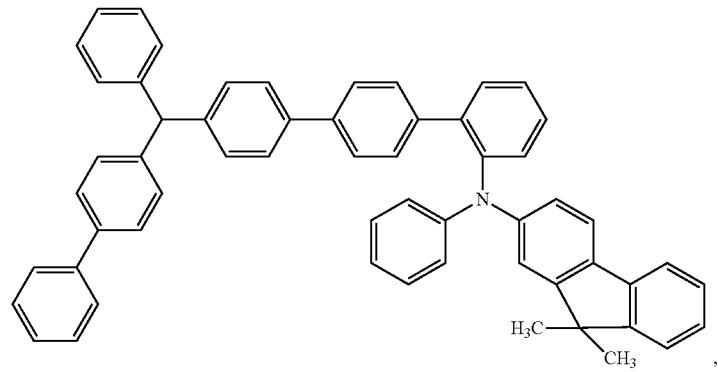
(1-37)
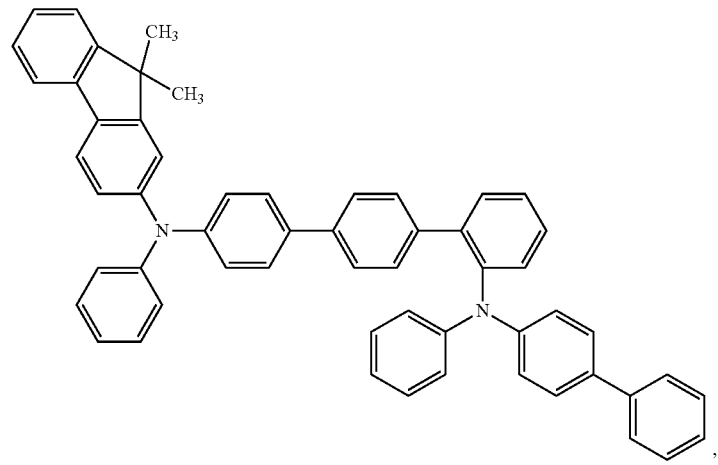
(1-39)
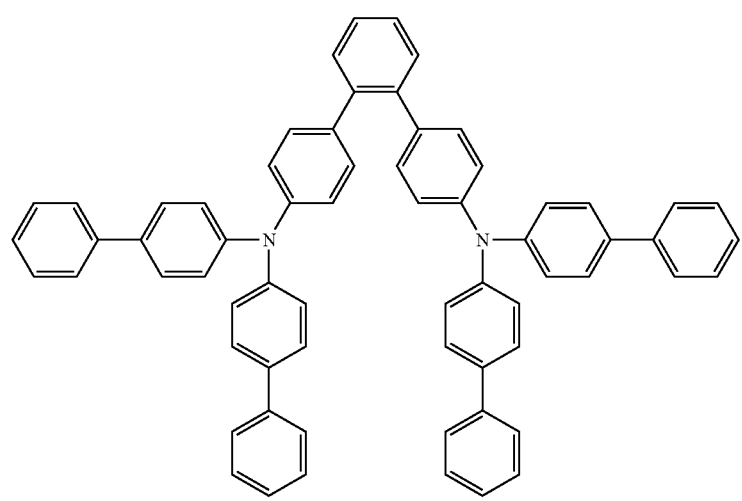

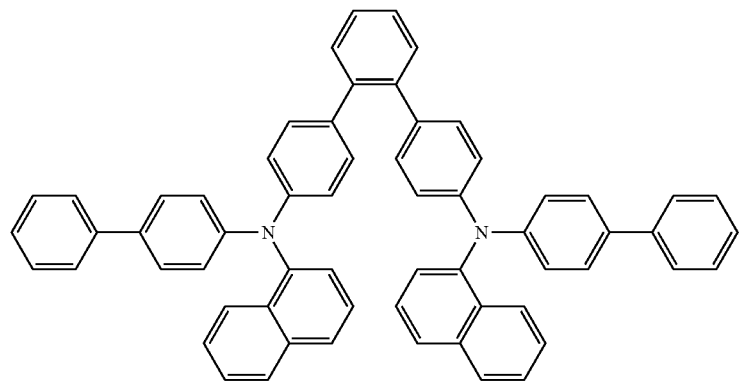

(1-41)

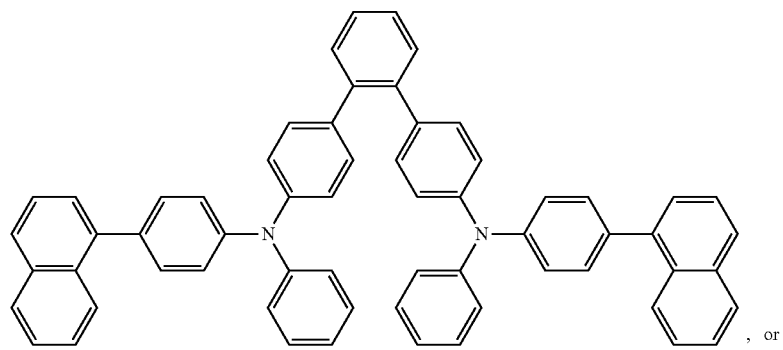

(1-42)

, or

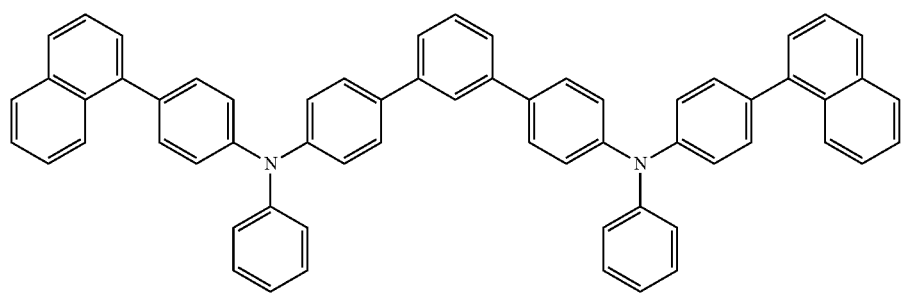

(1-45)

;

and
the luminous layer includes an indenoindole derivative represented by the following formula (2):

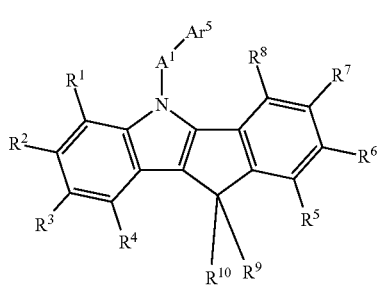

(2)

wherein
A$^1$ represents a divalent group of an aromatic hydrocarbon, a divalent group of an aromatic heterocyclic ring, or a single bond;
Ar$^5$ represents an aromatic hydrocarbon group or an aromatic heterocyclic group;
R$^1$ to R$^8$ each represents a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, an aryloxy group, or a disubstituted amino group having an aromatic hydrocarbon group or an aromatic heterocyclic group as a substituent;
respective groups among R$^1$ to R$^4$ may be bonded to each other via a single bond, a substituted or unsubstituted methylene group, an oxygen atom, or a sulfur atom to form a ring;
respective groups among R$^5$ to R$^8$ may be bonded to each other via a single bond, a substituted or unsubstituted methylene group, an oxygen atom, or a sulfur atom to form a ring;
some of R$^1$ to R$^4$ may be detached and the remaining groups of R$^1$ to R$^4$ may be bonded to vacancies generated by the detachment via a substituted or unsubstituted methylene group, an oxygen atom, a sulfur atom, or a monoarylamino group to form a ring;

some of $R^5$ to $R^8$ may be detached and the remaining groups of $R^5$ to $R^8$ may be bonded to vacancies generated by the detachment via a substituted or unsubstituted methylene group, an oxygen atom, a sulfur atom, or a monoarylamino group to form a ring; and $R^9$ and $R^{10}$ are each an alkyl group having 1 to 6 carbon atoms, an aromatic hydrocarbon group, or an aromatic heterocyclic group and may be bonded to each other via a single bond, a substituted or unsubstituted methylene group, an oxygen atom, or a sulfur atom to form a ring; or a carbazole derivative represented by the following formula (3):

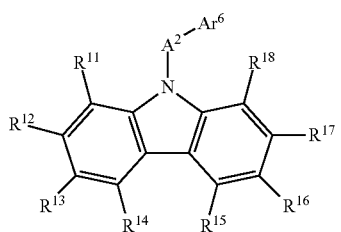

(3)

wherein, $A^2$ represents a divalent group of an aromatic hydrocarbon, a divalent group of an aromatic heterocyclic ring, or a single bond;

$Ar^6$ represents an aromatic hydrocarbon group or an aromatic heterocyclic group;

$R^{11}$ to $R^{18}$ each represents a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, an aryloxy group, or a disubstituted amino group having an aromatic hydrocarbon group or an aromatic heterocyclic group as a substituent;

respective groups among $R^{11}$ to $R^{14}$ may be bonded to each other via a single bond, a substituted or unsubstituted methylene group, an oxygen atom, or a sulfur atom to form a ring;

respective groups among $R^{15}$ to $R^{18}$ may be bonded to each other via a single bond, a substituted or unsubstituted methylene group, an oxygen atom, or a sulfur atom to form a ring;

some of $R^{11}$ to $R^{14}$ may be detached and the remaining groups of $R^{11}$ to $R^{14}$ may be bonded to vacancies generated by the detachment via a substituted or unsubstituted methylene group, an oxygen atom, a sulfur atom, or a monoarylamino group to form a ring; and some of $R^{15}$ to $R^{18}$ may be detached and the remaining groups of $R^{15}$ to $R^{18}$ may be bonded to vacancies generated by the detachment via a substituted or unsubstituted methylene group, an oxygen atom, a sulfur atom, or a monoarylamino group to form a ring;

provided that when any of $Ar^1$ to $Ar^4$ has a substituent, the substituent is a deuterium, an alkyl group having 1 to 6 carbon atoms, an alkenyl group having 2 to 6 carbon atoms, or an aromatic hydrocarbon group.

2. The organic electroluminescence device according to claim 1, wherein the electron transport layer includes a benzotriazole derivative represented by the following formula (4):

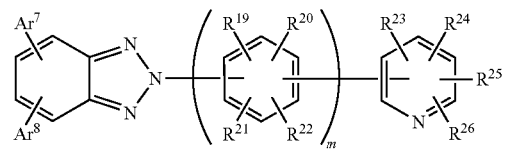

(4)

wherein, $Ar^7$ represents an aromatic hydrocarbon group or an aromatic heterocyclic group;

$Ar^8$ represents a hydrogen atom, a deuterium atom, an aromatic hydrocarbon group or an aromatic heterocyclic group;

$R^{19}$ to $R^{26}$ each represents a hydrogen atom, a deuterium atom, a fluorine atom, a chlorine atom, a cyano group, an alkyl group having 1 to 6 carbon atoms, an aromatic hydrocarbon group, or an aromatic heterocyclic group;

m represents an integer of 0 to 2;

when m is 2, a plurality of existing $R^{19}$, $R^{20}$, $R^{21}$, and $R^{22}$ may be the same or different.

3. The organic electroluminescence device according to claim 1, wherein the electron transport layer includes an anthracene derivative represented by the following formula (5):

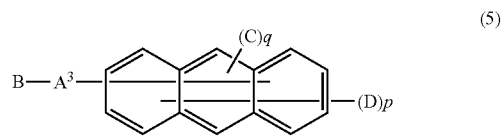

(5)

wherein, in p and q, p is an integer of 7 or 8 and q is an integer of 1 or 2 such that a sum of p and q being 9 is maintained;

$A^3$ represents a divalent group of an aromatic hydrocarbon, a divalent group of an aromatic heterocyclic ring, or a single bond;

B represents an aromatic heterocyclic group;

C represents an aromatic hydrocarbon group or an aromatic heterocyclic group; when q is 2, a plurality of existing C may be the same or different; and D represents a hydrogen atom, a deuterium atom, a fluorine atom, a chlorine atom, a cyano group, or an alkyl group having 1 to 6 carbon atoms, and a plurality of existing D may be the same or different.

4. The organic electroluminescence device according to claim 3, wherein the anthracene derivative is represented by the following formula (5a'):

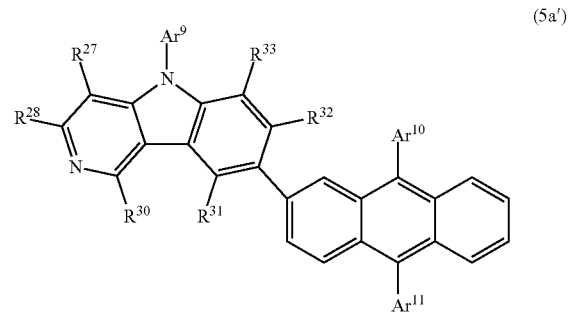

(5a')

wherein,

Ar$^9$ to Ar$^{11}$ each represents an aromatic hydrocarbon group or an aromatic heterocyclic group; and R$^{27}$, R$^{28}$, and R$^{30}$ to R$^{33}$ is each a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, or an aryloxy group and may be bonded to each other via a single bond, a substituted or unsubstituted methylene group, an oxygen atom, or a sulfur atom to form a ring.

5. The organic electroluminescence device according to claim 3, wherein the anthracene derivative is represented by the following formula (5b):

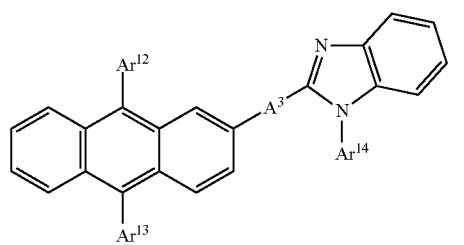

(5b)

wherein,

Ar$^{12}$ to Ar$^{14}$ each represents an aromatic hydrocarbon group or an aromatic heterocyclic group.

6. The organic electroluminescence device according to claim 3, wherein the anthracene derivative is represented by the following formula (5c):

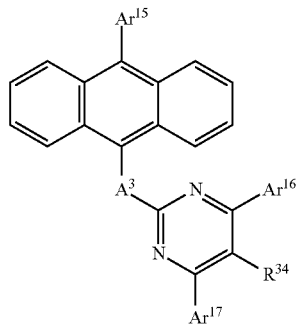

(5c)

wherein,

Ar$^{15}$ to Ar$^{17}$ each represents an aromatic hydrocarbon group or an aromatic heterocyclic group; and R$^{34}$ represents a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, or an aryloxy group.

7. The organic electroluminescence device according to claim 1, wherein the luminous layer includes a phosphorescence emitting material.

8. The organic electroluminescence device according to claim 7, wherein the phosphorescence emitting material is a metal complex comprising iridium or platinum.

9. The organic electroluminescence device according to claim 7, wherein the phosphorescence emitting material is a red luminous dopant.

* * * * *